(12) United States Patent
Tajima et al.

(10) Patent No.: US 9,793,305 B2
(45) Date of Patent: Oct. 17, 2017

(54) RADIATION IMAGE DETECTING DEVICE, RADIATION IMAGING SYSTEM AND OPERATION METHOD THEREOF

(71) Applicant: FUJIFILM CORPORATION, Tokyo (JP)

(72) Inventors: Takashi Tajima, Ashigarakami-gun (JP); Takeshi Kuwabara, Ashigarakami-gun (JP); Yusuke Kitagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 446 days.

(21) Appl. No.: 14/604,939

(22) Filed: Jan. 26, 2015

(65) Prior Publication Data

US 2015/0139398 A1 May 21, 2015

Related U.S. Application Data

(63) Continuation of application No. PCT/JP2013/065668, filed on Jun. 6, 2013.

(30) Foreign Application Priority Data

Jul. 27, 2012 (JP) ................................. 2012-166875
May 23, 2013 (JP) ................................. 2013-109300

(51) Int. Cl.
*G01T 1/02* (2006.01)
*H05G 1/38* (2006.01)
(Continued)

(52) U.S. Cl.
CPC ...... *H01L 27/14603* (2013.01); *A61B 6/4291* (2013.01); *A61B 6/4452* (2013.01);
(Continued)

(58) Field of Classification Search
CPC ........ A61B 6/42; A61B 6/4208; A61B 6/4283; A61B 6/4291; A61B 6/44; A61B 6/48;
(Continued)

(56) References Cited

U.S. PATENT DOCUMENTS

2004/0096035 A1    5/2004   Yamazaki et al.

FOREIGN PATENT DOCUMENTS

| JP | 7-201490 A    | 6/2004 |
|----|---------------|--------|
| JP | 2004-166724 A | 6/2004 |

OTHER PUBLICATIONS

International Search Report issued in PCT/JP2013/065668, mailed on Sep. 10, 2013.
(Continued)

*Primary Examiner* — Anastasia Midkiff
(74) *Attorney, Agent, or Firm* — Birch, Stewart, Kolasch & Birch, LLP

(57) ABSTRACT

In capturing an image of a grid by an image detector, a measurement pixel that is not in the position of a specific point having a maximum or minimum value of an output signal is referred to as a first measurement pixel, and a measurement pixel that is in the position of the specific point is referred to as a second measurement pixel. The disposition of the first and second measurement pixels are determined so as to satisfy the following condition: fG/fN≠odd number, wherein fG is a grid frequency and fN is a Nyquist frequency of pixels; and in shifting the grid C times by one pixel, the number of the first measurement pixels is larger than that of the second measurement pixels at any time in the range of a cycle C of a repetition pattern appearing in the image.

20 Claims, 22 Drawing Sheets

(51) Int. Cl.
  *H05G 1/28* (2006.01)
  *H05G 1/42* (2006.01)
  *H05G 1/44* (2006.01)
  *H01L 27/146* (2006.01)
  *H01L 27/148* (2006.01)
  *G01T 1/16* (2006.01)
  *G01T 1/29* (2006.01)
  *H01L 27/144* (2006.01)
  *A61B 6/00* (2006.01)

(52) U.S. Cl.
  CPC ............... *A61B 6/542* (2013.01); *G01T 1/026* (2013.01); *G01T 1/1603* (2013.01); *G01T 1/2985* (2013.01); *H01L 27/14812* (2013.01); *H05G 1/28* (2013.01); *H05G 1/38* (2013.01); *H05G 1/42* (2013.01); *H05G 1/44* (2013.01); *A61B 6/4233* (2013.01); *A61B 6/585* (2013.01); *H01L 27/1446* (2013.01); *H01L 27/14658* (2013.01)

(58) Field of Classification Search
  CPC ........... A61B 6/488; A61B 6/54; A61B 6/542; A61B 6/545; A61B 2562/00; A61B 2562/02; A61B 2562/06; A61B 2562/066; G01T 1/00; G01T 1/02; G01T 1/026; G01T 1/16; G01T 1/1603; G01T 1/24; G01T 1/246; G01T 1/247; H01L 27/1446; H01L 27/146; H01L 27/14601; H01L 27/14603; H01L 27/14609; H01L 27/14625; H01L 27/14658; H01L 27/14676; H01L 27/148; H01L 27/14806; H01L 27/14812; H05G 1/00; H05G 1/08; H05G 1/26; H05G 1/28; H05G 1/30; H05G 1/38; H05G 1/42; H05G 1/44; G05F 5/00; G05B 1/00; G05B 1/01; G05B 1/03; G05B 6/00; G05B 6/02; G05B 21/00; G05B 21/02; G05B 2219/15097

See application file for complete search history.

(56) References Cited

OTHER PUBLICATIONS

Written Opinion issued in PCT/JP2013/065668, mailed on Sep. 10, 2013.

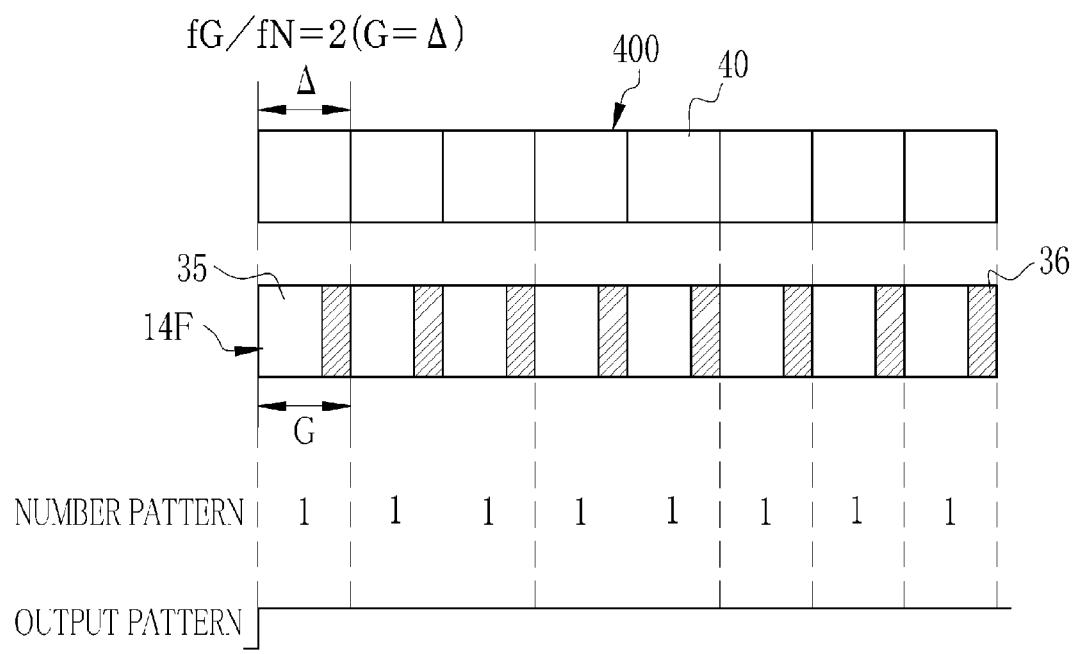
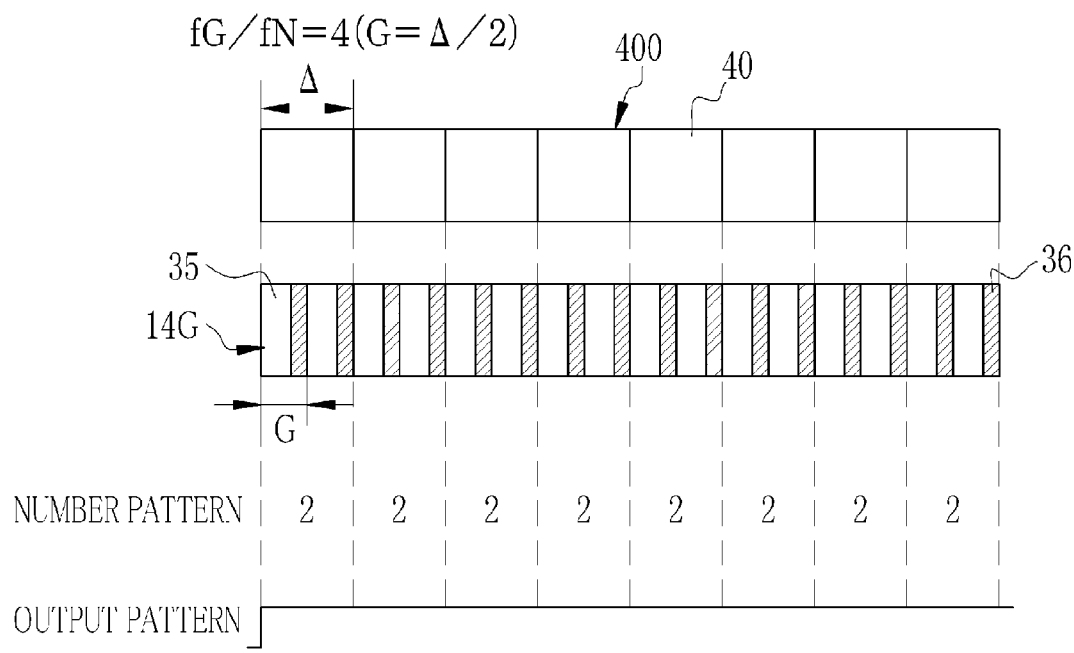

FIG. 13

| $fG/fN$ | RELATION BETWEEN $\Delta$ AND G | NUMBER PATTERN | OUTPUT PATTERN | REMARK |
|---|---|---|---|---|
| ⋮ | ⋮ | ⋮ | ⋮ | |
| 2/3 | $G=3\Delta$ | 0, 0, 1, 0, 0, 1, ⋯ | H, H, L, H, H, L, ⋯ | "HIGH" IS HIGH IN NUMBER. |
| ⋮ | ⋮ | ⋮ | ⋮ | |
| 1 | $G=2\Delta$ | 0, 1, 0, 1, 0, 1, ⋯ | H, L, H, L, H, L, ⋯ | TURN OF THE NUMBER OF "HIGH" AND "LOW". |
| ⋮ | ⋮ | ⋮ | ⋮ | |
| 4/3 | $G=3\Delta/2$ | 0, 1, 1, 0, 1, 1, ⋯ | H, L, L, H, L, L, ⋯ | "LOW" IS HIGH IN NUMBER. |
| ⋮ | ⋮ | ⋮ | ⋮ | |
| 2 | $G=\Delta$ | 1, 1, 1, 1, 1, 1, ⋯ | INVARIABLE | TURN OF THE NUMBER OF "HIGH" AND "LOW". TURN OF THE NUMBER OF ABSORBING LAYERS. |
| ⋮ | ⋮ | ⋮ | ⋮ | |
| 8/3 | $G=3\Delta/4$ | 1, 1, 2, 1, 1, 2, ⋯ | H, H, L, H, H, L, ⋯ | "HIGH" IS HIGH IN NUMBER. |
| ⋮ | ⋮ | ⋮ | ⋮ | |
| 3 | $G=2\Delta/3$ | 1, 2, 1, 2, 1, 2, ⋯ | H, L, H, L, H, L, ⋯ | TURN OF THE NUMBER OF "HIGH" AND "LOW". |
| ⋮ | ⋮ | ⋮ | ⋮ | |
| 10/3 | $G=3\Delta/5$ | 1, 2, 2, 1, 2, 2, ⋯ | H, L, L, H, L, L, ⋯ | "LOW" IS HIGH IN NUMBER. |
| ⋮ | ⋮ | ⋮ | ⋮ | |
| 4 | $G=\Delta/2$ | 2, 2, 2, 2, 2, 2, ⋯ | INVARIABLE | TURN OF THE NUMBER OF "HIGH" AND "LOW". TURN OF THE NUMBER OF ABSORBING LAYERS. |
| ⋮ | ⋮ | ⋮ | ⋮ | |
| 14/3 | $G=3\Delta/7$ | 2, 2, 3, 2, 2, 3, ⋯ | H, H, L, H, H, L, ⋯ | "HIGH" IS HIGH IN NUMBER. |
| ⋮ | ⋮ | ⋮ | ⋮ | |
| 5 | $G=2\Delta/5$ | 2, 3, 2, 3, 2, 3, ⋯ | H, L, H, L, H, L, ⋯ | TURN OF THE NUMBER OF "HIGH" AND "LOW". |
| ⋮ | ⋮ | ⋮ | ⋮ | |
| 16/3 | $G=3\Delta/8$ | 2, 3, 3, 2, 3, 3, ⋯ | H, L, L, H, L, L, ⋯ | "LOW" IS HIGH IN NUMBER. |
| ⋮ | ⋮ | ⋮ | ⋮ | |
| 6 | $G=\Delta/3$ | 3, 3, 3, 3, 3, 3, ⋯ | INVARIABLE | TURN OF THE NUMBER OF "HIGH" AND "LOW". TURN OF THE NUMBER OF ABSORBING LAYERS. |
| ⋮ | ⋮ | ⋮ | ⋮ | |
| 20/3 | $G=3\Delta/10$ | 3, 3, 4, 3, 3, 4, ⋯ | H, H, L, H, H, L, ⋯ | "HIGH" IS HIGH IN NUMBER. |
| ⋮ | ⋮ | ⋮ | ⋮ | |

FIG. 14

| $fG/fN$ | RELATION BETWEEN $\Delta$ AND G | IN THE CASE OF $\Delta=125\mu m$ | |
|---|---|---|---|
| | | G ($\mu m$) | NUMBER OF ABSORBING LAYERS (/cm) |
| ⋮ | ⋮ | ⋮ | ⋮ |
| 2/3 | G=3$\Delta$ | 375 | 26.7 |
| ⋮ | ⋮ | ⋮ | ⋮ |
| 1 | G=2$\Delta$ | 250 | 40 |
| ⋮ | ⋮ | ⋮ | ⋮ |
| 4/3 | G=3$\Delta$/2 | 187.5 | 53.3 |
| ⋮ | ⋮ | ⋮ | ⋮ |
| 2 | G=$\Delta$ | 125 | 80 |
| ⋮ | ⋮ | ⋮ | ⋮ |
| 8/3 | G=3$\Delta$/4 | 93.8 | 106.7 |
| ⋮ | ⋮ | ⋮ | ⋮ |
| 3 | G=2$\Delta$/3 | 83.3 | 120 |
| ⋮ | ⋮ | ⋮ | ⋮ |
| 10/3 | G=3$\Delta$/5 | 75 | 133.3 |
| ⋮ | ⋮ | ⋮ | ⋮ |
| 4 | G=$\Delta$/2 | 62.5 | 160 |
| ⋮ | ⋮ | ⋮ | ⋮ |
| 14/3 | G=3$\Delta$/7 | 53.6 | 186.7 |
| ⋮ | ⋮ | ⋮ | ⋮ |
| 5 | G=2$\Delta$/5 | 50 | 200 |
| ⋮ | ⋮ | ⋮ | ⋮ |
| 16/3 | G=3$\Delta$/8 | 46.9 | 213.3 |
| ⋮ | ⋮ | ⋮ | ⋮ |
| 6 | G=$\Delta$/3 | 41.7 | 240 |
| ⋮ | ⋮ | ⋮ | ⋮ |
| 20/3 | G=3$\Delta$/10 | 37.5 | 266.7 |
| ⋮ | ⋮ | ⋮ | ⋮ |

FIG. 15

| $f_G/f_N$ | RELATION BETWEEN $\Delta$ AND G | $f_{GN}$ | C(PIXEL) |
|---|---|---|---|
| ⋮ | ⋮ | | ⋮ |
| 2/3 | $G=3\Delta$ | $f_{GN}=f_G$ (j=0) | 3 |
| ⋮ | ⋮ | | ⋮ |
| 1 | $G=2\Delta$ | | 2 |
| ⋮ | ⋮ | | ⋮ |
| 4/3 | $G=3\Delta/2$ | $f_{GN}=2f_N-f_G$ (j=0) | 3 |
| ⋮ | ⋮ | | ⋮ |
| 2 | $G=\Delta$ | | 0 |
| ⋮ | ⋮ | | ⋮ |
| 8/3 | $G=3\Delta/4$ | $f_{GN}=f_G-2f_N$ (j=1) | 3 |
| ⋮ | ⋮ | | ⋮ |
| 3 | $G=2\Delta/3$ | | 2 |
| ⋮ | ⋮ | | ⋮ |
| 10/3 | $G=3\Delta/5$ | $f_{GN}=4f_N-f_G$ (j=1) | 3 |
| ⋮ | ⋮ | | ⋮ |
| 4 | $G=\Delta/2$ | | 0 |
| ⋮ | ⋮ | | ⋮ |
| 14/3 | $G=3\Delta/7$ | $f_{GN}=f_G-4f_N$ (j=2) | 3 |
| ⋮ | ⋮ | | ⋮ |
| 5 | $G=2\Delta/5$ | | 2 |
| ⋮ | ⋮ | | ⋮ |
| 16/3 | $G=3\Delta/8$ | $f_{GN}=6f_N-f_G$ (j=2) | 3 |
| ⋮ | ⋮ | | ⋮ |
| 6 | $G=\Delta/3$ | | 0 |
| ⋮ | ⋮ | ⋮ | ⋮ |
| 20/3 | $G=3\Delta/10$ | $f_{GN}=f_G-6f_N$ (j=3) | 3 |
| ⋮ | ⋮ | | ⋮ |

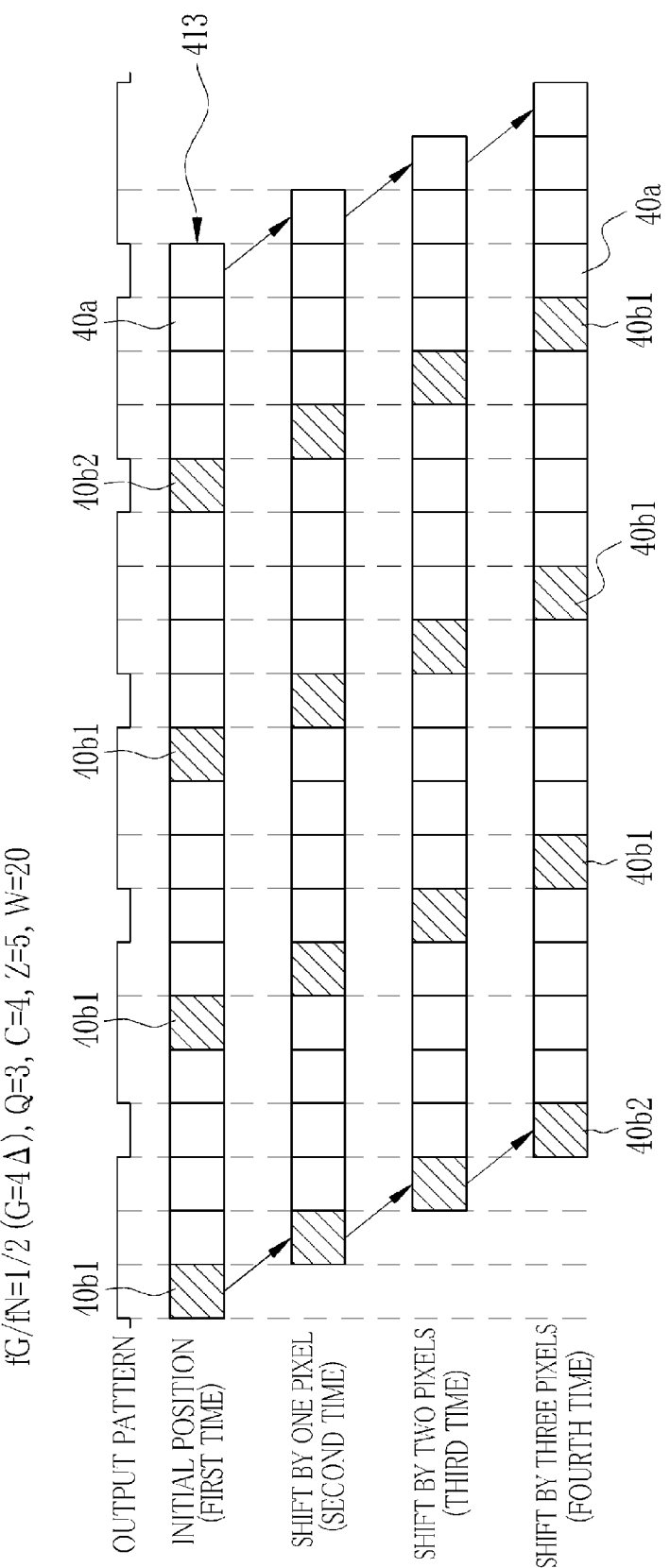

FIG. 19

| $f_G/f_N$ | RELATION BETWEEN $\Delta$ AND G | CASE | M | CONDITION OF Q (MINIMUM VALUE) |
|---|---|---|---|---|
| ⋮ | ⋮ | | | |
| 2/3 | G=3$\Delta$ | 1 | 0 | Q≧1 |
| ⋮ | ⋮ | | | |
| 1 | G=2$\Delta$ | / | / | / |
| ⋮ | ⋮ | | | |
| 4/3 | G=3$\Delta$/2 | 2 | 0 | Q≧1.5 |
| ⋮ | ⋮ | | | |
| 2 | G=$\Delta$ | / | / | / |
| ⋮ | ⋮ | | | |
| 8/3 | G=3$\Delta$/4 | 1 | 1 | Q≧1.5 |
| ⋮ | ⋮ | | | |
| 3 | G=2$\Delta$/3 | / | / | / |
| ⋮ | ⋮ | | | |
| 10/3 | G=3$\Delta$/5 | 2 | 1 | Q≧7/3 |
| ⋮ | ⋮ | | | |
| 4 | G=$\Delta$/2 | / | / | / |
| ⋮ | ⋮ | | | |
| 14/3 | G=3$\Delta$/7 | 1 | 2 | Q≧7/3 |
| ⋮ | ⋮ | | | |
| 5 | G=2$\Delta$/5 | / | / | / |
| ⋮ | ⋮ | | | |
| 16/3 | G=3$\Delta$/8 | 2 | 2 | Q≧4 |
| ⋮ | ⋮ | | | |
| 6 | G=$\Delta$/3 | / | / | / |
| ⋮ | ⋮ | | | |
| 20/3 | G=3$\Delta$/10 | 1 | 3 | Q≧4 |
| ⋮ | ⋮ | | | |

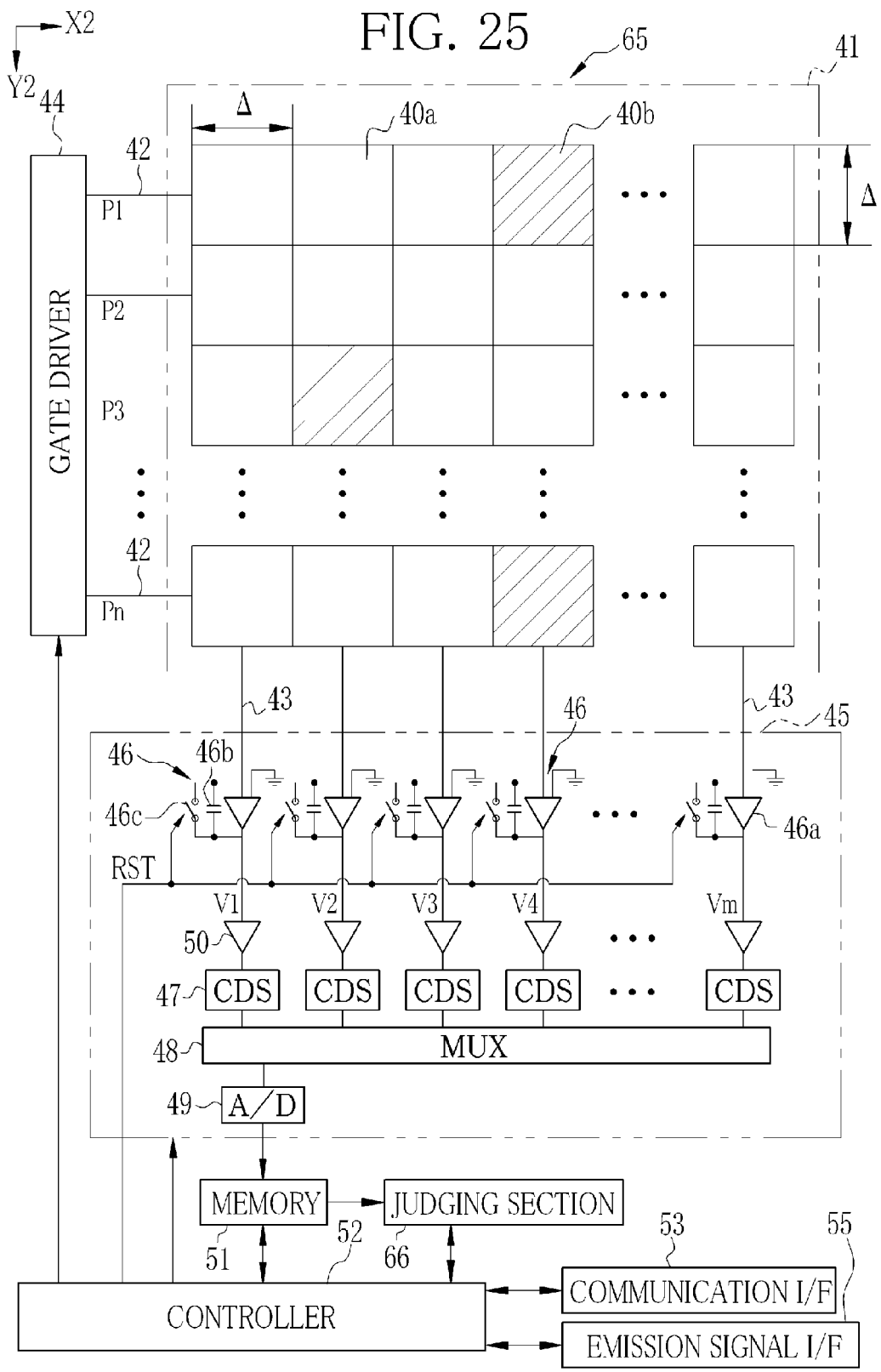

RADIATION IMAGE DETECTING DEVICE, RADIATION IMAGING SYSTEM AND OPERATION METHOD THEREOF

CROSS-REFERENCE TO RELATED APPLICATIONS

This application is a continuation of PCT International Application No. PCT/JP2013/065668 filed on Jun. 6, 2013, which claims priority under 35 U.S.C. 35 §119(a) to Japanese Patent Application No. 2012-166875 filed on Jul. 27, 2012 and Japanese Patent Application No. 2013-109300 filed on May 23, 2013. Each of the above applications is hereby expressly incorporated by reference, in its entirety, into the present application.

BACKGROUND OF THE INVENTION

1. Field of the Invention

The present invention relates to a radiation image detecting device for detecting a radiographic image through a grid, a radiation imaging system and an operation method thereof.

2. Description Related to the Prior Art

In a medical field, a radiation imaging system, for example, an X-ray imaging system using X-rays is known. The X-ray imaging system is constituted of an X-ray generating apparatus for producing the X-rays, and an X-ray imaging apparatus for taking an X-ray image formed by the X-rays passed through an object (a patient). The X-ray generating apparatus has an X-ray source for emitting the X-rays to the object, a source control device for controlling the operation of the X-ray source, and an emission switch for commanding the source control device to start X-ray emission. The X-ray imaging apparatus has an X-ray image detecting device for detecting the X-ray image by converting the X-rays passed through each part of the object into an electric signal, and a console that controls the operation of the X-ray image detecting device and saves and displays the X-ray image.

The X-ray image detecting device includes an image detector for converting the X-ray image into the electric signal, a controller for controlling the image detector, and the like. As the image detector, a flat panel detector (FPD) having a lot of pixels arrayed in two dimensions in an imaging area is widely used. Each pixel accumulates electric charge in accordance with an X-ray dose (a time-integrated X-ray value). After imaging, the electric charge accumulated in each pixel is read out to a signal processing circuit through a switching element such as a TFT (thin film transistor). The signal processing circuit converts the electric charge of each pixel into a voltage signal, and outputs the voltage signals as an X-ray image signal.

There is known an X-ray image detecting device that has an X-ray dose measurement function and an automatic exposure control (AEC) function (for example, Japanese Patent Laid-Open Publication No. 07-201490). In this X-ray image detecting device, one or a plurality of measurement pixels for measuring an X-ray dose is disposed in the imaging area of the image detector, together with normal pixels (X-ray image detection pixels) for detecting an X-ray image. This measurement pixel is used as a dose measurement sensor for measuring the X-ray dose. A measurement signal is read out of the measurement pixel at regular time intervals and integrated to measure the X-ray dose. At the instant when the X-ray dose reaches a predetermined emission stop threshold value (a target X-ray dose) the AEC function commands the X-ray source to stop X-ray emission. In the following description, both of the normal pixels and the measurement pixels are collectively called pixels. The pixel refers to an ingredient that has at least a conversion function for converting a small portion of the X-ray image into the electric charge.

The measurement pixel is the same as or several times larger than the normal pixel in size, and is disposed in one or a plurality of portions in the imaging area. Provided that the measurement pixel is the same size as the normal pixel, the normal pixel may be substituted with the measurement pixel or changed into the measurement pixel by easy modification. In some cases, the normal pixel may be used as the measurement pixel, or variation in a leak current or a bias current of the normal pixel may be detected to measure the X-ray dose therefrom. The small-sized measurement pixel does not hinder the detection of the X-ray image and hence facilitates detecting the X-ray image with high resolution, as compared with a conventional large-sized dose measurement sensor such as an ion chamber. Furthermore, selective use of the measurement pixels in accordance with a body part to be imaged makes it possible to precisely measure the X-ray dose passed through the body part.

By the way, in X-ray imaging, the X-rays produce scattered radiation in passing through the object. To remove this scattered radiation, a thin plate-shaped grid is used often. This grid is disposed between the object and the X-ray image detecting device, and preferably just in front of the X-ray image detecting device. There are two types of grids, one known as a movable grid swinging during X-ray imaging and the other known as a static grid standing still. In the following description, either type of grid is simply called grid except in cases where distinction between the types is necessary.

The grid is provided with strip-shaped X-ray transparent layers and X-ray absorbing layers that extend in a column direction of the pixels and are alternately and repeatedly arranged along a row direction of the pixels. Since the X-ray absorbing layer absorbs the X-rays passed through the object, widening the X-ray absorbing layers deteriorates the image quality of the X-ray image to be taken. Accordingly, the width of the X-ray absorbing layer is, for example, of the order of $1/5$ to $1/3$ of the width of the X-ray transparent layer, in general.

According to X-ray imaging using the grid, since the X-ray absorbing layers of the grid attenuate the X-rays to be incident upon the measurement pixels, a measurement value of each measurement pixel has to be calibrated to measure an X-ray irradiation amount (an X-ray exposure amount) of the object. This calibration method of the measurement value is described in US Patent Application Publication No. 2004/0096035 corresponding to Japanese Patent Laid-Open Publication No. 2004-166724, for example. First, X-ray imaging is performed in a state of disposing no object with and without using the grid. From two images obtained thereby, a correction coefficient of each individual measurement pixel is calculated such that an output signal of the measurement pixel (referred to as an AEC pixel in the US Patent Application Publication No. 2004/0096035) becomes the same between with and without the grid. In imaging using the grid, the output signal of the measurement pixel is multiplied by the correction coefficient to calibrate the X-ray dose.

An arrangement direction of the X-ray transparent layers and the X-ray absorbing layers of the grid is orthogonal to a row direction of the pixels. Provided that the normal pixel and the measurement pixel are of the same size, the size of one normal pixel (the pitch of the pixels) is 100 μm to 200

μm, and hence the size of the measurement pixel is of the order of 100 μm to 200 μm. On the other hand, there are two types of grids in which the number of the X-ray absorbing layers per unit length in the arrangement direction is 100/cm and 32/cm. By converting this number into a grid pitch (the arrangement pitch of the X-ray absorbing layers), grid pitches of 100 μm and approximately 300 μm are obtained.

Taking the case of a grid pitch of 300 μm and a measurement pixel size of 100 μm as an example, since the width of the X-ray absorbing layers is approximately 50 μm to 100 μm, a shift of the positional relation between the grid and the measurement pixels changes overlap between the measurement pixels and the X-ray absorbing layers and hence largely varies the output signals.

Since the X-ray transparent layers and the X-ray absorbing layers are regularly arranged at a constant period in the grid, an M or M+1 (M is an integer of 0 or more) number of X-ray absorbing layers are opposed to an arbitrary measurement pixel in accordance with the relation between the grid pitch and the size of the measurement pixels. Thus, in a case where the positional relation between the grid and the measurement pixels is shifted, variation in the output signal of the measurement pixel has its maximum value that corresponds to attenuation of the X-rays absorbed by one X-ray absorbing layer relative to the measurement pixel. Given that each X-ray absorbing layer has an almost constant X-ray absorptivity, the variation in the output signal is increased with decrease in the number M. If the grid pitch takes a value close to the size of the measurement pixels, the number M is a relatively small value. Therefore, the output signal of the measurement pixel is especially susceptible to the X-ray absorbing layer, and a problem of measurement precision of the X-ray dose owing to the shift of the positional relation between the grid and the measurement pixels becomes conspicuous.

The effect of the X-ray absorbing layers can be calculated from an image of the stopped movable grid or the still grid captured in the absence of the object. According to experiment of the inventors, it is apparent that a pixel value is decreased on the order of 20% by a certain grid owing to the effect of the X-ray absorbing layer, by comparison between a large pixel value and a nearby decreased pixel value that the X-ray absorbing layer affects.

In a case where the grid is secured to the X-ray image detecting device, variations in attachment position of each part in manufacturing cause the shift of the positional relation between the grid and the measurement pixels. In the case of an electronic cassette separate from the grid or in the case of the grid detachable from an imaging stand or an imaging table, variations in loading position of the electronic cassette or the grid cause the shift of the positional relation between the grid and the measurement pixels. In some cases, the positional relation between the grid and the measurement pixels may be shifted by vibration and the like while imaging is repeatedly performed.

In the calibration method of the measurement pixels according to the US Patent Application Publication No. 2004/0096035, in a case where the positional relation between the grid and the measurement pixels is shifted whenever imaging is performed, a lot of calibration images are prepared in accordance with a shift amount, and the shift amount is detected in the imaging on the order of μm corresponding to the grid pitch. One of the calibration images is chosen in accordance with the shift amount, and the correction coefficient to correct sensitivity of the measurement pixel is calculated. This calibration method of the measurement pixels precisely measures the shift amount and allows calibration with high precision, but requires the many calibration images. Also, in a case where the positional relation between the grid and the measurement pixels is shifted during manufacturing, the calibration images have to be taken on a product-by-product basis, and its preparation operation requires much time and effort. Furthermore, a huge number of calibration images have to be prepared at the thought of oblique incidence of the X-rays upon the imaging area, so that realization is difficult. Accordingly, it is desired that the X-ray dose can be measured easily and precisely even if the positional relation between the measurement pixels (the dose measurement sensors, in general) and the grid is shifted, without using the huge number of calibration images.

SUMMARY OF THE INVENTION

An object of the present invention is to provide a radiation image detecting device that can precisely measure a radiation dose even if the positional relation between dose measurement sensors and a grid is shifted, and a radiation imaging system and an operation method thereof.

To achieve the above and other objects, a radiation image detecting device according to the present invention has an image detector formed with an imaging area. The radiation image detecting device is used together with a grid capable of being disposed in front of the image detector. In the radiation image detecting device, the grid is provided with strip-shaped radiation transparent layers and radiation absorbing layers extending in a first direction to remove scattered rays produced upon radiation passing through an object. The plurality of the radiation transparent layers and the radiation absorbing layers are formed at a grid pitch G alternately in a second direction orthogonal to the first direction. The imaging area is provided with a plurality of pixels arrayed in the second direction at a pixel pitch $\Delta$ and a plurality of dose measurement sensors. The plurality of pixels accumulate electric charge in accordance with a received radiation dose in a readable manner to detect a radiographic image of the object. The plurality of dose measurement sensors measure the received radiation dose. Provided that the image detector captures a radiographic image of the grid, and the dose measurement sensor that is not situated in a specific position in which an output signal is at a maximum value or a minimum value is designated as a first dose measurement sensor and the dose measurement sensor that is in the specific position is designated as a second dose measurement sensor, the position of the plurality of dose measurement sensors is determined so as to satisfy the following condition 1:

condition 1:

provided that fG/fN≠odd number and the grid and the pixels are relatively shifted to the second direction C times by one pixel, the number of the first dose measurement sensors is larger than the number of the second dose measurement sensors at any time within the range of a cycle C. Wherein, fG=1/G represents a grid frequency. fN=1/(2Δ) represents a Nyquist frequency of the pixels. The cycle C is a cycle of a repetition pattern appearing in the second direction in the radiographic image of the grid, and is represented in units of the number of the pixels.

It is preferable that the radiation image detecting device further include a judging section for judging an emission state of the radiation based on a measurement value of at least a group of dose measurement sensors, and a controller for performing control in accordance with a judgment result of the judging section. The group of dose measurement sensors are at least a part of the plurality of dose measurement sensors, disposed in the second direction, of a number corresponding to the cycle C.

The pixels preferably include a normal pixel for detecting the radiographic image, and a measurement pixel of the same size as the normal pixel and used as the dose measurement sensor. The normal pixel and the measurement pixel are disposed in the first and second directions in two dimensions in a mixed manner.

The normal pixel and the measurement pixel are preferably connected to a common signal processing circuit. Electric charge of the normal pixel is preferably accumulated, and electric charge of the measurement pixel is preferably read out to the signal processing circuit during emission of the radiation.

Furthermore, the group of measurement pixels are further situated so as to satisfy the following condition 2:

condition 2:

provided that the grid and the pixels are relatively shifted by one pixel, the following conditional expression 1 or the following conditional expression 2 is satisfied at the any time:

in the case of $2j<fG/fN<2j+1$, conditional expression 1:

$$Q \geq \frac{k(M \cdot a - 1) + 50a}{k(1 - M \cdot a)} \quad (1c)$$

in the case of $2j+1<fG/fN<2j+2$, conditional expression 2:

$$Q \geq \frac{k - a\{k(M+1) + 50\}}{k\{a(M+1) - 1\}} \quad (2c)$$

wherein, "Q" represents the number of first measurement pixels corresponding to the first dose measurement sensors, relative to one second measurement pixel corresponding to the second dose measurement sensor. "a" represents a radiation absorptivity of one of the radiation absorbing layers. "M" represents a minimum value of the number of the radiation absorbing layers projected to the measurement pixel. "k" represents a tolerance (±k %) in variations of the measurement value of the group of measurement pixels in every of the times, and "j" represents an integer.

The tolerance in variations is preferably k≤5 or k≤2.5.

Provided that Z (a pixel number) represents a disposition cycle of the measurement pixels, and LCM(C,Z) represents a least common multiple of the cycle C and the disposition cycle Z, the disposition cycle Z of the measurement pixels is preferably determined so as to satisfy the following conditional expression 3:

$LCM(C,Z) \geq (Q+1) \cdot Z$. conditional expression 3:

In the case of selectively using a plurality of grids having different minimum values of Q, a highest value out of the plurality of minimum values of Q is preferably used in common.

Also, in the case of selectively using a plurality of grids having different conditions of the disposition cycle Z, a least common multiple of a plurality of the disposition cycles Z is preferably used as a disposition cycle Z sharable among the grids.

The position of the group of measurement pixels may be irregular, in addition to being regular.

Under the condition 1, values of the pixel pitch Δ and the grid pitch G are preferably determined so as to satisfy one of the following conditional expressions 4 to 7:

$fG/fN \leq 2/3$ conditional expression 4:

$4/3 \leq fG/fN \leq 8/3$ conditional expression 5:

$10/3 \leq fG/fN \leq 14/3$ conditional expression 6:

$16/3 \leq fG/fN \leq 20/3$. conditional expression 7:

Provided that fA represents the ratio fN/Z between the disposition cycle Z of the measurement pixels and a Nyquist frequency fN of the measurement pixels, values of the pixel pitch Δ, the grid pitch G, and the disposition cycle Z are preferably determined such that fG/fA=even number or fG/fA≠integer holds true.

In the case of satisfying the condition 1, the position of the group of measurement pixels is preferably determined so as to further satisfy the following condition 3:

condition 3:

the number of first measurement pixels corresponding to the first dose measurement sensors is invariable at any time, and the number of second measurement pixels corresponding to the second dose measurement sensors is invariable at any time.

The judging section preferably performs automatic exposure control in which the judging section judges whether or not a total radiation dose being an integrated value of a radiation dose measured by each of the measurement pixels or an average value of the total radiation doses reaches a target dose, and stops emission of the radiation in a case where the total radiation dose or the average value is judged to have reached the target dose.

It is preferable that the decision of the position of the group of measurement pixels stipulated in the second direction be also applied to the first direction.

The image detector is preferably an electronic cassette contained in a portable housing.

A radiation imaging system according to the present invention includes a radiation source for applying radiation to an object, a source control device for controlling operation of the radiation source, and the radiation image detecting device described above.

An operation method of the radiation imaging system according to the present invention includes a radiation dose measuring step, a judging step, and a radiation emission stopping step. In the radiation dose measuring step, at least a group of dose measurement sensors, out of the plurality of dose measurement sensors, measure a radiation dose. In the judging step, it is judged that whether or not a total radiation dose being an integrated value of each radiation dose measured by the group of dose measurement sensors or an average value of the total radiation doses reaches a target dose. In the radiation emission stopping step, the operation of the radiation source is stopped to stop emission of the radiation, at the instant when the total radiation dose or the average value reaches the target dose.

According to the present invention, the number of the first dose measurement sensors, which are not in the positions of specific points in which the output signal becomes the maximum value or the minimum value in the radiographic image of the grid, is set larger than the number of the second dose measurement sensors, which are in the positions of the specific points. Therefore, it is possible to reduce variation in the output of the dose measurement sensors and precisely measure the radiation dose, even if the positional relation with the grid is shifted.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 8 is an explanatory view similar to FIG. 6 in the case of fG/fN=2;

FIG. 9 is an explanatory view similar to FIG. 6 in the case of fG/fN=4;

FIG. 13 is a table of a number pattern and an output pattern relative to each value of fG/fN;

FIG. 14 is a table of a grid pitch G and the number of X-ray absorbing layers per unit length, relative to each value of fG/fN, in the case of a pixel pitch Δ=125 μm;

FIG. 15 is a table of a spatial frequency fGN of the output pattern and a cycle C (a pixel number) of the output pattern, relative to each value of fG/fN;

FIG. 16 is an explanatory view showing a state of positional shifts occurring relative to each disposition example of the measurement pixels in the case of fG/fN=2/3, 8/3, and the like;

FIG. 18 is an explanatory view showing a state where positional shifts occur, in the case of fG/fN=1/2;

FIG. 19 is a table of a minimum value M of the number of the X-ray absorbing layers projected to the measurement pixel and a conditional expression of the number Q of the first measurement pixels, in the case of varying the value of fG/fN;

FIG. 25 is a block diagram of an electronic cassette that detects the start of X-ray emission.

DESCRIPTION OF THE PREFERRED EMBODIMENTS

Figure 1:
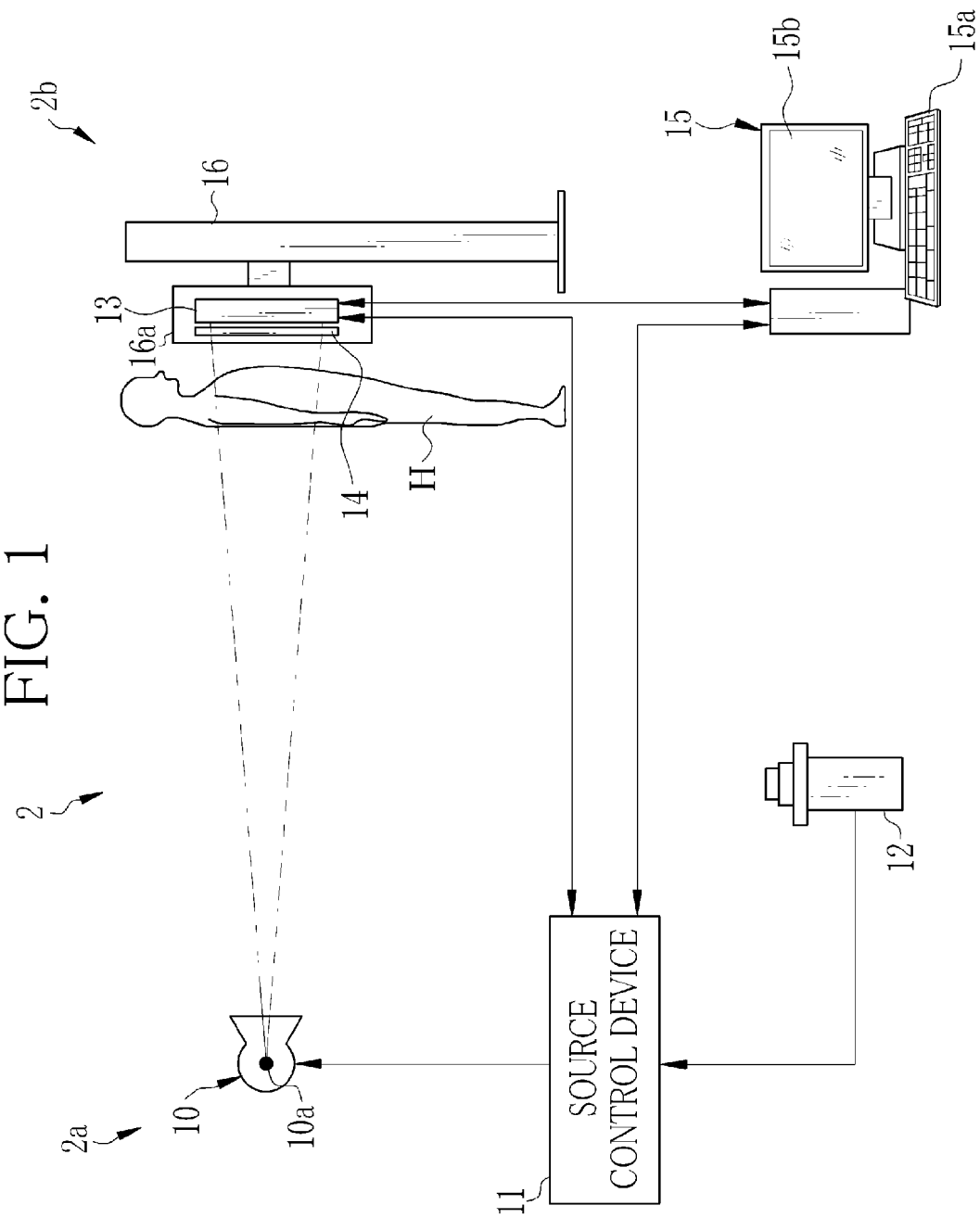
FIG. 1 is a schematic view of an X-ray imaging system.

As shown in FIG. 1, an X-ray imaging system 2 according to the present invention is constituted of an X-ray generating apparatus 2a and an X-ray imaging apparatus 2b. The X-ray generating apparatus 2a has an X-ray source 10, a source control device 11 for controlling the operation of the X-ray source 10, and an emission switch 12 for commanding the start of X-ray emission. The X-ray imaging apparatus 2b has an electronic cassette 13 for detecting X-rays passed through an object (a patient) H and outputting an X-ray image, a grid 14 for removing scattered radiation produced by the X-rays in passing through the object H, a console 15 for controlling the operation of the electronic cassette 13 and performing display processing of the X-ray image, and an imaging stand 16 for imaging the object H in a standing position. The electronic cassette 13 is used as a portable X-ray image detecting device. In addition to above, an imaging table for imaging the object H in a lying position, a source shift device for setting the X-ray source 10 in a desired orientation and position, and the like (none of them is shown in the drawing) are provided. The X-ray source 10 is used in a shared manner between the imaging stand and the imaging table.

The X-ray source 10 has an X-ray tube for radiating the X-rays and an irradiation field limiter (a collimator) for limiting an irradiation field of the X-rays. The X-ray tube has a cathode being a filament for emitting thermoelectrons, and an anode (a target) that radiates the X-rays by collision of the thermoelectrons emitted from the cathode. The X-rays radiates to every direction from a focal point 10a of the anode against which the thermoelectrons collide. The irradiation field limiter, for example, is composed of four lead plates, which block the X-rays, disposed on each side of a rectangle so as to form an irradiation opening in its middle through which the X-rays propagate. A shift of the lead plates varies the size of the irradiation opening to adjust the irradiation field.

The console 15 is wiredly or wirelessly connected to the electronic cassette 13 in a communicatable manner, and controls the operation of the electronic cassette 13 according to an input operation by an operator such as a radiological technician from an input device 15a such as a keyboard. The X-ray image is sent from the electronic cassette 13 to the console 15, and displayed on a display 15b. At the same time, the X-ray image is recorded to a storage device or a memory in the console 15, or data storage such as an image storage server connected to the console 15 through a network.

The console 15 displays an examination order, which includes information about the sex and the age of the object H, a body part to be imaged, a purpose of imaging, and the like, on the display 15b. The examination order is inputted from an external system, e.g. an HIS (hospital information system) or an RIS (radiography information system), that manages patient data and examination data related to radiography, or inputted manually by the operator from the input device 15*a*. The examination order includes the body part to be imaged e.g. head, chest, abdomen, or the like, and an imaging direction e.g. anterior, medial, diagonal, PA (the X-rays are applied from a posterior direction), AP (the X-rays are applied from an anterior direction), or the like. The operator confirms the contents of the examination order on the display 15*b*, and inputs an imaging condition corresponding to the contents of the examination order through an operation screen on the display 15*b*.

Figure 2:
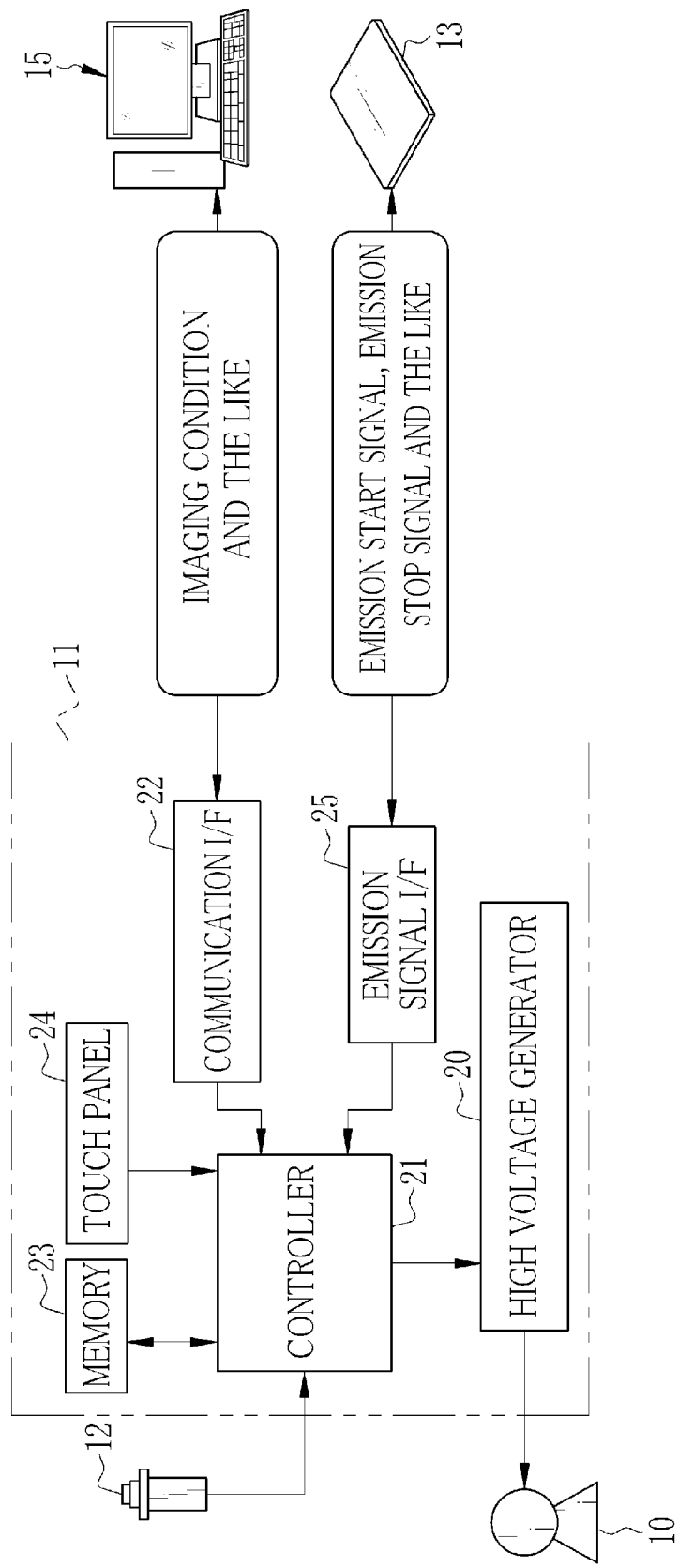
FIG. 2 is a block diagram of a source control device.

As shown in FIG. 2, the source control device 11 includes a high voltage generator 20, a controller 21, and a communication I/F 22. The high voltage generator 20 generates a high tube voltage by multiplying an input voltage by a transformer, and supplies the tube voltage to the X-ray source 10 through a high voltage cable. The controller 21 controls the tube voltage for determining an energy spectrum of the X-rays emitted from the X-ray source 10, a tube current for determining an emission amount per unit of time, and an emission time of the X-rays. The communication I/F 22 mediates transmission and reception of primary information and signals between the controller 21 and the console 15.

To the controller 21, the emission switch 12, a memory 23, and a touch panel 24 are connected. The emission switch 12 is, for example, a two-step push switch operated by the operator. Upon a first step push of the emission switch 12, a warm-up start signal is issued to start warming up the X-ray source 10. Upon a second step push, an emission start signal is issued to make the X-ray source 10 start the X-ray emission. These signals are inputted to the controller 21 through a signal cable. Upon receiving the emission start signal from the emission switch 12, the controller 21 starts supplying electric power for the X-ray emission from the high voltage generator 20 to the X-ray source 10.

The memory 23 stores several types of imaging conditions each including the tube voltage, the tube current, the emission time or a tube current-emission time product (mAs), and the like in accordance with the body part to be imaged and the like. The imaging condition is set manually by the operator through the touch panel 24. The source control device 11 controls the tube voltage and the tube current of the X-ray source 10 based on the set imaging condition, and controls a maximum driving time of the X-ray source 10. An automatic exposure control section (AEC section) 54 shown in FIG. 5 measures an X-ray dose (a time-integrated value), and stops the X-ray emission by the X-ray source 10 at the instant when the X-ray dose reaches a target dose, which is determined in accordance with the imaged body part and the like, even if the emission time or the tube current-emission time product according to the imaging condition has not elapsed. The emission time or the tube current-emission time product is set at a larger value with an allowance in the case of using the AEC section 54 than in the case of not using the AEC section 54, for the purpose of preventing a situation in which the X-ray emission is completed based on the imaging condition before the AEC section 54 stops the X-ray emission and thereby the X-ray dose becomes insufficient. For example, in the case of using the AEC section 54, a maximum emission time that is allowable under safety regulations in accordance with the body part to be imaged may be used as the emission time.

An emission signal I/F 25 is wiredly or wirelessly connected to the electronic cassette 13 in the case of using the AEC section 54. In this case, upon receiving the warm-up start signal from the emission switch 12, the controller 21 transmits an emission start request signal, which queries whether or not the X-ray emission can be started, to the electronic cassette 13 thorough the emission signal I/F 25. Upon receiving the emission start request signal, the electronic cassette 13 checks whether or not the electronic cassette 13 is ready for imaging, and transmits an emission permission signal if the electronic cassette 13 is ready for imaging. Upon receiving the emission permission signal through the emission signal I/F 25 and receiving the emission start signal from the emission switch 12, the controller 21 makes the high voltage generator 20 supply the X-ray source 10 with electric power of the high voltage to start the X-ray emission. Moreover, upon receiving an emission stop signal from the electronic cassette 13 through the emission signal I/F 25, the controller 21 stops the electric power supply from the high voltage generator 20 to the X-ray source 10 to stop the X-ray emission.

Figure 3:
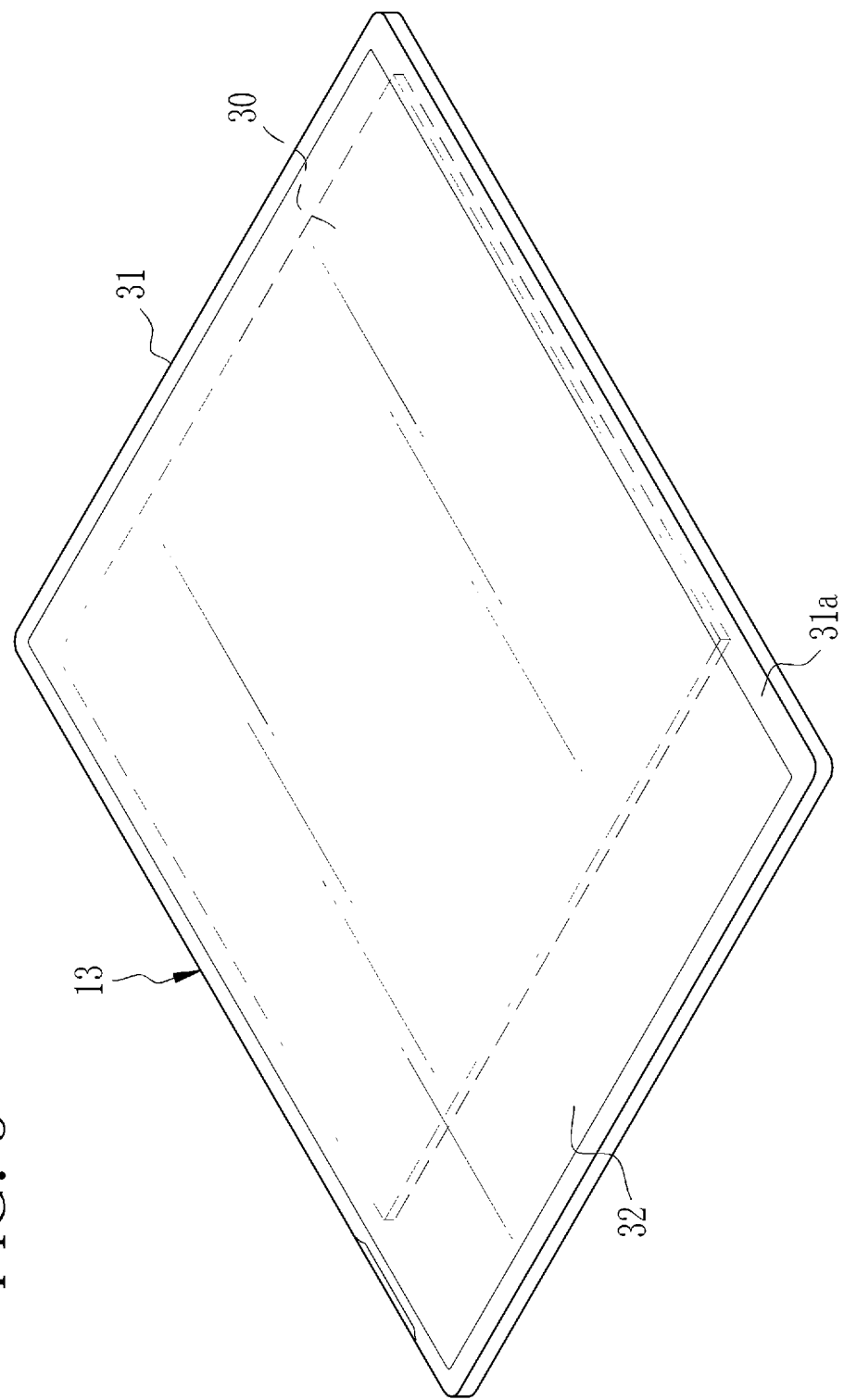
FIG. 3 is a perspective view of an electronic cassette.

In FIG. 3, the electronic cassette 13 is constituted of an image detector 30 and a portable flat box-shaped housing 31 containing the image detector 30. As the image detector 30, a well-known flat panel detector (FPD) is used. The housing 31 is made of a conductive resin, for example, and formed with a rectangular opening at its front panel 31*a* upon which the X-rays are incident. A top plate 32, which is made of an X-ray transparent material, is attached to the housing 31 so as to be fitted into the opening. The top plate 32 is made of a material of light weight, high stiffness, and high X-ray transmittance, e.g. a carbon material. The housing 31 has the function of an electromagnetic shield, which prevents entry of electromagnetic noise to the electronic cassette 13 and radiation of electromagnetic noise from the electronic cassette 13 to the outside. Note that, the housing 31 contains a battery (a secondary battery) for supplying electric power to drive the electronic cassette 13, an antenna for establishing wireless communication of data including the X-ray image and the like with the console 15, and the like.

The housing 31 adheres to the International Standard ISO 4090:2001 related to a film cassette, an IP cassette, and a CR cassette, and is of the same size as the film cassette, the IP cassette, and the CR cassette. The electronic cassette 13 is detachably set in a holder 16*a* (see FIG. 1) of the imaging stand 16 or a holder of the imaging table, and held in such a position that an imaging area 41 (see FIG. 5) is opposed to the X-ray source 10. The X-ray source 10 is shifted by the source shift device attached to a ceiling of an imaging room or the like, in accordance with the imaging stand or the imaging table to be used. The electronic cassette 13 is sometimes used by itself in a state of being put on a bed under the object H lying or held by the object H himself/herself, instead of being set in the imaging stand 16 or the imaging table. Also, the electronic cassette 13 is compatible with the film cassette, the IP cassette, and the CR cassette, and can be mounted on an existing imaging stand or table designed for the film cassette, the IP cassette, and the CR cassette.

Figure 4:
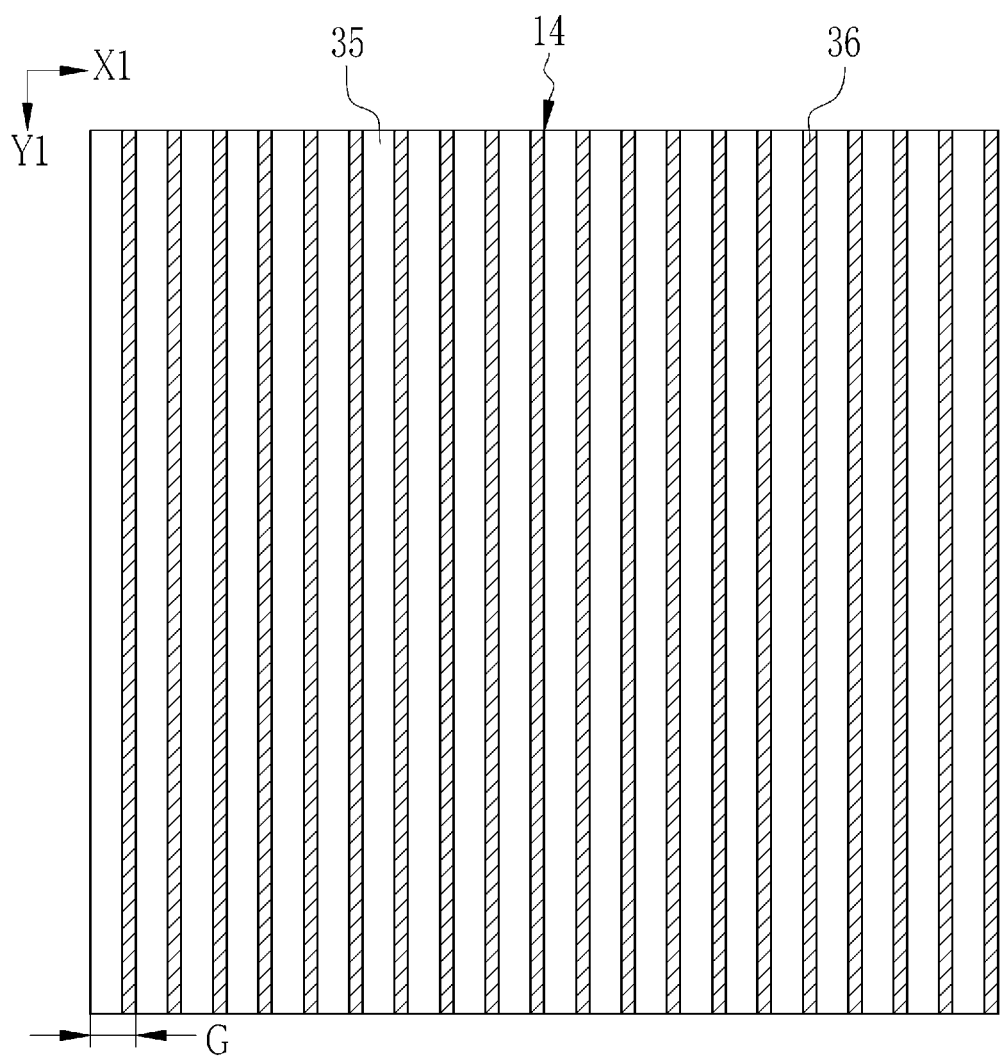
FIG. 4 is a plan view of a grid.

In FIG. 4, the grid 14 is made of a thin plate of approximately the same size as the housing 31. The grid 14 is detachably loaded to the holder 16*a* so as to be disposed in front of the electronic cassette 13 (see FIG. 1). The grid 14 can be exchanged for another grid in accordance with the purpose of imaging, or detached from the holder 16*a* in imaging without using the grid. The holder 16*a* has no mechanism for swinging the grid 14, and therefore the grid 14 is a so-called static grid, which does not swing.

In this embodiment, the grid 14 is directly inserted into the holder 16*a*. However, the grid 14 may be contained in an X-ray transparent housing to protect the grid 14, and the housing may be loaded into the holder 16a. Otherwise, the grid 14 may be provided within the housing 31 in manufacturing the electronic cassette 13, instead of providing the grid 14 separately from the electronic cassette 13. Otherwise, a grid holder may be provided on the front panel 31a of the housing 31 of the electronic cassette 13, and the grid 14 may be detachably attached to the grid holder. Also in this case, the grid 14 can be exchanged or detached in X-ray imaging in accordance with the purpose of imaging.

The grid 14 has strip-shaped X-ray transparent layers 35 and X-ray absorbing layers 36 (shown with hatching) extending in a Y1 direction (a first direction). A plurality of the layers 35 and 36 are arranged alternately in an X1 direction (a second direction) orthogonal to the Y1 direction at a predetermined grid pitch (an arrangement pitch of the X-ray absorbing layers 36) G. The X-ray transparent layer 35 is made of an X-ray transparent material such as aluminum, or a gap. The X-ray absorbing layer 36 is made of a material that absorbs the X-rays and blocks the X-rays from transmitting, such as lead, a molybdenum alloy, or a tantalum alloy. The grid 14 is set in the holder 16a such that the arrangement direction X1 of each layer 35, 36 coincides with a row direction X2 (see FIG. 5) of pixels 40 of the image detector 30.

The number of the X-ray absorbing layers 36 in the arrangement direction X1 per unit length is 32/cm to 100/cm, for example. Thus, the grid pitch G is 100 μm to approximately 300 μm.

Figure 5:
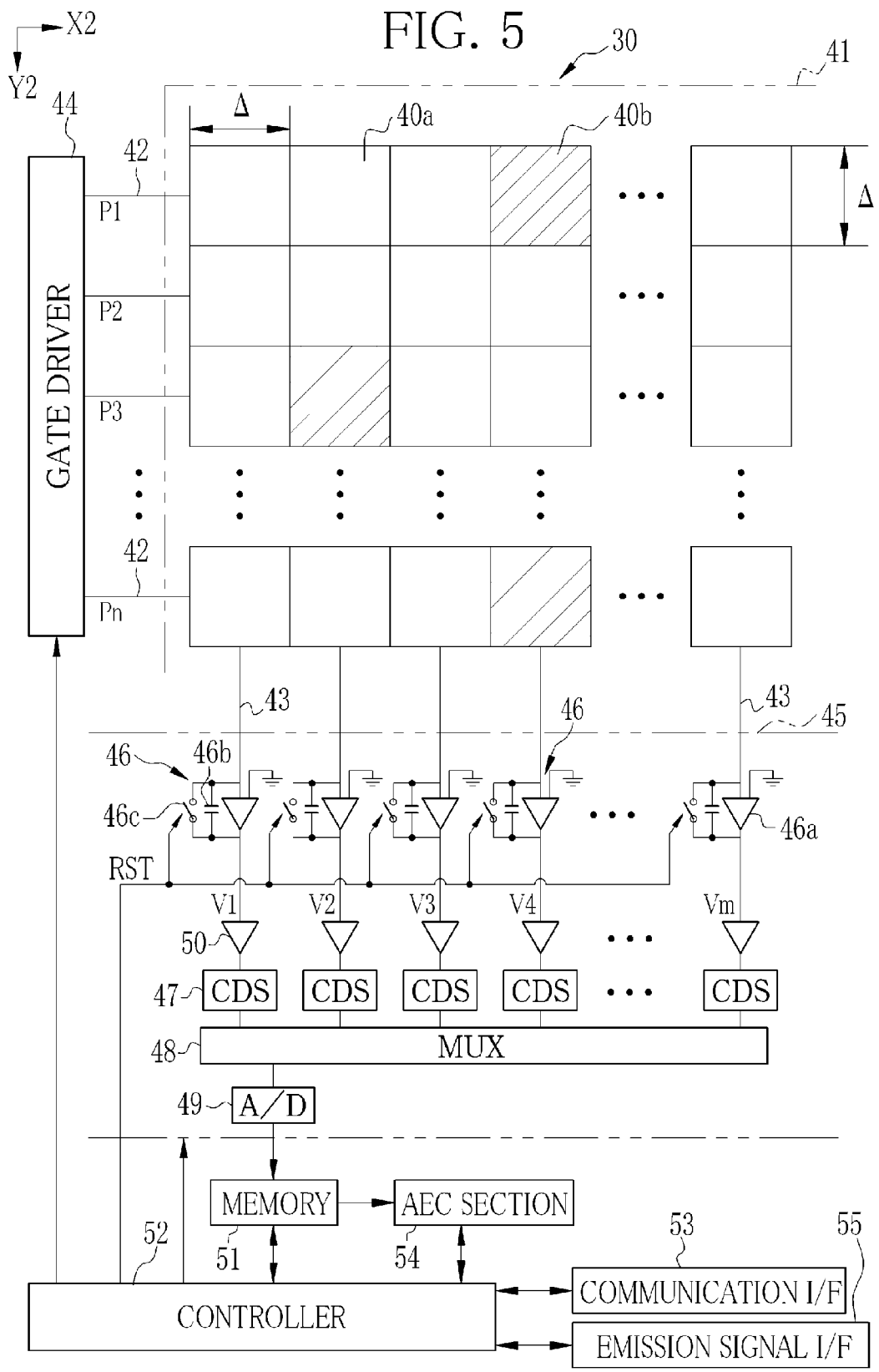
FIG. 5 is a block diagram showing the structure of the electronic cassette.

In FIG. 5, the image detector 30 has a TFT active matrix substrate (not shown), and the imaging area 41 is formed on this substrate. The imaging area 41 is provided with a plurality of pixels 40, which produce electric charge in accordance a received X-ray dose, arrayed into a matrix of n rows (along the X2 direction)×m columns (along the Y2 direction) at a predetermined pitch Δ (100 μm to 200 μm, for example).

The image detector 30 is, for example, of an indirect conversion type having a scintillator (not shown) made of a phosphor. In the image detector 30, the pixels 40 perform photoelectric conversion of visible light converted by the scintillator. As is widely known, the scintillator is made of CsI:Tl (thallium activated cesium iodide), GOS ($Gd_2O_2S$:Tb terbium activated gadolinium oxysulfide), or the like, and is opposed to the entire imaging area 41 having an array of the pixels 40. Note that, the scintillator and the TFT active matrix substrate may adopt either a PSS (penetration side sampling) method in which the scintillator and the substrate are disposed in this order from an X-ray incident side, or an ISS (irradiation side sampling) method in which the substrate and the scintillator are disposed in this order. Instead of above, the image detector 30 may be of a direct conversion type, which uses a conversion layer (amorphous selenium or the like) for directly converting the X-rays into the electric charge without using the scintillator.

As is widely known, the pixel 40 is provided with a photoelectric converter for producing the electric charge (electron and positive hole pairs) by the entry of the visible light, and the TFT being a switching element (none of them is illustrated). Note that, since space between the pixels 40 is omitted in FIG. 5, a pixel pitch Δ represents the width of the pixels 40. However, the pixel pitch Δ is the distance between the centers of the photoelectric converters of the two pixels 40 adjacent to each other.

The pixels 40 include normal pixels 40a and measurement pixels 40b. The normal pixels 40a are used to detect the X-ray image, and the electric charge accumulated in the normal pixels 40a is read out after the completion of X-ray imaging. The measurement pixels 40b are used to measure the X-ray dose, and the electric charge is taken out of the measurement pixels 40b during the X-ray imaging. The measurement pixels 40b function as dose measurement sensors, which measure the X-ray dose received by the imaging area 41, and are used for AEC, for example. Note that, the measurement pixels 40b are hatched so as to make distinction from the normal pixels 40a.

First, the structure of the normal pixel 40a will be described. As is widely known, the photoelectric converter has a semiconducting layer (of a PIN (p-intrinsic-n) type, for example) for producing the electric charge, and upper and lower electrodes disposed on the top and bottom of the semiconducting layer. The lower electrode is connected to the TFT, and the upper electrode is connected to a bias line. The number of the bias lines coincides with the number of rows (n rows) of the normal pixels 40a. These bias lines are connected to a bias power source through one bus. Since application of a bias voltage produces an electric field in the semiconducting layer, the electric charge (electron and positive hole pairs) produced in the semiconducting layer by the photoelectric conversion is attracted to the upper and lower electrodes, one of which has positive polarity and the other has negative polarity, and thereby the electric charge is accumulated in the photoelectric converter.

A gate electrode of the TFT is connected to a scan line 42. A source electrode of the TFT is connected to a signal line 43. A drain electrode of the TFT is connected to the photoelectric converter. The scan lines 42 are wired in a row direction, and the signal lines 43 are wired in a column direction. Since one scan line 42 is assigned to the pixels 40 of one row, the total number of the scan lines 42 coincides with the number of the rows (n rows) of the pixels 40. Likewise, since one signal line 43 is assigned to the pixels 40 of one column, the total number of the signal lines 43 coincides with the number of the columns (m columns) of the pixels 40. Each scan line 42 is connected to a gate driver 44, and each signal line 43 is connected to a signal processing circuit 45.

The gate driver 44 performs an accumulation operation for accumulating the signal charge in the normal pixels 40a in accordance with the received X-ray dose, a readout (actual reading) operation for reading out the accumulated signal charge from the normal pixels 40a, and a reset (idle reading) operation, by driving the TFTs under control by a controller 52. In the accumulation operation, the TFTs are in an off state, and the signal charge produced during that time is accumulated in the normal pixels 40a. The readout operation is carried out immediately after X-ray imaging. In this readout operation, the gate driver 44 sequentially issues gate pulses P1 to Pn at predetermined intervals to activate the scan lines 42 one by one in a sequential manner. Thus, the TFTs of one row connected to the activated scan line 42 are turned into an on state. Upon turning on the TFTs, the electric charge accumulated in the normal pixels 40a is read out to the signal lines 43 and sent to the signal processing circuit 45.

The measurement pixel 40b is used for measuring the X-ray dose, and has the same fundamental structure including the photoelectric converter and the like as the normal pixel 40a. However, in the measurement pixel 40b, the source electrode and the drain electrode of the TFT are shorted out. Thus, the electric charge produced by the photoelectric converter of the measurement pixel 40b flows into the signal line 43, irrespective of the turn-on and -off of the TFT. Therefore, it is possible to take out the signal charge from the measurement pixel 40b, even if the normal pixels 40a in the same row have the TFTs being turned off and are in the accumulation operation of the signal charge.

The signal processing circuit 45 includes integrating amplifiers 46, amplifiers 50, and CDS circuits (CDSs) 47 provided to signal lines 43 on a one-to-one basis, and a multiplexer (MUX) 48 and an A/D converter (A/D) 49 used in a shared manner among the signal lines 43. The integrating amplifier 46 is composed of an operational amplifier 46a and a capacitor 46b connected between input and output terminals of the operational amplifier 46a, and the signal line 43 is connected to one of the input terminals of the operational amplifier 46a. The other input terminal of the operational amplifier 46a is connected to a ground (GND). A reset switch 46c is connected in parallel with the capacitor 46b. The CDS 47, having a sample hold circuit, applies correlated double sampling to an output voltage signal of the integrating amplifier 46 to remove noise, and holds (sample-holds) the voltage signal of the integrating amplifier 46 for a predetermined time period at the sample hold circuit. The MUX 48 chooses one of the CDSs 47, which are provided on a column-by-column basis and connected in parallel, in turn with the use of an electronic switch based on an operation control signal from a shift register (not shown). The voltage signals of the chosen CDSs 47 are inputted in series to the A/D 49. The A/D 49 converts the voltage signals into digital voltage signals, and outputs the digital voltage signals to a memory 51 as image data of one row. Note that, another amplifier may be connected between the MUX 48 and the A/D 49.

In the readout operation of the normal pixels 40a, the integrating amplifiers 46 integrate the signal charge that is taken out of the normal pixels 40a of the activated row through the signal lines 43, and convert the signal charge into analog voltage signals V1 to Vm. Each of the voltage signals V1 to Vm of the integrating amplifiers 46 is amplified by the amplifier 50 and sent to the CDS 47. After the noise removal by the CDS 47, the voltage signals V1 to Vm are taken out in turn by the MUX 48 and converted into the digital data by the A/D 49. The memory 51 records the image data associated with the coordinates of the normal pixels 40a on a row-by-row basis.

During X-ray imaging, the signal charge produced in the measurement pixels 40b flows into the integrating amplifiers 46 through the signal lines 43. Provided that there are a plurality of measurement pixels 40b in the same column, the capacitor 46b integrates the electric charge of the measurement pixels 40b. The integrating amplifiers 46 are reset at regular time intervals, and thus a plurality of number of measurements are carried out. Output voltages of the integrating amplifiers 46 are taken out whenever the measurement is performed, and converted into digital voltage signals (hereinafter called dose measurement signals) by the A/D 49. The dose measurement signals are sent to the memory 51 as measurement values. Accordingly, the measurement values, which are recorded to the memory 51 in associated with the coordinate information of each measurement pixel 40b in the imaging area 41, are updated at predetermined time intervals.

In the pixels 40 (both of the normal pixels 40a and the measurement pixels 40b), dark charge occurs in the semiconducting layer of the photoelectric converter irrespective of the presence or absence of the entry of the X-rays. Due to the application of the bias voltage, the dark charge is accumulated in the photoelectric converter of each pixel 40. The dark charge occurring in the pixels 40 becomes a noise component of the image data, and therefore the reset operation is performed at predetermine time intervals to remove the noise component. The reset operation is an operation in which the dark charge produced in the pixels 40 is discharged through the signal lines 43.

The reset operation adopts a sequential reset method, for example, by which the pixels 40 are reset on a row-by-row basis. In the sequential reset method, just as with the readout operation of the signal charge, the gate driver 44 sequentially issues gate pulses P1 to Pn at predetermined intervals to the scan lines 42 to turn on the TFTs of the pixels 40 on a row-by-row basis. While the TFT is turned on, the dark charge flows from the pixel 40 through the signal line 43 into the capacitor 46b of the integrating amplifier 46. In the reset operation, in contrast to the readout operation, the MUX 48 does not read out the electric charge accumulated in the capacitors 46b. In synchronization with the issue of each of the gate pulses P1 to Pn, the controller 52 outputs a reset pulse RST to turn on the reset switches 46c. Thereby, the electric charge accumulated in the capacitors 46b is discharged, and the integrating amplifiers 46 are reset.

Instead of the sequential reset method, a parallel reset method in which a plurality of rows of pixels are grouped together and the sequential reset is carried out in each group so as to concurrently discharge the dark charge from the rows of the number of groups, or all pixels reset method in which the gate pulse is inputted to every row to discharge the dark charge from every pixel at a time may be used. The parallel reset method and the all pixels reset method allow speeding up the reset operation.

The controller 52 is provided with various image processing circuits (not shown) that apply an offset correction, a sensitivity correction, and a defect correction to the X-ray image data of the memory 51. The offset correction circuit subtracts an offset correction image, which is captured by the image detector 30 without applying the X-rays, from the X-ray image to remove fixed pattern noise caused by the individual difference of the signal processing circuit 45 or an imaging environment. The sensitivity correction circuit, which is also called gain correction circuit, corrects sensitivity variations in the photoelectric converter of each pixel 40, variations in the output properties of the signal processing circuit 45, and the like. The defect correction circuit performs linear interpolation of a pixel value of a defect pixel with a pixel value of a normal pixel in the vicinity thereof, based on defect pixel information produced in shipping or a routine check. In the defect correction circuit, the measurement pixel 40b is treated as a defect pixel. Since an output of the measurement pixel 40b that constantly flows out affects pixel values of the normal pixels 40a in the same column as the measurement pixel 40b, the defect correction circuit applies the defect correction by the linear interpolation to the pixel values of the normal pixels 40a in the same column as the measurement pixel 40b too. Note that, the above-described various image processing circuits may be provided in the console 15, and the console 15 may perform the various types of image processing.

Whenever one measurement of the X-ray dose is carried out, the controller 52 reads out the dose measurement signals (the measurement values) obtained in this measurement and integrated measurement values (integrated X-ray doses) until the last measurements from the memory 51, and calculates new integrated measurement values by integration on a measurement pixel 40b basis, and overwrites the new integrated measurement values to the memory 51. The AEC section 54 takes out the integrated measurement values of all or part of the measurement pixels 40b included in a measurement area, and obtains an average value (an average integrated X-ray dose) by an arithmetic average. At the instant when the obtained average value reaches an emission stop threshold value (a target dose), the emission stop signal is produced. This emission stop signal is outputted from an emission signal I/F 55 through the controller 52. To the emission signal I/F 55, the emission signal I/F 25 of the source control device 11 is connected wiredly or wirelessly. The emission signal I/F 55 performs reception of the emission start request signal, transmission of the emission permission signal in response to the emission start request signal, reception of the emission start signal, and transmission of the emission stop signal outputted from the AEC section 54.

Next, the operation of the X-ray imaging system 2 will be described. Before performing X-ray imaging, preparations for the imaging are performed. First, the electronic cassette 13 is loaded into the imaging stand or the imaging table, e.g. the holder 16a of the imaging stand 16. In imaging using a grid, the grid 14 is loaded into the holder 16a to dispose the grid 14 in front of the electronic cassette 13. With referring to the examination order displayed on the display 15b, the imaging condition including the tube voltage, the tube current, the emission time, the body part to be imaged, and the like is inputted with operation of the touch panel 24 or the like. Then, the object H is made stand in front of the imaging stand 16, and the measurement area is set in accordance with the body part to be imaged. For example, in a case where the body part to be imaged of the object H is a chest, areas corresponding to left and right lung fields in the imaging area 41 are designated as the measurement areas. The completion of the preparations for the imaging enables the X-ray imaging.

The electronic cassette 13 loaded into the holder 16a is set in a standby mode. In the standby mode, the dark charge is produced in each pixel 40 of the image detector 30, even though the X-rays are not applied thereto. To remove the dark charge being the noise component, the reset operation is applied at predetermined time intervals to the image detector 30 during the preparations for the X-ray imaging (before the X-ray imaging). In the reset operation, the gate driver 44 sequentially issues the gate pulses P1 to Pn to the scan lines 42 so as to turn on the TFTs of the normal pixels 40a on a row-by-row basis. Upon turning on the TFTs of the normal pixels 40a of one row, the dark charge accumulated in these normal pixels 40a is read out and sent to the integrating amplifiers 46. In the reset operation, the MUX 48 does not take out the voltage converted by the integrating amplifiers 46.

In the reset operation, the controller 52 outputs the reset pulse RST with a predetermined time difference from each of the gate pulses P1 to Pn. Since the reset pulse RST turns on the reset switches 46c, the dark charge accumulated in each capacitor 46b is discharged so as to reset the integrating amplifiers 46. As for the measurement pixels 40b, the dark charge flows into the integrating amplifiers 46 irrespective of each of the gate pulses P1 to Pn, because the TFTs are shorted out. Thus, the dark charge from the measurement pixels 40b is discarded together with the dark charge of the normal pixels 40a. Note that, the reset switches 46c may be kept in an on state during the reset operation.

After the preparations for the X-ray imaging, the X-ray source 10 is warmed up by a first step push of the emission switch 12. Then, the emission start signal is issued by a full push of the emission switch 12. This emission start signal is inputted to the controller 21 of the source control device 11, so that the X-ray imaging is started. The emission start signal is also inputted to the electronic cassette 13 through the emission signal I/F 25. The electronic cassette 13 is changed from the standby mode to an imaging mode, and the image detector 30 is shifted from the reset operation to the accumulation operation. Concurrently with this, automatic exposure control is started based on a dose measurement using the measurement pixels 40b.

Upon starting the X-ray imaging, the X-ray source 10 is actuated by the high voltage from the high voltage generator 20. The X-ray source 10 emits and applies the X-rays to the body part to be imaged of the object H. The X-rays passed through the body part are incident upon the grid 14. The grid 14 blocks the X-rays at the X-ray absorbing layers 36, while passes the X-rays at the X-ray transparent layers 35. The X-rays passed through the X-ray transparent layers 35 are incident upon the electronic cassette 13. The X-rays that are incident upon the electronic cassette 13 are converted into the visible light at the image detector 30. This visible light is converted into the electric charge at the photoelectric converter of each pixel 40. During the accumulation operation of the image detector 30, the TFTs are in an off state, and thus each of the normal pixels 40a accumulates the produced electric charge in the photoelectric converter.

Since the TFTs of the measurement pixels 40b are shorted out, the electric charge produced in the photoelectric converters of the measurement pixels 40b flows into the signal lines 43, irrespective of the turn-on and -off of the TFTs, during the accumulation operation of the image detector 30. Thus, the electric charge of each measurement pixel 40b is accumulated in the capacitor 46b of the corresponding integrating amplifier 46. The reset switch 46c of each integrating amplifier 46 is usually turned off, but turned on once every regular time period to reset the integrating amplifiers 46. The time duration of the turn-off of the reset switches 46c after the turn-on is designated as one measurement period, and the X-ray dose per predetermined time is measured. The X-rays are measured in relatively short cycles, and the X-ray dose is measured on a measurement pixel 40b basis by integrating a measurement value of each measurement. Note that, the reset switch 46c of the integrating amplifier 46 may be kept in an off state and a voltage of each integrating amplifier 46 may be read out in relatively short cycles. This allows taking out an integrated measurement value in each cycle, and hence eliminates the need for integrating the measurement value of each measurement.

In a first measurement, an output voltage of the integrating amplifier 46 is multiplied by the amplifier 50 and sent to the CDS 47. This CDS 47 samples the output voltage of the integrating amplifier 46 at the start and the end of one measurement, and calculates the difference therebetween to remove noise. The output voltage of each CDS 47 is sequentially taken out by the MUX 48 and sent to the A/D 49. The A/D 49 converts the output voltage into digital data, and the digital data is sent to the memory 51 as the dose measurement signal per predetermined time. The memory 51 records each dose measurement signal associated with the coordinate information of the measurement pixel 40b to a first memory area as a measurement value of the first measurement.

The AEC section 54 chooses a minimum unit of the measurement pixels 40b (called a group of the measurement pixels 40b) that are included in the designated measurement area. In the minimum unit, the effect of a positional shift of the grid 14 can be compensated even if the positional shift of the grid 14 occurs. This group of the measurement pixels 40b may contain one measurement pixel 40b, or a plurality of measurement pixels 40b situated in different positions in the measurement area. Furthermore, all the measurement pixels 40b included in the designated measurement area may be designated as the chosen measurement pixels for use in the automatic exposure control.

The AEC section 54 calculates an average value of the measurement values of the chosen measurement pixels. Then, the AEC section 54 compares the calculated average value with the predetermined emission stop threshold value. In a case where the average value does not reach the emission stop threshold value, a second measurement of the X-ray dose is performed in synchronization with the operation of the reset switches 46c. Note that, instead of the average value, a sum value of the measurement values may be calculated and the sum value may be compared with another emission stop threshold value that is set in accordance with the sum value.

In the second measurement of the X-ray dose, just as with the first measurement, the output voltages of the integrating amplifiers 46 are taken out and sent to the memory 51 as second measurement values. The second measurement values are recorded to a second memory area in associated with the coordinate information of the measurement pixels 40b. After the recording, the controller 52 adds the second measurement value to the first measurement value recorded in the first memory area on a measurement pixel-by-measurement pixel basis, and updates the measurement value of the first memory area with an obtained integrated measurement value (integrated X-ray dose). After the update, the AEC section 54 reads out the integrated measurement value of each of the chosen measurement pixels from the first memory area, and calculates an average value thereof. The AEC section 54 compares the calculated average value with the emission stop threshold value. In a case where the average value according to the second measurement does not reach the emission stop threshold value, a third measurement of the X-ray dose is performed in the procedure described above.

In a case where the average value of the integrated measurement values reaches the emission stop threshold value while repeating the measurements of the X-ray dose, the AEC section 54 judges that appropriate exposure is carried out. In this case, the controller 52 sends the emission stop signal to the source control device 11 through the emission signal I/F 55. Upon receiving the emission stop signal from the electronic cassette 13, the source control device 11 stops the operation of the high voltage generator 20. Thereby the X-ray source 10 stops the X-ray emission and completes the X-ray imaging.

After the electronic cassette 13 commands the source control device 11 to complete the X-ray imaging, the image detector 30 starts the readout operation. At the start of the readout operation, every reset switch 46c is turned on and every integrating amplifier 46 is reset. Thus, the electric charge is discharged from the measurement pixels 40b. Then, after every reset switch 46c is turned off, the gate driver 44 issues the gate pulse P1 for the first row. This gate pulse P1 activates the scan line 42 of the first row, and turns on the TFTs connected thereto. Upon turning on the TFTs, the electric charge accumulated in the normal pixels 40a of the first row flows into the integrating amplifiers 46 through the signal lines 43. The integrating amplifiers 46 convert the signal charge of each normal pixel 40a into voltages. The voltages are recorded to the memory 51 as the X-ray image data of the first row through the amplifiers 50, the CDSs 47, the MUX 48, and the A/D 49.

After the image data of the first row is written to the memory 51, the controller 52 outputs the reset pulse RST to the integrating amplifiers 46 to turn on and off the reset switches 46c. Thus, the signal charge accumulated in each capacitor 46c is discharged. After the reset of the integrating amplifiers 46, the gate driver 44 outputs the gate pulse P2 of the second row to start reading out the signal charge from the normal pixels 40a of the second row. The X-ray image data of the second row obtained in this manner is written to the memory 51.

In a like manner, the gate driver 44 sequentially issues the third to n-th gate pulses P3 to Pn to read out the electric charge from the normal pixels 40a of the third to n-th rows. The electric charge is converted into the X-ray image data of the third to n-th rows, and written to the memory 51.

The controller 52 applies various types of image processing including the offset correction, the sensitivity correction, and the defect correction to the X-ray image written to the memory 51. The offset correction eliminates fixed pattern noise caused by the individual difference of the signal processing circuit 45 or an imaging environment. The sensitivity correction corrects sensitivity variations in the photoelectric converter of each normal pixel 40a, variations in the output properties of the signal processing circuit 45, and the like. The defect correction performs linear interpolation of the defect pixel identified beforehand, the measurement pixel 40b, and the normal pixels 40a arranged in the same column as the measurement pixel 40b, with the use of the pixel values in the vicinity thereof.

The X-ray image that is recorded to the memory 51 after being subjected to the image processing is sent from the electronic cassette 13 through a communication I/F 53 to the console 15. In this console 15, the X-ray image is displayed on the display 15b and used in a medical diagnosis. The X-ray image sent to the console 15 is saved to the storage device in the console 15 or the image storage server connected to the console 15 through the network.

Imaging without using the grid is the same as the imaging with using the grid, except that the grid 14 is removed from the imaging stand or the imaging table. The dose measurement signals obtained in the imaging without using the grid are larger than those obtained in the imaging with using the grid, because none of the measurement pixels 40b is subjected to X-ray absorption by the grid 14. Accordingly, the emission stop threshold value (the target value) is set higher in the imaging without using the grid than in the imaging with using the grid, in order to equalize an X-ray irradiation amount (an exposure amount) of the object H between the imaging with using the grid and the imaging without using the grid.

In the above embodiment, the emission stop signal is issued at the instant when the average value of the integrated measurement values of the measurement pixels 40b reaches the emission stop threshold value. Instead of this, predicted time of reaching the target dose may be calculated from X-ray intensity (an X-ray dose per unit of time), and the emission stop signal may be sent to the source control device 11 when the calculated predicted time has elapsed. Note that, information on the predicted time itself may be sent to the source control device 11, and the X-ray source 10 may stop the X-ray emission when the source control device 11 detects the elapse of the predicted time.

The type and the like of the grid 14 have an effect on the measurement of the X-ray dose. Therefore, by performing pre-imaging in which the a low X-ray dose is applied to the object, the emission time or the tube current-emission time product for actual X-ray imaging may be determined based on the measurement of the X-ray dose in the pre-imaging.

The electronic cassette 13 and the grid 14 are sometimes set in the imaging stand or the imaging table in a state of being shifted from a designed positional relation. Otherwise, while the electronic cassette 13 and the grid 14 are loaded into the imaging stand or the imaging table, the positional relation between the electronic cassette 13 and the grid 14 is sometimes changed by vibration or the like. The present invention reduces variation in the measurement value of the measurement pixel so as to eliminate the effect of the shift in the positional relation between the electronic cassette 13 and the grid 14 on the measurement of the X-ray dose by devising an arrangement of the measurement pixels. Arrangement examples of the measurement pixels that allow reducing the variation in the measurement value will be hereinafter described.

FIGS. 6 to 12 show a pixel array that is a part of one row of the pixels 40 of the image detector 30 shown in FIG. 5. The reference number "400" is assigned to the pixel array, and the reference number "40" is assigned to the pixels just as with FIG. 4. FIGS. 6 to 12 show the positional relation between each of the pixels 40 and the X-ray absorbing layers 36, a pattern of the number (hereinafter called number pattern) of the X-ray absorbing layers 36 projected to the pixels 40 in capturing a stripe-patterned image of the grid 14 corresponding to each of the layers 35 and 36 without disposing the object H, and a pattern (hereinafter called output pattern) of the voltage signal measured by each pixel 40, which varies depending on the positional relation and the number pattern, in the case of variously changing the grid pitch G and the pixel pitch Δ.

Figure 6:
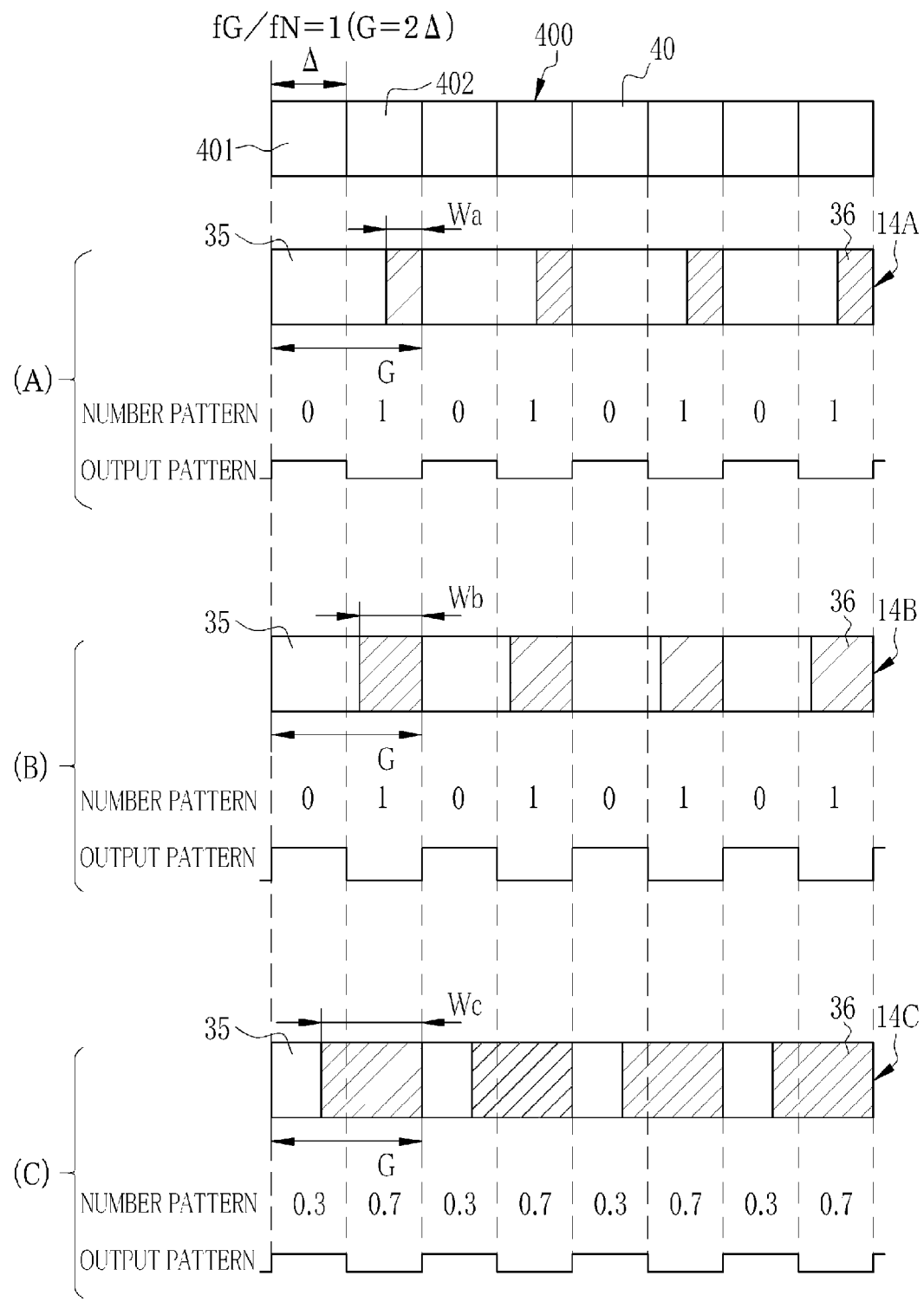
FIG. 6 is an explanatory view of an output waveform from each pixel in a case where the ratio fG/fN between a grid frequency fG and a Nyquist frequency fN of the pixels is 1.

In grids 14A to 14C of FIG. 6, a grid pitch G is twice as large as the pixel pitch Δ (G=2Δ). Since the grid pitch G is twice as large as the pixel pitch Δ, the two pixels 40 are present within the grid pitch G. Among (A) to (C) of FIG. 6, the widths Wa, Wb, and Wc of the X-ray absorbing layer 36 are different from each other (Wa<Wb<Wc). The widths Wa and Wb are equal to or narrower than the pixel pitch Δ, and the width Wc is wider than the pixel pitch Δ.

According to (A) and (B) of FIG. 6, for example, a leftmost pixel 401 is opposed to no X-ray absorbing layer 36, so the number of the X-ray absorbing layers 36 projected to the leftmost pixel 401 is zero. On the other hand, a pixel 402 next to the leftmost pixel 401 on the right side is opposed to one X-ray absorbing layer 36, so the number of the X-ray absorbing layers 36 projected to the pixel 402 is one. In the pixel array 400, the pixels 40 to which no X-ray absorbing layer 36 is projected and the pixels 40 to which one X-ray absorbing layer 36 is projected are arranged alternately and repeatedly. An integrated X-ray dose received by the pixel 40 to which one X-ray absorbing layer 36 is projected is relatively lower than that received by the pixel 40 to which no X-ray absorbing layer 36 is projected. Thus, the pixel 40 to which one X-ray absorbing layer 36 is projected has a relatively low output level of the voltage signal. Accordingly, the output pattern has a repetition of "high" voltage signals at a relatively high output level and "low" voltage signals at a relatively low output level in two pixel cycles.

Since the grid 14B of FIG. 6 (B) has the wider X-ray absorbing layers 36 than the grid 14A of FIG. 6 (A) has (Wb>Wa), the pixels 40 to which one X-ray absorbing layer 36 is projected output a lower level of the voltage signals in FIG. 6 (B) than in FIG. 6 (A). Thus, the difference between the voltage signals "high" and "low" is larger in FIG. 6 (B) than in FIG. 6 (A). Nevertheless, in the case of FIG. 6 (B), since the width Wb of the X-ray absorbing layers 36 is equal to or narrower than the pixel pitch Δ just as in the case of FIG. 6 (A), the number of the X-ray absorbing layers 36 projected to the pixel 40 repeats zero and one in two pixel cycles, and the voltage signals "high" and "low" are repeated in two pixel cycles in the output pattern.

In the grid 14C of FIG. 6 (C), since the width Wc of the X-ray absorbing layers 36 is wider than the pixel pitch Δ, the X-ray absorbing layer 36 is concurrently projected to two pixels 40 next to each other. The leftmost pixel 401 is opposed to a part, for example, 0.3 X-ray absorbing layers 36. On the other hand, the pixel 402 next to the leftmost pixel 401 on the right side is opposed to the remaining 0.7 X-ray absorbing layers 36. The pixel 402 opposed to 0.7 X-ray absorbing layers 36 receives a relatively lower X-ray dose than the pixel 401 opposed to 0.3 X-ray absorbing layers 36, and hence the voltage signal of the pixel 402 is lower than that of the pixel 401. Thus, the output pattern repeats "high" and "low" in two pixel cycles. The number pattern is "0.3, 0.7, 0.3, 0.7, . . . ", in contrast to "0, 1, 0, 1, . . . " of FIGS. 6 (A) and (B). However, FIG. 6 (C) is the same as FIGS. 6 (A) and (B) in terms of repeating a state of projecting a low number of X-ray absorbing layers 36 to the pixel 40 and a state of projecting a high number of X-ray absorbing layers 36 to the pixel 40 in two pixel cycles, and also in terms of repeating "high" and "low" in two pixel cycles in the output pattern.

In the cases of (A) to (C) of FIG. 6, the grid pitch G and the pixel pitch Δ are constant throughout the entire row. Therefore, even if the pixels 40 are shifted relative to the grids 14A to 14C by one pixel in the row direction X2, the pixels 40 opposed to the X-ray absorbing layers 36 are shifted by one pixel and the number pattern and the output pattern are not changed. The same goes if how many pixels the pixels 40 are shifted by. Also, even if the pixels 40 are shifted by an amount less than one pixel such as 0.5 pixels, instead of one pixel, peak periodicity produced by "0" and "1" of the number pattern and "high" and "low" of the output pattern is the same as before the shift, though the number of the X-ray absorbing layers 36 projected to the pixel 40 and the output level themselves change.

Figure 7:
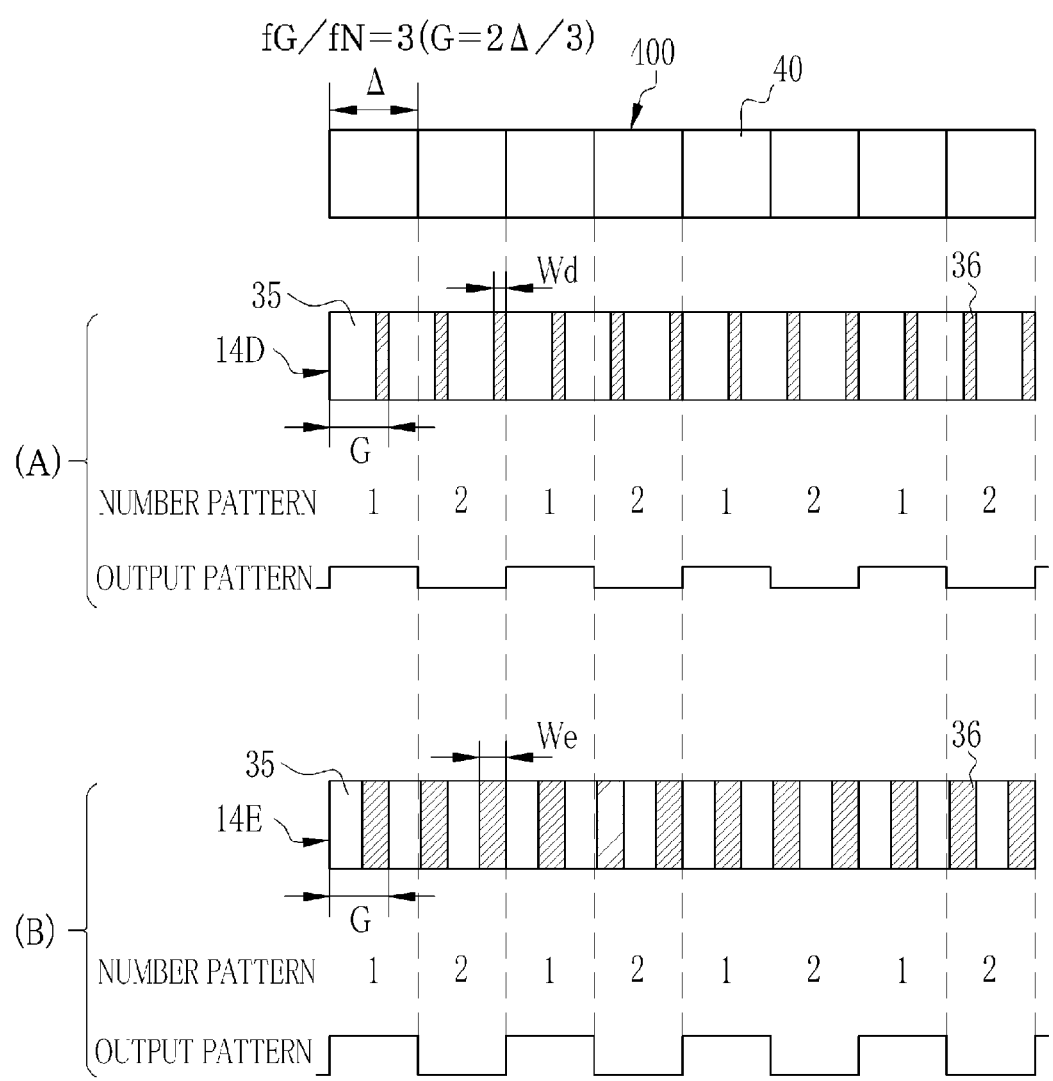
FIG. 7 is an explanatory view similar to FIG. 6 in the case of fG/fN=3.

FIG. 7 shows a case where a grid pitch G is ⅔ of the pixel pitch Δ (G=2Δ/3). The width Wd of the X-ray absorbing layers 36 of a grid 14D shown in FIG. 7 (A) is different from the width We of the X-ray absorbing layers 36 of a grid 14E shown in FIG. 7 (B). These widths Wd and We are set at such values that the X-ray absorbing layer 36 is not concurrently projected to two pixels 40 next to each other. Using these grids 14D and 14E brings about an alternate arrangement of pixels to which one X-ray absorbing layer 36 is projected and pixels to which two X-ray absorbing layers 36 are projected. Accordingly, in either of FIGS. 7 (A) and (B), the number pattern is "1, 2, 1, 2, . . . ". The output pattern is "high, low, high, low, . . . ", just as with FIG. 6.

The grids 14D and 14E have the X-ray absorbing layers 36 whose widths do not straddle two pixels. However, even if the X-ray absorbing layers 36 are wide so as to straddle two pixels, variation in the number pattern and the peak periodicity of the output pattern are the same as those of FIG. 6 (C).

The peak periodicity is important in the present invention. The following explanation takes a case where the positional relation between the grid 14 and the pixels 40 is constant and the width of the X-ray absorbing layers 36 is constant as an example, but the present invention can be applied likewise to another case because variation in the positional relation between the grid 14 and the pixels 40 and variation in the width of the X-ray absorbing layers 36 do not change the peak periodicity, as described above. Note that, the effect of variation in the number itself of the X-ray absorbing layers 36 projected to the pixel 40 will be described lastly.

In a case where the relation between a grid pitch G and the pixel pitch Δ is G=2Δ/odd number such as G=2Δ of FIG. 6 and G=2Δ/3 of FIG. 7, a sequence of the number pattern takes two pixel cycles such as a number pattern of "M, M+1, M, M+1, ..." (M=0, 1, 2, ...) In the relation of G=2Δ/odd number, the number M increases to 0, 1, 2, 3, ..., with increase in the odd number to 1, 3, 5, 7, ..... The output pattern becomes "high, low, high, low, ...". The conditional expression of G=2Δ/odd number, which makes the number pattern and the output pattern as described above, can be represented as follows by using the ratio between a Nyquist frequency fN=1/(2Δ), being a division of a spatial frequency 1/Δ of the pixels 40 by 2, and a grid frequency fG=1/G.

$$fG/fN = (2\Delta)/G = \text{odd number}$$

In the following description, the relation between the pixel pitch Δ and the grid pitch G will be represented by using fG/fN.

FIG. 8 shows a case where fG/fN is not an odd number but an even number, e.g. fG/fN=2. According to a grid 14F, a grid pitch G is the same as the pixel pitch Δ (G=Δ). The number pattern is "1, 1, 1, 1, ..." and the number of the X-ray absorbing layers 36 projected to each pixel 40 does not change.

FIG. 9 shows the case of fG/fN=4. In a grid 14G, a grid pitch G is half of the pixel pitch Δ (G=Δ/2). The number pattern is "2, 2, 2, 2, ...". In other words, in the case of fG/fN=even number, the number pattern is "M+1, M+1, M+1, M+1, ..." (M=0, 1, 2, ...), and M increases to 0, 1, 2, 3, 4, with increase in fG/fN to 2, 4, 6, 8, ..... The voltage signals are kept at a constant value without having any rise and fall.

Figure 10:
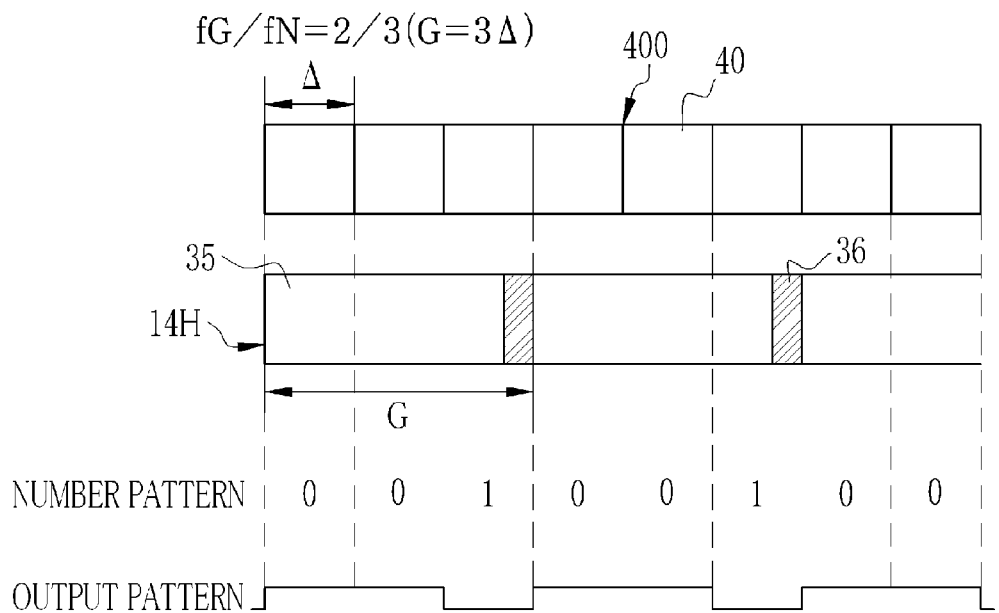
FIG. 10 is an explanatory view similar to FIG. 6 in the case of fG/fN=2/3.
Figure 11:
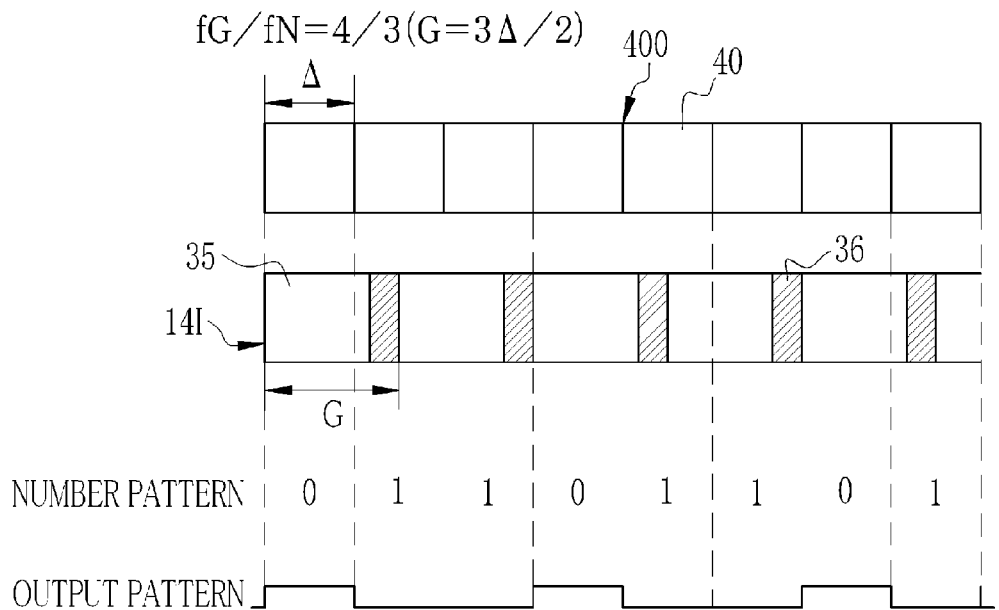
FIG. 11 is an explanatory view similar to FIG. 6 in the case of fG/fN=4/3.
Figure 12:
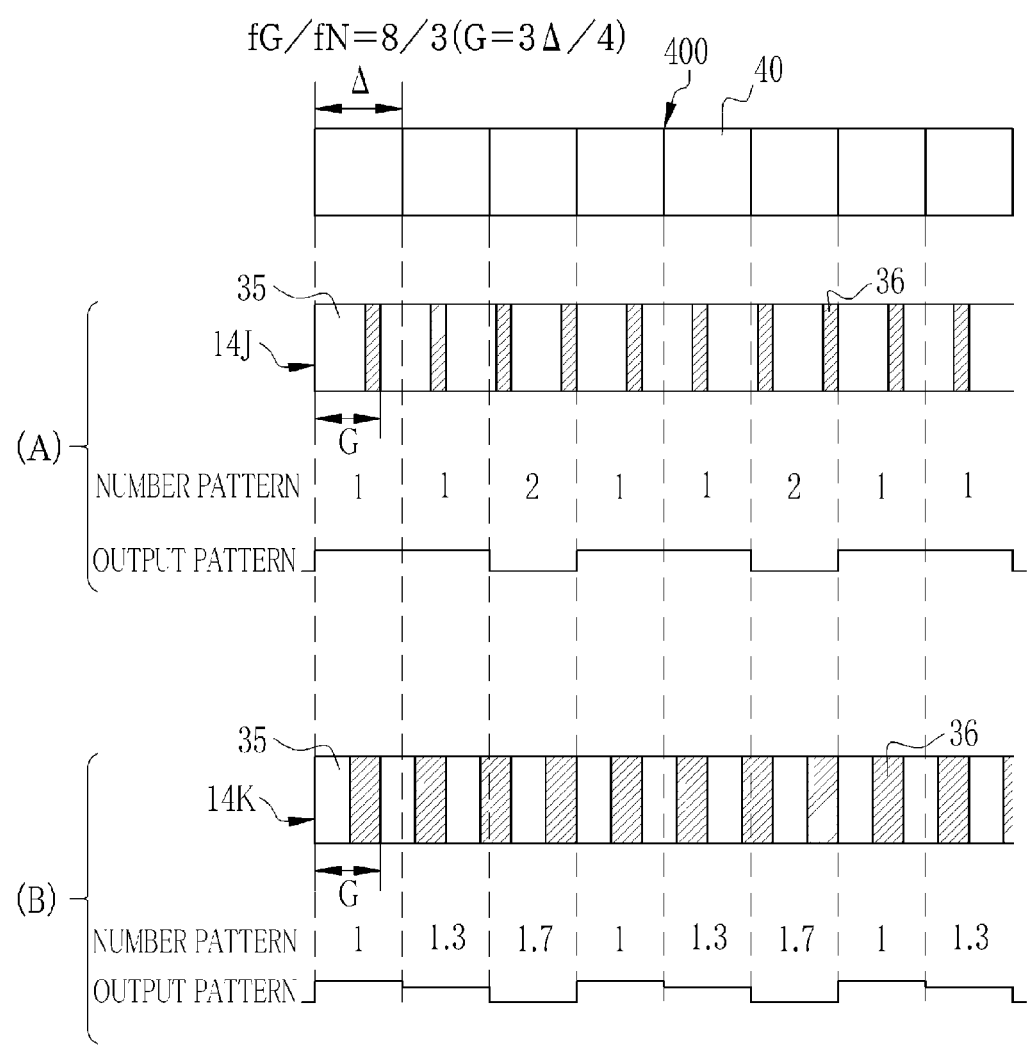
FIG. 12 is an explanatory view similar to FIG. 6 in the case of fG/fN=8/3.

FIGS. 10 to 12, for example, show cases where fG/fN is neither an odd number nor an even number, in other words, the cases of fG/fN≠integer. FIGS. 10 to 12 show the positional relation between the pixels 40 and the X-ray absorbing layers 36, the number pattern, and the output pattern in the cases of fG/fN=2/3 (G=3Δ), fG/fN=4/3 (G=3Δ/2), and fG/fN=8/3 (G=3Δ/4), respectively.

In FIG. 10 using a grid 14H, the number pattern is "0, 0, 1, 0, 0, 1, ..." and the output pattern is "high, high, low, high, high, low, ...". In FIG. 11 using a grid 14I, the number pattern is "0, 1, 1, 0, 1, 1, ..." and the output pattern is "high, low, low, high, low, low, ...". In FIG. 12, grids 14J and 14K are used. According to FIG. 12 (A), the number pattern is "1, 1, 2, 1, 1, 2, ..." and the output pattern is "high, high, low, high, high, low, ...". As described above, any pattern has a repetition of three pixel cycles. Although not shown in the drawings, in the case of fG/fN=10/3 (G=3Δ/5), the number pattern is "1, 2, 2, 1, 2, 2, ..." and the output pattern is "high, low, low, high, low, low ...".

Provided that fG/fN=[2×{integer other than multiples of 3 (=1, 2, 4, 5, 7, 8, ...)}]/3, in a case where an integer other than multiples of 3 satisfies (3n+1) (the integer other than multiples of 3 is 1, 4, 7, ...), the number pattern is "M, M, M+1, ..." (M=0, 1, 2, ...) and the output pattern is "high, high, low, high, high, low, ...". In a case where an integer other than multiples of 3 satisfies (3n+2) (the integer other than multiples of 3 is 2, 5, 8, ...), the number pattern is "M, M+1, M+1, ..." (M=0, 1, 2, ...) and the output pattern is "high, low, low, high, low, low, ...".

Note that, FIG. 12 (B) shows a case where the X-ray absorbing layers 36 have such a width as to straddle two pixels, just as in the case of FIG. 6 (C). In this case, the number pattern is "1, 1.3, 1.7, 1, 1.3, 1.7, ...", for example, but the pattern still has three pixel cycles. Also, the output pattern can be regarded as a repetition of "high, high, low, high, high, low, ...", so this case can be treated in the same manner as FIG. 12 (A).

FIG. 13 is a table that provides a summary of the value of fG/fN (the relation between the pixel pitch Δ and the grid pitch G), the number pattern, and the output pattern shown in FIGS. 6 to 12. FIG. 14 shows a grid pitch G (in a unit of μm) and the number of the X-ray absorbing layers 36 per unit of length (in a unit of number/cm) that satisfy the value of each fG/fN, in the case of the pixel pitch Δ=125 μm. In the case of fG/fN≤2 (G≥Δ), the number M of the X-ray absorbing layers 36 projected to the pixel 40 is zero or one. In the case of 2<fG/fN≤4 (Δ/2≤G<Δ), the number M of the X-ray absorbing layers 36 projected to the pixel 40 is one or two. In the case of 4<fG/fN≤6 (Δ/3≤G<Δ/2), the number M of the X-ray absorbing layers 36 projected to the pixel 40 is two or three. The number M of the X-ray absorbing layers 36 projected to the pixel 40 changes at points of fG/fN=odd number.

In the case of fG/fN<1 (G>2Δ), the number of the pixels 40 to which no X-ray absorbing layer 36 is projected is larger than that of the pixels 40 to which one X-ray absorbing layer 36 is projected, and hence "high" is larger in number in the output pattern. Likewise, in the case of 2<fG/fN<3 (2Δ/3<G<Δ) and 4<fG/fN<5 (2Δ/5<G<Δ/2), the number of "high" is larger in the output pattern. On the contrary, in the case of 1<fG/fN<2 (Δ<G<2Δ), 3<fG/fN<4 (Δ/2<G<2Δ/3), and 5<fG/fN<6 (Δ/3<G<2Δ/5), "low" is larger in number in the output pattern. In other words, provided that j=integer, in the case of 2j<fG/fN<2j+1, the number of the pixels 40 to which an M number of X-ray absorbing layers 36 are projected is larger than that of the pixels 40 to which an M+1 number of X-ray absorbing layers 36 are projected, and "high" is larger in number in the output pattern. On the contrary, in the case of 2j+1<fG/fN<2j+2, the number of the pixels 40 to which an M+1 number of X-ray absorbing layers 36 are projected is larger than that of the pixels 40 to which an M number of X-ray absorbing layers 36 are projected, and hence "low" is larger in number in the output pattern. Which of "high" and "low" is larger in number in the output pattern changes at points of fG/fN=integer.

In the case of fG/fN=even number, as described in FIGS. 8 and 9, every pixel 40 of the pixel array 400 has a constant output level of the voltage signal. A state of the output pattern formed of constant and continuous voltage signals is called flat. In this case, the measurement values measured by the measurement pixels 40b are always constant, irrespective of how to arrange the measurement pixels 40b in the pixel array 400 relative to the grid 14, how to choose the measurement pixels 40b based on the measurement area to calculate an average value of integrated measurement values by the AEC section 54, and how many pixels the pixels 40 are shifted relative to the grid 14 in the row direction X2, and therefore it is possible to precisely perform the automatic exposure control. This means that an X-ray dose applied to the object H is made the same, if the position of the electronic cassette 13 relative to the grid 14 is shifted. As a result, for the purpose of precisely performing the automatic exposure control irrespective of a shift in the positional relation between the electronic cassette 13 and the grid 14, setting fG/fN=even number allows maintaining the same X-ray irradiation amount (exposure amount) of the object H with the use of an invariable emission stop threshold value (a target dose).

Next, a condition (a condition 1) for eliminating variations in measurement with allowing a shift in the positional relation between the electronic cassette 13 and the grid 14 will be considered. This condition 1 allows a choice of the grid 14 with respect to a certain pixel pitch Δ, such that even though the output pattern is not completely flat, rises and falls in the output pattern are minimized and the output pattern is brought close to that under the condition of fG/fN=even number. At the same time, in the pixel array 400, as many measurement pixels 40b as possible are disposed in the positions of the pixels 40 that output majority voltage signals between "high" and "low" in the output pattern. In other words, as few measurement pixels 40b as possible are disposed in the positions (specific points) of the pixels 40 that output minority voltage signals.

It is important for satisfying the condition 1 to choose a grid that minimizes the rises and falls of the output pattern. Then, as for the disposition of the measurement pixels 40b, as the simplest example, the three or more measurement pixels 40b are cyclically disposed in the range of one cycle of the output pattern, which peaks at the pixel 40 outputting a minority voltage signal, in the pixel array 400. This makes it possible to dispose a more number of measurement pixels 40b in the positions of the pixels 40 outputting a majority voltage signal than in the positions of the pixels 40 outputting the minority voltage signal.

To be more specific, taking a case where the number pattern is "0, 1, 1, 1, 1, 1, 0, 1, 1, 1, 1, 1, . . . " being a repetition of one cycle of "0, 1, 1, 1, 1, 1" as an example, the number of the pixels 40 to which no X-ray absorbing layer 36 is projected is smaller than the number of the pixels 40 to which one X-ray absorbing layer 36 is projected. Thus, focusing attention on one measurement pixel 40b, the measurement pixel 40b has a greater probability of being disposed at the position of the pixel 40 to which one X-ray absorbing layer 36 is projected than at the position of the pixel 40 to which no X-ray absorbing layer 36 is projected. Considering a case where only one measurement pixel 40b is simply disposed in the pixel array 400, if the positional relation between the electronic cassette 13 and the grid 14 is getting shifted, the minimum number of the X-ray absorbing layers 36 projected to the measurement pixel 40b is zero, and the maximum number thereof is one. Accordingly, in the worst case, the output of the measurement pixel 40b has a variation range that corresponds to X-ray absorption caused by one X-ray absorbing layer 36, by vibration or the like during imaging.

On the other hand, three measurement pixels 40b are disposed per one cycle of the number pattern at two pixel cycles in the pixel array 400, for example. The number pattern of the three measurement pixels 40b is "0, 1, 1," (not in particular order) or "1, 1, 1", and the output pattern thereof is "high, low, low" (not in particular order) or "low, low, low". Assigning these three measurement pixels 40b as a group of the measurement pixels 40b that the AEC section 54 uses in calculating an average value of the dose measurement signals, the variation range of outputs of the measurement pixels 40b corresponds to the difference between the case of having the output pattern of "high, low, low" (not in particular order) and the case of having the output pattern of "low, low, low", i.e. difference in the X-ray absorption of a one-third X-ray absorbing layer 36, if being represented by the number of the X-ray absorbing layers 36. Therefore, the variation range of the outputs of the measurement pixels 40b corresponds to a one-third of the variation range in the above case of simply disposing only one measurement pixel 40b, and hence it is possible to reduce the effect of a shift of the positional relation between the electronic cassette 13 and the grid 14 on the outputs of the measurement pixels 40b.

Note that, according to the above example, at least two measurement pixels 40b are disposed in "low" positions being a flat portion of the output pattern. However, the more the number of the measurement pixels 40b disposed in this flat portion, the more it is possible to reduce the effect of a shift of the positional relation between the electronic cassette 13 and the grid 14 on outputs of the measurement pixels 40b. For example, in the case of disposing five measurement pixels 40b such that at least four of the five measurement pixels 40b are situated in a flat portion of the output pattern, the worst variation range of outputs of the measurement pixels 40b that can possibly occur in two measurements corresponds to the difference between the case of having the output pattern of "high, low, low, low, low" (not in particular order) and the case of having the output pattern of "low, low, low, low, low", which is equal to the X-ray absorption of a one-fifth X-ray absorbing layer 36. This is lower than the X-ray absorption of a one-third X-ray absorbing layer 36, and therefore it is possible to further reduce the effect of a shift of the positional relation between the electronic cassette 13 and the grid 14 on outputs of the measurement pixels 40b.

To reduce the effect of a shift of the positional relation between the electronic cassette 13 and the grid 14, outputs of the measurement pixels 40b disposed in positions other than specific points may almost compensate for the effect of variations caused by outputs of the measurement pixels 40b disposed in the specific points, and the magnitude relation between the number of the measurement pixels 40b disposed in the specific points and the number of the measurement pixels 40b disposed in the positions other than the specific points may be maintained if the positional relation between the electronic cassette 13 and the grid 14 is shifted. Furthermore, the more number of the measurement pixels 40b disposed in a flat portion of the output pattern, the more effectively the effect on the outputs of the measurement pixels 40b is reduced. With approaching the condition of fG/fN=even number, being the best case, the flat portion is increased in the output pattern itself, and hence the number of the measurement pixels 40b disposed in the flat portion can be increased. Accordingly, it is preferable to choose the grid 14 with respect to the pixel pitch Δ so as to approach the condition of fG/fN=even number.

Note that, the condition 1 is not applicable to the case of fG/fN=odd number as shown in FIGS. 6 and 7 in which "high, low" are repeated in two pixel cycles. The condition 1 is applicable to the case of having a flat portion in which voltage signals of the same level i.e. "high, high" or "low, low" are continued, such as the cases of fG/fN≠integer as shown in FIGS. 10 to 12. In the case of fG/fN=odd number, "high" and "low" repeatedly appear in the output pattern. Thus, if a more number of measurement pixels 40b are disposed in the positions of pixels 40 outputting "high" than in the positions of pixels 40 outputting "low", a shift of one pixel reverses the output of the measurement pixel 40b disposed in the "low" position into "high" and the output of the measurement pixel 40b disposed in the "high" position into "low". If five measurement pixels 40b are disposed such that at least four of the five measurement pixels 40b are situated in a flat portion of an output pattern, just as with the above example, in the worst case of reversing outputs, the output pattern of the five measurement pixels 40b becomes "high, low, low, low, low" and "low, high, high, high, high". In this case, the variation range of the outputs of the measurement pixels 40b corresponds to the X-ray absorption of three-fifths of the X-ray absorbing layer 36, which is larger than the X-ray absorption of a one-fifth X-ray absorbing layer 36 as described in the above example.

Figure 16:
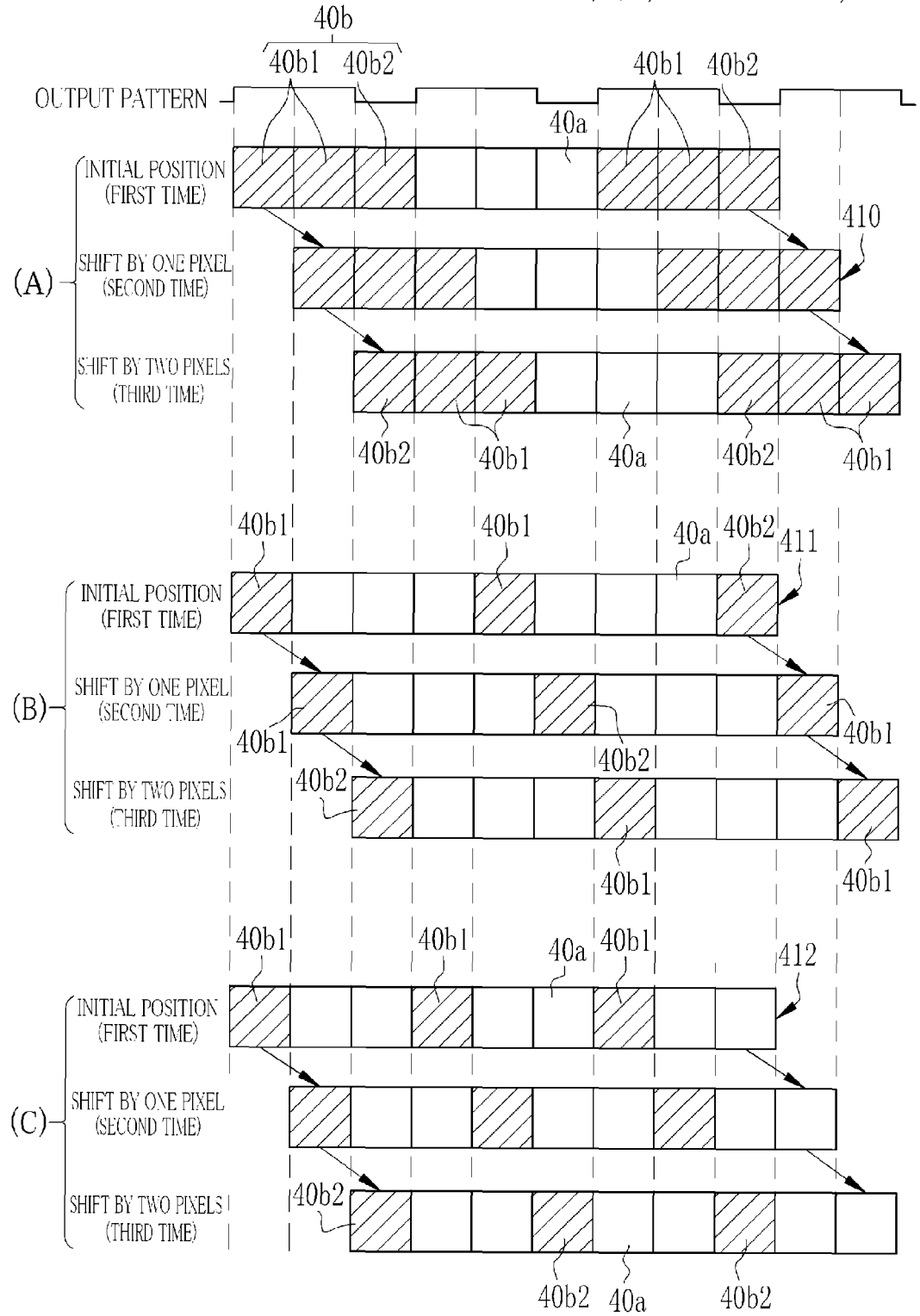

FIGS. 16 (A), (B), and (C) show mixed pixel arrays 410, 411, and 412 in which the normal pixels 40a and the measurement pixels 40b are arranged in predetermined cycles. Here the measurement pixel 40b disposed in a position outputting a voltage signal of a flat portion is referred to as a first measurement pixel 40b1. The measurement pixel 40b disposed in a specific point outputting a voltage signal (a maximum value or a minimum value) of not the flat portion is referred to as a second measurement pixel 40b2. By generalizing the disposition condition of the measurement pixels 40b according to the condition 1 by symbols and the like, it is obtained that the measurement pixels 40b1 and 40b2 are disposed such that in a case where at least a range of a cycle C (in a unit of pixel) of an output pattern is shifted C times by one pixel at a time, the number of the first measurement pixels 40b1 is larger than that of the second measurement pixels 40b2 at any time. Note that, the first measurement pixels 40b1 and the second measurement pixels 40b2 are collectively and simply called the measurement pixels 40b.

In the mixed pixel array 410, the positions of the measurement pixels 40b disposed in the image detector 30 are determined based on a pixel pitch $\Delta$, a grid pitch G of a grid 14 to be used, and the condition 1. As the pixels 40, pixels specific to the normal pixels 40a and pixels (dual function pixels) changeable into the measurement pixels 40b may be prepared. This dual function pixel can be actualized by adding another TFT, which is different from the TFT for image reading, to the normal pixel 40a. Information about the grid pitch G of the grid 14 to be used is stored in associated with the imaging condition, and the double function pixels are changed into the measurement pixels 40b in accordance with the imaging condition. Otherwise, by analyzing an image of the grid 14 that is obtained by X-ray imaging without disposing the object H, it may be determined which ones of the dual function pixels are changed into the measurement pixels 40b based on obtained information about the grid pitch G or one cycle of the output pattern.

A sufficient number of dual function pixels are preferably provided in the image detector 30. A dose measurement value is taken from every dual function pixel to the memory 51. The AEC section 54 selects the dose measurement values based on the pixel pitch $\Delta$, the grid pitch G, and the above-described condition 1. Since the pixel pitch $\Delta$ is invariable, just obtaining the information about the grid pitch G of the grid 14 to be used allows selecting the dual function pixels to be used as the measurement pixels 40b.

Furthermore, in the case of shifting a range of at least a cycle C of an output pattern C times by one pixel at a time, a condition (condition 3) for equalizing an average value of the dose measurement signals of a group of the measurement pixels 40b at any time corresponds to making the number of the first measurement pixels 40b1 uniform at any time and also making the number of the second measurement pixels 40b2 uniform at any time.

Here, C is represented by the following expression.

$$C=\{(1/fGN)/\Delta\} \times i$$

Wherein, fGN represents a frequency of the output pattern (i.e. the number of cycles of the output pattern per unit of length, and its reciprocal 1/fGN is a pitch of the output pattern). In the case of $2j < fG/fN \leq 2j+1$, $fGN=fG-2jfN$. In the case of $2j+1 < fG/fN \leq 2j+2$, $fGN=(2j+2)fN-fG$. "i" is a minimum integer whose product with $(1/fGN)/\Delta$ becomes an integer. For example, if $(1/fGN)/\Delta=7/3$, i=3.

Note that, the cycle C of the output pattern may be calculated by the above expression, or may be obtained by experiment from a stripe pattern of an X-ray image of the grid 14 that is captured by X-ray imaging without disposing the object H. In obtaining the cycle C by the experiment, the disposition of the measurement pixels 40b is determined based on the obtained cycle C.

FIG. 15 shows the value of each fG/fN, an expression for calculating fGN, and the value of C. Note that, in the case of fG/fN=even number, an output level of a voltage signal is constant and hence C=0. Note that, although this is not shown in the drawing, since a flat portion increases as a pixel pitch $\Delta$ and a grid pitch G are brought close to the condition of fG/fN=even number, as described above, the value of C gradually increases to 4, 5, . . . , as fG/fN is brought from 4/3 (C=3) close to 2 (C=0), for example.

The disposition of the measurement pixels 40b for satisfying the condition 1 and the condition 3 in the case of fG/fN=2/3, 8/3, or the like as shown in FIG. 10 or 12 will be described in detail with the use of FIG. 16. In this case, the output pattern is "high, high, low, high, high, low, . . . " being a repetition of three pixel cycles, as descried above. In this case, one of the voltage signals composing the flat portion is "high", and the other voltage signal not composing the flat portion is "low".

In the mixed pixel array 410 of FIG. 16 (A), three adjacent measurement pixels 40b and three adjacent normal pixels 40a are arranged alternately. This allows making the magnitude relation invariable such that the number of the first measurement pixels 40b1 disposed in "high" is two and the number of the second measurement pixels 40b2 disposed in "low" is one, even if the output pattern of the three adjacent measurement pixels 40b changes from "high, high, low" to "high, low, high" and "low, high, high" with a shift from an initial disposition (first time) to a relative shift of the pixels 40 in the row direction X2 by one pixel (second time) and by two pixels (third time). Thus, designating at least the three adjacent measurement pixels 40b as a group on which the AEC section 54 calculates an average value of doses makes it possible to keep the average value constant and perform the appropriate automatic exposure control, irrespective of a shift in the positional relation between the electronic cassette 13 and the grid 14. Note that, the first time refers to the initial disposition. The second time refers to the case of a shift by one pixel. The third time refers to the case of a shift by two pixels.

In the mixed pixel array 411 of FIG. 16 (B), the measurement pixels 40b are disposed in four pixel cycles. Also in this case, an output pattern of the three measurement pixels 40b changes from "high, high, low" to "high, low, high" and "low, high, high" with a shift from the initial disposition to a relative shift of the pixels 40 in the row direction X2 by one pixel and by two pixels, and therefore the magnitude relation is invariable such that the number of the first measurement pixels 40b1 disposed in "high" is two and the number of the second measurement pixels 40b2 disposed in "low" is one. Accordingly, the same effect as the case of FIG. 16 (A) can be achieved, and the three measurement pixels 40b disposed in at least four pixel cycles are designated as one group. Measuring an X-ray dose with the use of at least this group of the measurement pixels 40b makes it possible to perform the precise automatic exposure control, irrespective of the positional shift.

In the mixed pixel array 412 of FIG. 16 (C), the measurement pixels 40b are disposed in three pixel cycles, not in the four pixel cycles. According to this case, in an initial disposition and the case of a relative shift of the pixels 40 in the row direction X2 by one pixel, all the three measurement pixels 40b output "high" and become the first measurement pixels 40b1. However, in the case of a shift by two pixels, all the three measurement pixels 40b output "low" and change into the second measurement pixels 40b2, so the condition 3 is not satisfied.

According to examples of FIG. 16, since fG/fN=2/3 and 0<fG/fN≤1 (j=0), fGN=fG−2·0·fN=fG holds true. Δ=G/3 is derived from fG/fN=(2Δ)/G=2/3, so C={(1/fG)/(G/3)}×i=G/(G/3)×i=3×i. Since "i" is a minimum integer to make C into an integer, i=1 and C=3 hold true. According to FIG. 16 (A), in shifting a range of three pixels, being one cycle of the output pattern, three times by one pixel at a time, the number of the first measurement pixels 40b1 is larger than the number of the second measurement pixels 40b2 at any time. According to FIG. 16 (B), in shifting a range of nine pixels, being a triple of the cycle of the output pattern, three times by one pixel at a time, the number of the first measurement pixels 40b1 is larger than that of the second measurement pixels 40b2 at any time, and the condition 1 is satisfied at any time. Furthermore, both of FIGS. 16 (A) and (B) satisfy the condition 3, because the number of the first measurement pixels 40b1 is the same at any time and the number of the second measurement pixels 40b2 is the same at any time. On the other hand, in FIG. 16 (C), the number of the first measurement pixels 40b1 becomes zero by a shift of two pixels, so neither the condition 1 nor the condition 3 is satisfied.

Specifications of X-ray imaging require that variations in an exposure dose by a plurality of times of imaging of the same object H in the same imaging condition is within the range of ±5%. Thus, an average value of X-ray doses measured by a group of the measurement pixels 40b is not necessarily the same at any time, and may be varied more or less as long as variations are within the range of ±5%. Therefore, satisfying the condition 3 is preferable but not essential.

A condition 2 specifies the minimum number of the first measurement pixels 40b1 that is required relative to one second measurement pixel 40b2 for limiting the variations of the average value within ±5%, even if the positional shift between the grid 14 and the image detector 30 occurs.

Figure 17A:
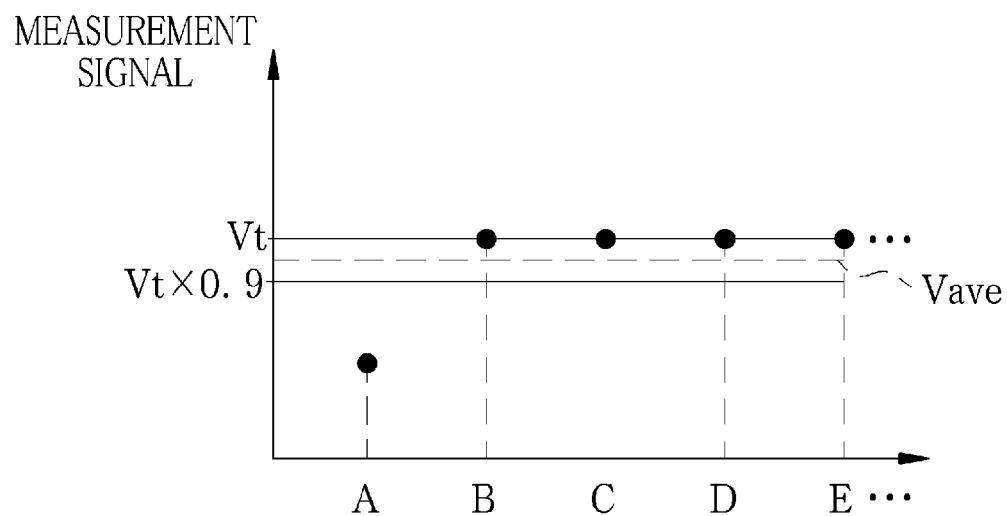
FIG. 17A is an explanatory view for determining the number of first measurement pixels that are not present in a position outputting a minimum value.

As described in FIG. 13, the output pattern of fG/fN≠integer includes two possible cases of having many "high" voltage signals (the case of 2j<fG/fN<2j+1, case 1) and having many "low" voltage signals (2j+1<fG/fN<2j+2, case 2). In the case 1, as shown in FIG. 17A, one measurement pixel A (corresponding to the second measurement pixel 40b2) is disposed in the position of the "low" voltage signal that does not compose a flat portion, and a Q number of measurement pixels B, C, D, E, . . . (corresponding to the first measurement pixels 40b1) are disposed in the positions of the "high" voltage signals that compose the flat portion. In this case, the condition 2 is satisfied if an average value Vave of the measurement signals of all the measurement pixels A, B, C, D, E, . . . is 90% or more of a value Vt of the measurement signals of the measurement pixels B, C, D, E, . . . . This is represented by a conditional expression as follows.

$$Vt \times 0.9 \leq Vave$$

Wherein, the measurement signal is an output voltage of the integrating amplifier 46a of each time performed cyclically, or an integrated voltage into which the output voltage of each time is integrated.

In a case where "a" (0<a<1) represents the X-ray absorptivity of one X-ray absorbing layer 36, and Xg represents a dose of the X-rays that has reached an X-ray incident surface of the grid 14, Vt×0.9≤Vave is represented by the following expression (1a).

$$(1 - M \cdot a) \times Xg \times 0.9 \leq \frac{1 \times \{1 - (M+1)a\} \times Xg + Q \times (1 - M \cdot a) \times Xg}{1 + Q} \quad (1a)$$

Solving the expression (1a) for Q, the following expression (1b) is obtained. An Xg component disappears.

$$Q \geq \frac{a(M + 10) - 1}{1 - M \cdot a} \quad (1b)$$

Figure 17B:
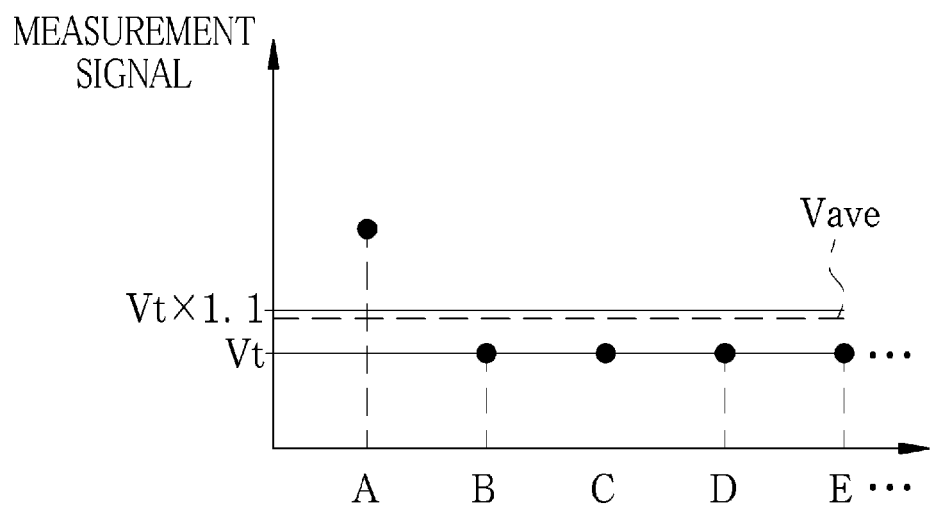
FIG. 17B is an explanatory view for determining the number of the first measurement pixels that are not present in the position outputting the maximum value.

On the other hand, in the case 2, as shown in FIG. 17B, one measurement pixel A is disposed in the position of the "high" voltage signal that does not compose a flat portion, and a Q number of measurement pixels B, C, D, E, . . . are disposed in the positions of the "low" voltage signals that compose the flat portion. In this case, the condition 2 is satisfied if an average value Vave of the measurement signals of all the measurement pixels A, B, C, D, E, . . . is 110% or less of a value Vt of the measurement signals of the first measurement pixels B, C, D, E, . . . . In this case, the following expression holds true.

$$Vave \leq Vt \times 1.1$$

This expression is represented by the following expression (2a), just as with the case 1.

$$\frac{Q \times \{1 - (1 + M)a\} \times Xg + 1 \times (1 - M \cdot a) \times Xg}{1 + Q} \leq \quad (2a)$$

$$\{1 - (M + 1)a\} \times Xg \times 1.1$$

Solving the expression (2a) for Q, the following expression (2b) is obtained. An Xg component disappears, just in the case of the expression (1b).

$$Q \geq \frac{1 - a(M + 11)}{a(M + 1) - 1} \quad (2b)$$

In either of the conditional expressions (1b) and (2b), obtaining the minimum number M or the maximum number M+1 of the X-ray absorbing layers 36 projected to the pixel 40 and the absorptivity "a" of the X-ray absorbing layer 36 allows calculating a conditional expression that defines the number Q of the first measurement pixels 40b1 with respect to one second measurement pixel 40b2. As shown in FIG. 13 and the like, the number M regularly changes in accordance with the value of fG/fN and is obtained from the value of fG/fN. Also, according to experiment of the inventors, for example, in the case of a pixel pitch Δ=150 μm and using the grid 14 of a grid pitch G=250 μm (a number of the X-ray absorbing layers of 40/cm) and a grid ratio of 14:1, it is known that the absorptivity "a" is on the order of 0.2 (20%), as the difference in a pixel value between a pixel that is the most susceptible to the X-ray absorbing layers 36 and a pixel that is the most insusceptible thereto. To determine the value of the absorptivity "a", for example, only the grid 14 is X-ray imaged without disposing the object H. In an area corresponding to the entirety or a region of interest of the obtained image, pixel values of the pixels 40 extending in a direction in parallel to the arrangement direction of the X-ray transparent layers 35 and the X-ray absorbing layers 36 are obtained. Then, the absorptivity "a" may be obtained in consideration of the difference between the maximum value of the pixel value and the minimum value thereof, and the number of the X-ray absorbing layers 36. In the case of a pixel pitch $\Delta$=150 μm and a grid pitch G=250 μm, as described above, the number of the X-ray absorbing layers 36 is zero or one, so that the absorptivity "a" is equal to a value that the difference between the maximum value of the pixel value and the minimum value thereof is divided by a dose measured in a position where the number of the X-ray absorbing layers 36 is zero.

Thus, substituting M calculated from the value of fG/fN and a=0.2 being a representative value into the above conditional expression allows obtainment of the number Q. Note that, some grids have an absorptivity "a" of 0.1 or less, but in most of these cases there is no need to consider the condition 2. In the case of an absorptivity "a" of 0.1 or less, it is important to improve the reliability of the outputs of the measurement pixels 40*b* by satisfying at least one of the conditions 1 and 3.

Note that, in calculating the absorptivity "a", the difference between the maximum value of the pixel value and the minimum value thereof and the dose measured in the position where the number of the X-ray absorbing layers 36 is zero may be values measured in a specific position or averages of values measured in a plurality of positions. In a case where the number of the X-ray absorbing layers 36 is one or two, for example, the difference between the maximum value of the pixel value and the minimum value thereof is equal to an X-ray dose absorbed by one X-ray absorbing layer 36. Since an absorbed dose is almost proportional to the number of the X-ray absorbing layers 36, an applied X-ray dose can be estimated by multiplying the difference between the maximum value of the pixel value and the minimum value thereof by the number of the X-ray absorbing layers 36. The absorptivity "a" can be calculated based on the estimated X-ray dose and the difference between the maximum value of the pixel value and the minimum value thereof.

In actual fact, the trouble of calculating the absorptivity "a" can be eliminated. Using the maximum value of the pixel value and the minimum value thereof that are obtained from an image of only the grid 14 captured without disposing the object H, for example, the maximum value may be assigned to a part of (1−M·a) of the expression (1a) or (2a), and the minimum value may be assigned to a part of $\{1-(M+1)\cdot a\}$ as is. These expressions (1a) and (2a) are expressed mathematically for the sake of ease in understanding, but actually the same as calculation using the maximum value and the minimum value as is.

Note that, strictly speaking, since a grid has a manufacturing error and the like, a common maximum value and a common minimum value in precise cycles cannot be obtained, but a relative maximum point within one cycle may be judged as a maximum value, and a relative minimum point within one cycle may be judged as a minimum value. Otherwise, assuming the worst case, in the case of satisfying the expression (1a) or (2a), variations in an exposure dose is necessarily within the desirable range of ±5%, so that a minimum value and a maximum value may be simply measured based on just the magnitude of numerical values in an area corresponding to the entirety or a region of interest of an obtained image, as described above. This facilitates easy calculation without need for judging one cycle.

A mixed pixel array 413 of FIG. 18 shows the case 1 in which fG/fN=1/2 (G=4$\Delta$), a cycle C=4, and an output pattern of "high, high, high, low, high, high, high, low, . . . ". The four measurement pixels 40*b* are disposed in five pixel cycles in the range of twenty pixels, being four times the cycle C of the output pattern. At least these four measurement pixels 40*b* compose a group on which the AEC section 54 calculates an average value of an X-ray dose. In this case, the four measurement pixels 40*b* output "high, high, high, low", "high, high, low, high", "high, low, high, high", and "low, high, high, high" in an initial disposition and in the cases of relative shifts of the pixels 40 in the row direction X2 by one pixel, two pixels, and three pixels, respectively. In any disposition, there are three first measurement pixels 40*b*1 and one second measurement pixel 40*b*2.

This is the case 1, so that the expression (1b) is applied. Since fG/fN=1/2, M=0. Also, if a=0.2, the expression (1b) is represented as follows.

$$Q \geq (0.2 \times 10 - 1)/1 = 1$$

Thus, the number of the first measurement pixels 40*b*1 relative to one second measurement pixel 40*b*2 may be set at one or more. An example of FIG. 18 satisfies the condition of the expression (1b), because the number Q=3.

On the other hand, in the case of fG/fN=4/3 of FIG. 11 being the case 2, the expression (2b) is applied. Substituting M=0 and a=0.2 into the expression (2b) and solving the expression (2b) bring the following expression.

$$Q \geq [\{1-(0.2 \times 11)\}/(0.2-1)] = 1.5$$

In the case of Q≥1.5, the number of the first measurement pixels 40*b*1 relative to one second measurement pixel 40*b*2 may be set at two, three, . . . . Note that, the number of the first measurement pixels 40*b*1 relative to two second measurement pixels 40*b*2 may be set at three. Likewise, by substituting M=1, 2, . . . and a=0.2 and solving the expressions (1b) and (2b), it becomes apparent that in an absorptivity "a"=0.2 the condition of the number Q varies in accordance with the value of fG/fN, as shown in FIG. 19.

In using one type of the grid 14, the number Q calculated from the conditional expression is used. On the other hand, in the case of using a plurality of types of grids having different numbers Q calculated from the conditional expression, the largest value of the plurality of numbers Q is assigned as a common number Q. For example, in the case of using both of a grid under a condition of Q≥1.5 and a grid of Q≥7/3 (≅2.3), the condition of Q≥7/3 is commonly used.

Next, in a case where fG/fN≠integer and the measurement pixels 40*b* are disposed in a cyclic manner, how to determine a cycle Z (in a unit of pixel) will be investigated. A repetition cycle W in overlapping an output pattern and a pattern of cyclic disposition of the measurement pixels 40*b* is the least common multiple of a cycle C of the output pattern and a cycle Z of the measurement pixels 40*b*.

$$W=LCM(C,Z)$$

"LCM" represents the least common multiple of two numerical values within parentheses. Explaining the example of FIG. 18, W=20 because the cycle C of the output pattern is 4 and the cycle Z of the measurement pixels is 5.

In a case where one second measurement pixel 40*b*2 is disposed in the position of outputting a voltage signal that does not compose a flat portion within the repetition cycle W, it is necessary to provide a Q or more number of first measurement pixels 40*b*1 whose number is determined based on the expression (1b) or (2b), relative to one second measurement pixel 40*b*2. A condition to enable this disposition is that a Q+1 number of measurement pixels 40*b* disposed in the cycle Z, that is to say, a (Q+1) Z number of measurement pixels 40*b* have to be contained in the repetition cycle W.

$$W = LCM(C, Z) \geq (Q+1)Z \approx (3)$$

The cycle Z of the measurement pixels 40*b* is determined so as to satisfy this condition (3). Note that, on the contrary, in a case where (Q+1)Z is larger than the repetition cycle W (W<(Q+1)Z), part of the (Q+1)Z measurement pixels 40*b* that is out of the repetition cycle W is positioned in the same manner as any of the measurement pixels 40*b* in the last and next repetition cycles W, and hence a Q number of first measurement pixels 40*b*1 cannot be provided relative to one second measurement pixel 40*b*2.

Since W=20, Q=3, and Z=5 in the mixed pixel array 413 of FIG. 18, the conditional expression (3) is satisfied. Note that, just as with the case of the number Q, in a case where a plurality of types of grids 14 are used in an exchanged manner and the condition of the disposition cycle Z differs from one grid 14 to another, the least common multiple of individual disposition cycles Z is assigned as an ultimate determined disposition cycle Z. For example, in the case of using both of a grid having a condition of a disposition cycle Z=3 and a grid having a condition of a disposition cycle Z=4, the ultimate determined disposition cycle Z is 12, being the least common multiple of 3 and 4.

By determining the cycle Z of the measurement pixels 40*b* so as to satisfy the conditional expression (3), a Q number of first measurement pixels 40*b*1 are present relative to at least one second measurement pixel 40*b*2. Determining Q so as to satisfy the expression (1b) or (2b) and determining the cycle Z of the measurement pixels 40*b* so as to satisfy the conditional expression (3), as described above, make it possible to satisfy the condition 2 for limiting variations in a detected X-ray dose within the range of ±5% and dispose the measurement pixels 40*b* in a cyclic manner.

The case of cyclically disposing the measurement pixels 40*b* in fG/fN≠odd number is described above, but the measurement pixels 40*b* may be disposed irregularly as long as the condition 1 is satisfied.

In this case, the measurement pixels 40*b* are disposed irregularly at the position of a β-th pixel 40 in an α×C cycle. Wherein a is a natural number of 0 or more, and β includes at least three arbitrary numbers out of 1 to C. Note that, the reason why β includes at least three arbitrary numbers out of 1 to C is based on that in order to make the number of the first measurement pixels 40*b*1 larger than the number of the second measurement pixels 40*b*2, two first measurement pixels 40*b*1 and one second measurement pixel 40*b*2 are necessary at the least.

Figure 20:
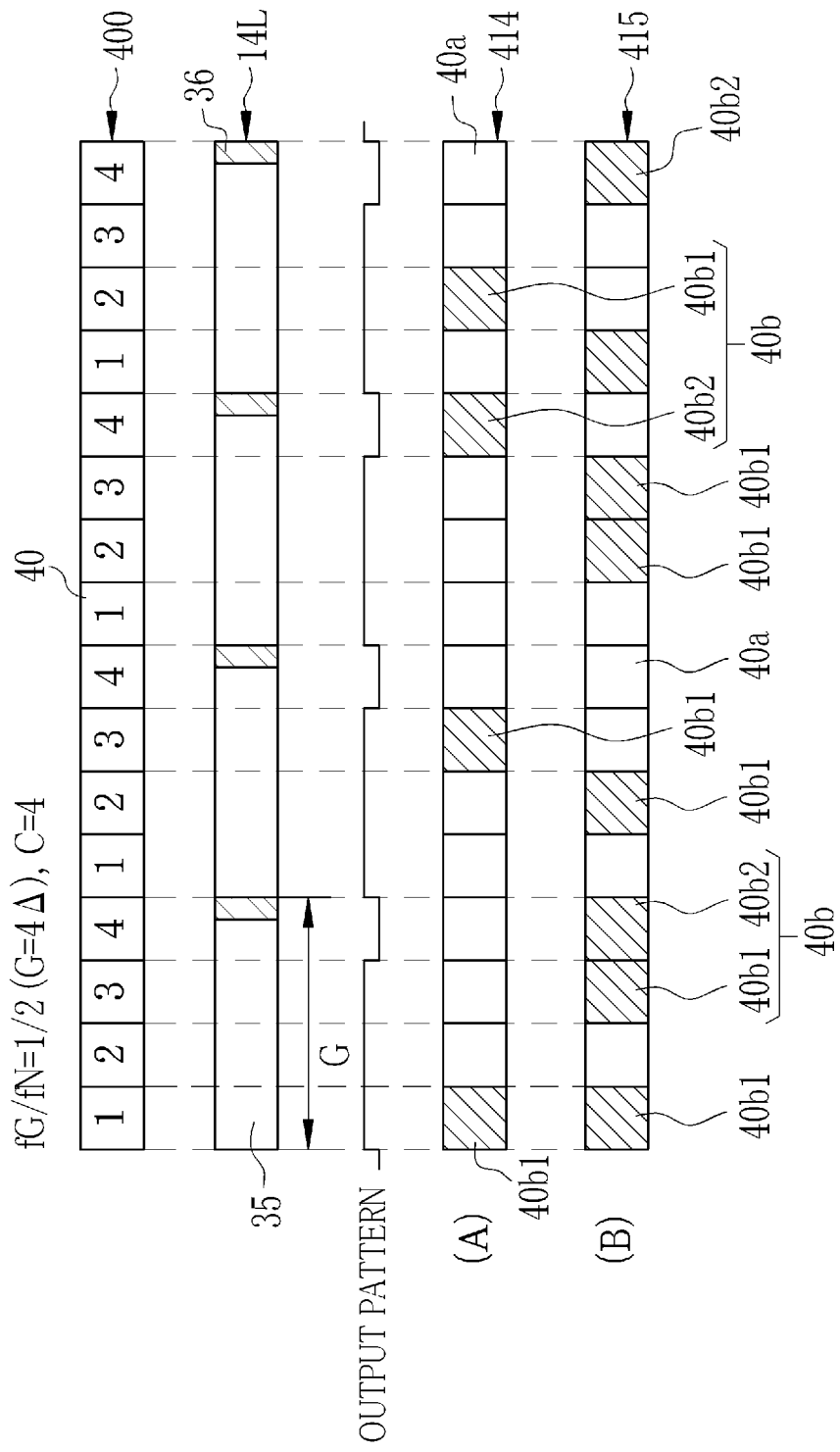
FIG. 20 is an explanatory view showing the output pattern in the case of fG/fN=1/2, and irregular disposition examples of the measurement pixels.

FIGS. 20 (A) and (B) show mixed pixel arrays 414 and 415 in which the measurement pixels 40*b* are arranged irregularly. The mixed pixel arrays 414 and 415 have the measurement pixels 40*b* arranged irregularly, but have the same output pattern "high, high, high, low, high, high, high, low, . . . " as the mixed pixel array 413 of FIG. 18. According to the mixed pixel arrays 414 and 415, four pixels 40 numbered "1" to "4" compose one set, and each set produces an output pattern of one cycle. According to FIG. 20 (A), the measurement pixels 40*b* are assigned in the position of a first pixel 40 in a first set at the left, and in the position of a third pixel 40 in a second set, and in the position of a fourth pixel 40 in a third set, and in the position of a second pixel 40 in a fourth set. In this case, α=1, 2, 3, 4, and β=1, 3, 4, 2. In the four sets, the irregularly disposed four measurement pixels 40*b* are set as a group, and the X-ray dose is measured by using at least this group. As a matter of course, the X-ray dose may be measured with the use of an integer multiple of the four sets of the number of the measurement pixels 40*b*.

According to FIG. 20 (B), the measurement pixels 40*b* are assigned in the positions of first, third, and fourth pixels 40 of a first set, in the position of a second pixel 40 of a second set, in the positions of second and third pixels 40 of a third set, and in the positions of first and fourth pixels 40 of a fourth set. In this case, a=1 and 2, or 3 and 4, and β=1, 3, 4 and 2, or 2, 3, 1 and 4. The four pixels 40*b* in the two sets (for example, the first and second sets, or the third and fourth sets) are set as a group to measure an X-ray dose. As a matter of course, an integer multiple of the two sets of the number of the measurement pixels 40*b* may be used instead.

In either of the cases of shifting the range of the four cycles of the output pattern of the mixed pixel array 414 of FIG. 20 (A), and shifting the range of the two cycles of the output pattern of the mixed pixel array 415 of FIG. 20 (B), the number of the first measurement pixels 40*b*1 becomes larger than that of the second measurement pixels 40*b*2 at any time, and hence the condition 1 is satisfied. The condition 2 is also satisfied because the number of the first measurement pixels 40*b*1 and the number of the second measurement pixels 40*b*2 are invariable at any time. In FIG. 20 (A), the measurement pixels 40*b* are irregularly disposed in the four cycles of the output pattern. In FIG. 20 (B), the measurement pixels 40*b* are irregularly disposed in the two cycles of the output pattern. The present invention can adopt both.

In the example of fG/fN≠integer as described above, one voltage signal that does not compose a flat portion is present in one cycle of the output pattern, but there is another example. For example, according to mixed pixel arrays 416 and 417 of FIGS. 21 (A) and (B), fG/fN=8/7 (G=7Δ/4) and an output pattern cycle C=7. A number pattern is "0, 1, 0, 1, 0, 1, 1, . . . " and an output pattern is "high, low, high, low, high, low, low, . . . " in which there are three "high" voltage signals that do not compose a flat portion. The pattern is similar to that in the case of fG/fN=odd number, but the mixed pixel arrays 416 and 417 satisfy the condition 1 because of existence of the flat portion that is composed of two continuous "low" voltage signals.

Figure 21:
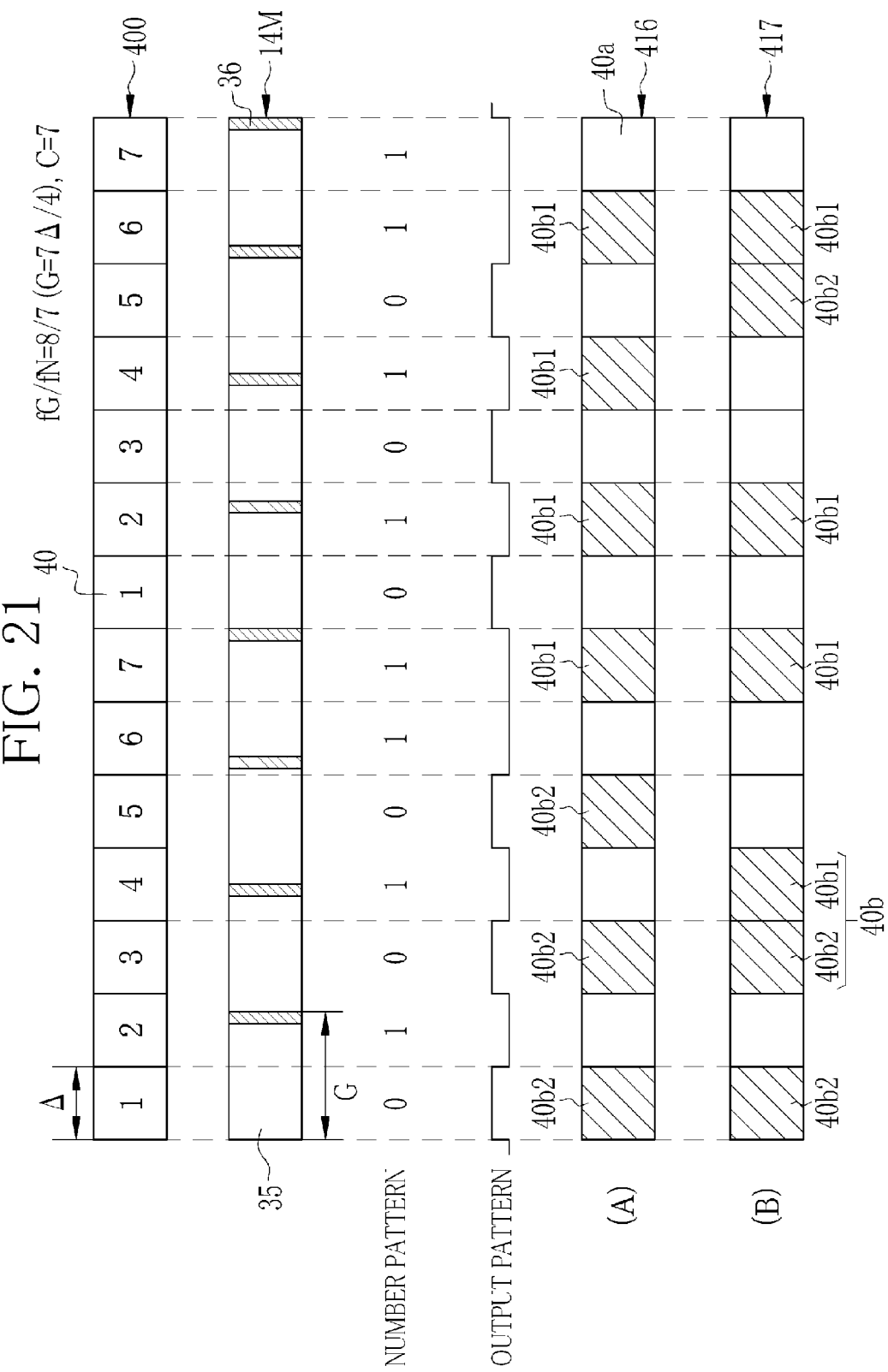
FIG. 21 is an explanatory view showing the output pattern in the case of fG/fN=8/7, and irregular disposition examples of the measurement pixels.

In this case, in the mixed pixel array 416 of FIG. 21 (A), the measurement pixels 40*b* are regularly disposed in a cycle Z of two pixels. In shifting the entire fourteen pixels, corresponding to two cycles of the output pattern, seven times by one pixel, the number of the first measurement pixels 40*b*1 becomes four and the number of the second measurement pixels 40*b*2 becomes three. Since the number of the first measurement pixels 40*b*1 is larger than the number of the second measurement pixels 40*b*2, the condition 1 is satisfied. The number of the first measurement pixels 40*b*1 and the number of the second measurement pixels 40*b*2 are invariable by the shifts of the entire fourteen pixels seven times by one pixel, so the condition 3 is satisfied too. According to the mixed pixel array 417 of FIG. 21 (B), the measurement pixels 40*b* are irregularly disposed in the positions of first, third, fourth, and seventh pixels 40 of a first set, and in the positions of second, fifth, and sixth pixels 40 of a second set (α=1 and 2, β=1, 3, 4 and 7, or 2, 5 and 6). This mixed pixel array 417 brings about the same result as the mixed pixel array 416. In either of the mixed pixel arrays 416 and 417, the seven measurement pixels 40b in the two cycles of the output pattern compose one group, and the X-ray dose is measured by using at least this group.

Note that, in the case of fG/fN≠odd number, the range of fG/fN is preferably one of the following conditional expressions (4) to (7).

$$fG/fN \leq 2/3 \qquad (4)$$

$$4/3 \leq fG/fN \leq 8/3 \qquad (5)$$

$$10/3 \leq fG/fN \leq 14/3 \qquad (6)$$

$$16/3 \leq fG/fN \leq 20/3 \qquad (7)$$

By setting the range of fG/fN at one of the conditional expressions (4) to (7), at least two continuous pixels 40 corresponding to a flat portion necessarily appear with respect to each and every pixel 40 being a specific point. Also, the number of the continuous pixels 40 corresponding to the flat portion is increased as fG/fN approaches an even number, and hence the tendency of an output pattern is easily known. The measurement pixels 40b have a high degree of flexibility in disposition, so that the measurement pixels 40b may be disposed in any manner including a simple disposition in which the three measurement pixels 40b are aligned in a row and a cyclic or irregular disposition as described above. Furthermore, there are advantages that an optimal grid 14 is easily chosen and the disposition of the measurement pixels 40b is easily determined.

Figure 22A:
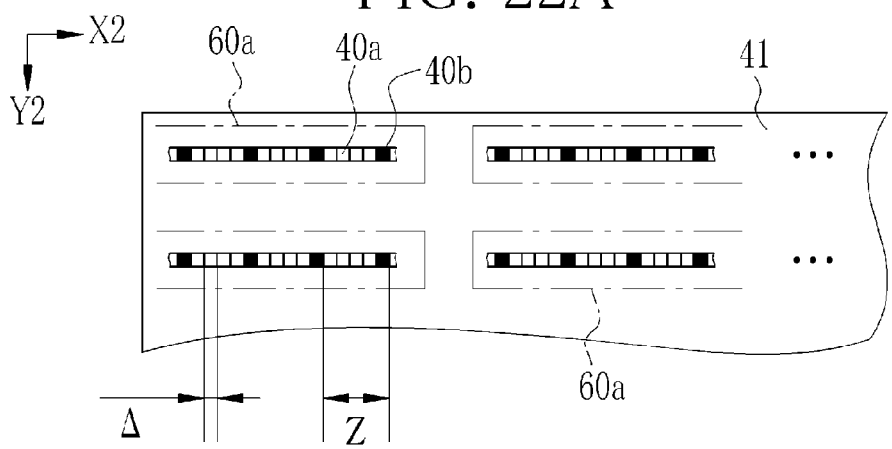
FIG. 22A is an explanatory view showing an example of a combination of mixed pixel arrays in which normal pixels and the measurement pixels are arrayed in a row direction.

Pixels of one row are described above for the sake of convenience in explanation, but in actual fact an X-ray dose is measured in a plurality of rows. Thus, in actual fact, as shown in FIG. 22A, mixed pixel arrays 60a are disposed in a predetermined pattern in the imaging area 41 in which normal pixel arrays made of only the normal pixels are arranged, such that the mixed pixel arrays 60a are substituted for the normal pixel arrays. Thus, the measurement pixels 40b are disposed in two dimensions in the imaging area 41. By choosing one or a plurality of the mixed pixel arrays 60a present within the measurement area, an X-ray dose is measured by using the chosen mixed pixel arrays 60a. Note that, the mixed pixel arrays 60a may not be uniformly disposed over the entire imaging area 41, but may be disposed only a specific area corresponding to the measurement area determined in advance, for example, left and right lung fields or the like.

Figure 22B:
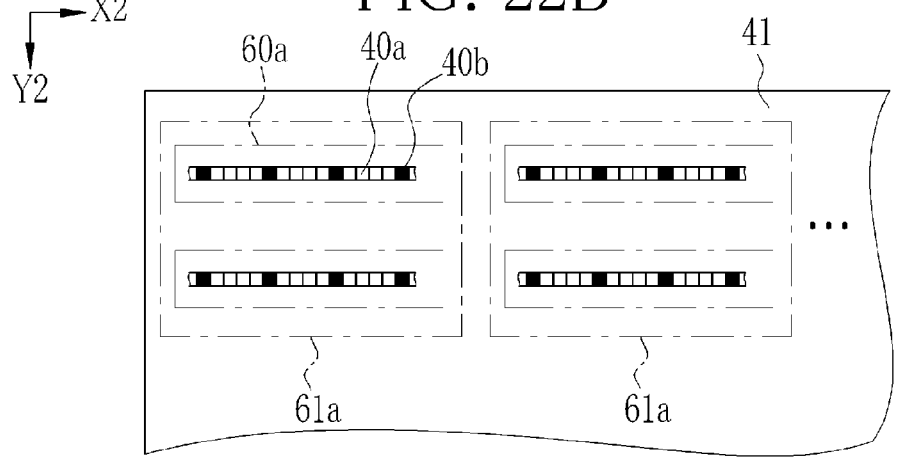
FIG. 22B is an explanatory view showing another example of a combination of the mixed pixel arrays in which the normal pixels and the measurement pixels are arrayed in the row direction.
Figure 22C:
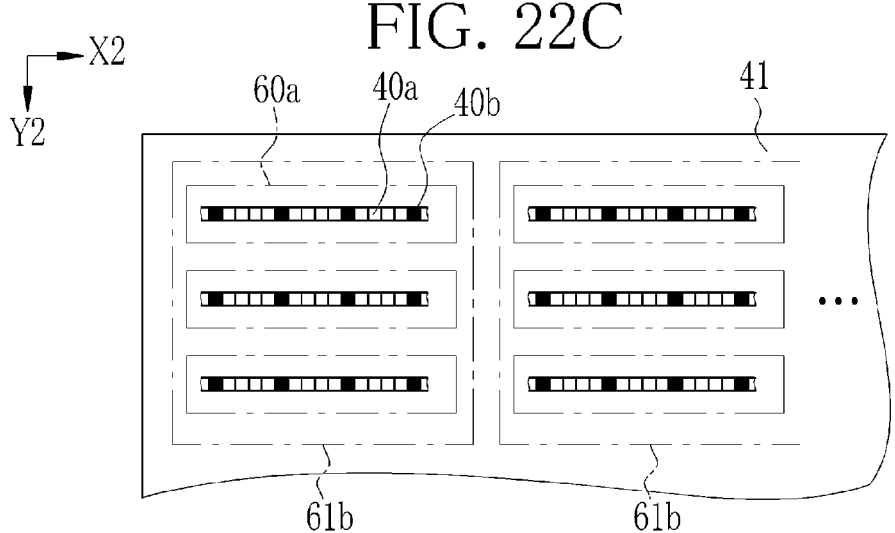
FIG. 22C is an explanatory view showing further another example of a combination of the mixed pixel arrays in which the normal pixels and the measurement pixels are arrayed in the row direction.

As an example, in the mixed pixel array 60a shown in FIG. 22A, four measurement pixels 40b are disposed in five pixel cycles (a cycle Z=5), and the mixed pixel arrays 60a are regularly arranged at predetermined intervals in the X2 and Y2 directions, for example. The cycle Z corresponds to an arrangement pitch of the measurement pixels 40b, and is five times as large as the pixel pitch Δ (Z=5Δ). One mixed pixel array 60a is a minimum unit used in dose measurement, and has the four measurement pixels 40b. For the dose measurement, a block 61a having eight measurement pixels 40b composed of two mixed pixel arrays 60a as shown in FIG. 22B, or a square block 61b having twelve measurement pixels 40b composed of three mixed pixel arrays 60a as shown in FIG. 22C may be used instead.

Also, the mixed pixel array 60a is just an example. The measurement pixels 40b may be cyclically disposed as shown in FIGS. 22A to 22C, or irregularly disposed just as with the mixed pixel arrays 414 and 415 shown in FIG. 20. The intervals between the mixed pixel arrays 60a may be random. The measurement pixels 40b may be irregularly disposed in each mixed pixel array 60a, and the intervals between the mixed pixel arrays 60a may be regular or irregular.

Figure 23:
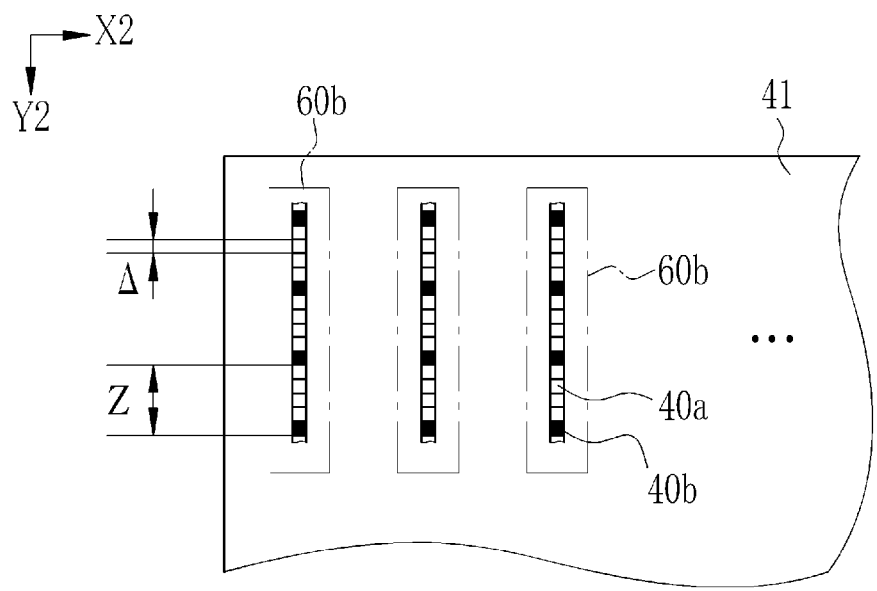
FIG. 23 is an explanatory view showing mixed pixel arrays extending in a column direction.

The above description is based on the premise that the grid 14 is set relative to the electronic cassette 13 such that the stripes of the grid 14 extend in the column direction Y2 (such that an arrangement direction X1 of each of the X-ray transparent layers 35 and the X-ray absorbing layers 36 is in parallel with the row direction X2 of the pixels 40). However, there are cases where the electronic cassette 13 is turned 90° relative to the grid 14, and the grid 14 is set in the holder 16a such that the stripes of the grid 14 extend in the row direction X2. In this case, as shown in FIG. 23, is used an imaging area 41 formed with mixed pixel arrays 60b in which an arrangement direction of a group of the measurement pixels 40b used in dose measurement extends in the column direction Y2. In this mixed pixel array 60b, a pixel pitch Δ and a cycle Z of the measurement pixels 40b are measured in the column direction Y2.

Also, the mixed pixel arrays 60a and 60b may be mixed in the imaging area 41. For example, two mixed pixel arrays 60b are disposed between two mixed pixel arrays 60a so as to forma square. Selecting which mixed pixel array 60a or 60b to use in accordance with the attachment position of the grid 14 makes it possible to perform the automatic exposure control with high precision irrespective of the attachment position. Also, the automatic exposure control can be performed with high precision irrespective of the attachment position of the grid 14 by, for example, adjusting the intervals between the mixed pixel arrays 60b in the row direction X2, such that the cycle Z of the measurement pixels 40b between the mixed pixel arrays 60b in the row direction X2 coincides with the cycle Z of the measurement pixels 40b in each mixed pixel array 60b in the column direction Y2.

In each embodiment, a plurality of measurement pixels 40b are aligned in one row or one column. However, as a mixed pixel area 60c shown in FIG. 24, a plurality of measurement pixels 40b may be arranged in a two dimensional area with being shifted in the row direction X2 and the column direction Y2.

Figure 24:
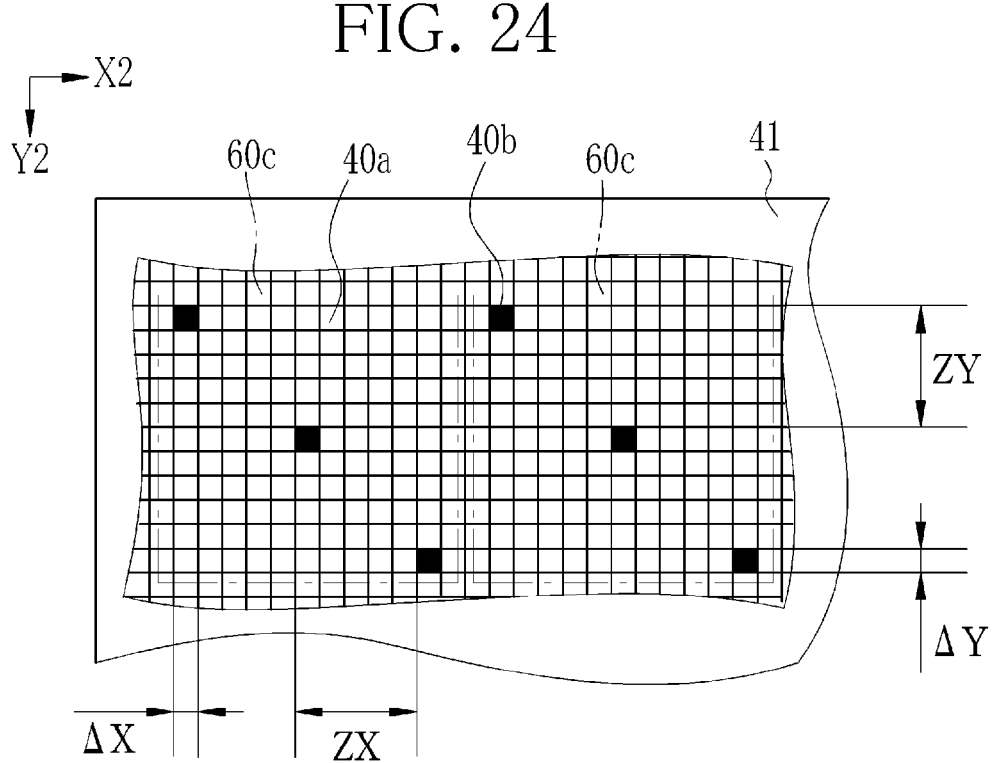
FIG. 24 is a diagram of mixed pixel areas in which the measurement pixels are disposed in a shifted manner in the row direction and the column direction.

In the mixed pixel area 60c shown in FIG. 24, the plurality of measurement pixels 40b are arrange in different rows, and, as for the row direction X2, in five pixel cycles with leaving space of four columns. As for the row direction X2, a pixel pitch ΔX and a cycle ZX of the measurement pixels 40b in the mixed pixel area 60c are the same as a pixel pitch Δ and a cycle Z of the measurement pixels 40b in the mixed pixel array 60a shown in FIG. 22. Therefore, an average value of the dose measurement signals of a group of the measurement pixels 40b in the mixed pixel area 60c is almost equal to an average value of the dose measurement signals of a group of the measurement pixels 40b in the mixed pixel array 60a. Also, as for the column direction Y2, the plurality of measurement pixels 40b are disposed in five pixel cycles, though in different columns. As for the column direction Y2, a pixel pitch ΔY and a cycle ZY of the measurement pixels 40b in the mixed pixel area 60c are the same as a pixel pitch Δ and a cycle Z of the measurement pixels 40b in the mixed pixel array 60b shown in FIG. 23.

The mixed pixel area 60c is equivalent to provision of both of the mixed pixel arrays 60a and 60b, and hence facilitates performing the automatic exposure control with high precision irrespective of the attachment position of the grid 14. Furthermore, in the case of providing both of the mixed pixel arrays 60a and 60b in a mixed manner, it is necessary to select which mixed pixel arrays 60a or 60b to use in accordance with the attachment position of the grid 14. However, the mixed pixel area 60c can be used as is irrespective of the attachment position of the grid 14. Also, the use of the mixed pixel area 60c can reduce the number of the measurement pixels 40b in half, as compared with the case of providing the mixed pixel arrays 60a and 60b in a mixed manner.

As the measurement pixel 40b of this example, in a case where the TFT and the signal line 43 are shorted out, the electric charge of the measurement pixel 40b always flows into the signal line 43. Thus, even if the measurement pixels 40b are situated in the different rows, the electric charge of the measurement pixels 40b flows into the integrating amplifiers 46 of the signal processing circuit 45 at approximately the same time. Therefore, there is a merit that the dose measurement signals of the measurement pixels 40b in the mixed pixel area 60c can be readout at the same time.

Note that, in the mixed pixel area 60c of this example, a shift amount (five pixels) of the measurement pixels 40b is the same in the row direction X2 and the column direction Y2, but may be arbitrary changed between the row direction X2 and the column direction Y2.

According to the present invention, as described above, the pixel pitch Δ and the grid pitch G are determined so as to set at fG/fN≠odd number, namely fG/fN=even number or fraction, and the number of the first measurement pixels 40b1 is set larger than the number of the second measurement pixels 40b2 at any time in shifting at least the range of the cycle C of the output pattern C times by one pixel. Thus, it is possible to reduce the effect of the second measurement pixels 40b2 on the group of the measurement pixels 40b used for calculating the average value of the dose measurement signals. Therefore, even if the positional relation between the electronic cassette 13 and the grid 14 is shifted, an average value or an addition value calculated from the entire group of the measurement pixels 40b is almost invariable.

Also, in shifting at least the range of the cycle C of the output pattern C times by one pixel, if both of the number of the first measurement pixels 40b1 and the number of the second measurement pixels 40b2 are unchanged at any time, the average value or the addition value of the dose measurement signals of the group of the measurement pixels 40b is invariable irrespective of the positional relation between the electronic cassette 13 and the grid 14. The same goes in the case of determining the pixel pitch Δ and the grid pitch G so as to satisfy the condition of fG/fN=even number.

Furthermore, in the case of regulating the number of the first measurement pixels 40b1 relative to one second measurement pixel 40b2 such that variations in an X-ray dose (exposure amount) applied by a plurality of times of imaging in the same imaging condition is within the range of ±5%, the degree of flexibility in disposition of the measurement pixels 40b is increased, though the applied X-ray dose varies more or less. The measurement pixel 40b is viewed as a defect in an X-ray image depending on structure or a way of defect correction. In actual fact, this becomes a problem in such a case that collectively disposed measurement pixels 40b form a block of the order of several pixels. To prevent the problem of making the measurement pixels 40b visible as the defect, it is important to have flexibility to enable the measurement pixels 40b to be dispersed to some extent.

Disposing the measurement pixels 40b in a cyclic manner facilitates manufacture of the image detector 30. Also, in the case of using a plurality of types of grids 14 in a switchable manner, determining the number Q and the disposition cycle Z so as to satisfy all kinds of conditions can improve universality.

Note that, in the case of disposing the measurement pixels 40b in a cyclic manner, if a ratio fG/fA=even number or fG/fA≠integer, being a ratio between the Nyquist frequency fA=1/(2ΔZ)=fN/Z and the grid frequency fG, the dose measurement signals of the measurement pixels 40b have a constant output level or an output pattern of the dose measurement signals has a flat portion. In this case, in shifting at least the range of the cycle C of the output pattern C times by one pixel, the number of the first measurement pixels 40b1 is necessarily larger than the number of the second measurement pixels 40b2 at any time. Therefore, it is possible to reduce the effect of outputs of the second measurement pixels 40b2 on outputs of the group of the measurement pixels 40b, and reduce variations in an integrated dose.

As factors that cause variations in an integrated dose of radiation by a plurality of times of imaging in the same imaging condition, there are variations in time (synchronization time of an emission start) from transmitting the emission start signal by the emission signal I/F 25 of the source control device 11 to receiving the emission start signal by the emission signal I/F 55 of the electronic cassette 13 and starting dose measurement by the AEC section 54, in addition to variations in an average value of a group of the measurement pixels 40b as described above. There are also variations in time (synchronization time of an emission stop) from transmitting the emission stop signal by the emission signal I/F 55 to receiving the emission stop signal by the emission signal I/F 25 and actually stopping the X-ray emission from the X-ray source 10 by the controller 21 of the source control device 11. Accordingly, in order to limit the variations in the radiation dose applied by a plurality of times of imaging in the same imaging condition, including the variations in the synchronization time of the emission start and the emission stop, within the range of ±5%, it is necessary to make a tolerance in variations of an average value of a group of the measurement pixels 40b more rigorous than ±5%, at the least. For this reason, "0.9" on the left side of the expression (1a) and "1.1" on the right side of the expression (2a) should not be restricted to these values. By setting the tolerance in variations of an average value of every time of a group of the measurement pixels 40b at ±k %, the expressions (1b) and (2b) are rewritten into the following expressions (1c) and (2c).

$$Q \geq \frac{k(M \cdot a - 1) + 50a}{k(1 - M \cdot a)} \quad (1c)$$

$$Q \geq \frac{k - a\{k(M+1) + 50\}}{k\{a(M+1) - 1\}} \quad (2c)$$

According to experiment of the inventors, variations in synchronization time of the emission start and stop by wired communication are on the order of 0.5 msec in total. For example, in the case of chest imaging of an emission time of 20 msec, variations in an integrated dose caused by the synchronization time of the emission start and the emission stop are 0.5/20=0.025. This corresponds to 2.5%, so the tolerance in variations of an average value of a group of the measurement pixels 40b may be set at ±2.5% or less (k≤2.5).

In the above embodiments, for the sake of convenience in explanation, three measurement pixels 40b are disposed in a row as shown in FIG. 16 (A), or measurement pixels 40b are disposed every four pixels as shown in FIG. 16 (B), or measurement pixels 40b are disposed in five pixel cycles as shown in FIG. 18. Since the measurement pixels 40b are treated as defect pixels, the less the number of the measurement pixels 40b the better. The rate of the measurement pixels 40b relative to all pixels 40 is on the order of approximately 0.01% (100 ppm; ppm (parts per million) =0.0001%). A block of the order of 10 defect pixels is conspicuous even after the defect correction, so a number of less than 10 of measurement pixels 40b are preferably disposed together.

Since periodicity is important in the above embodiment, is explained an example in which the grid and the pixels are in a certain positional relation (a position in which a left end of the grid and a left end of the pixel are aligned) and the X-ray absorbing layer has a certain width. There will be complementarily described a case where the left end of the grid and the left end of the pixel are misaligned or the positional relation between the grid and the pixels is not constant. For example, FIG. 10 shows a case in which a repetition of a cycle of fG/fN=2/3, a cycle C of the output pattern of 3, and a number pattern of "0, 0, 1". Assuming that the left end of the grid is shifted from this state to the left by 0.2 pixels, for example, the number pattern becomes "0, 0.2, 0.8, 0, 0.2, 0.8, . . . ". Thus, a cycle of "0, 0.2, 0.8" is repeated. The cycle of the number pattern is three pixels, and the cycle C of the output pattern is three pixels, just as with before the shift.

Here, as in the case of FIG. 16 (A), will be considered a case where the leftmost adjacent three pixels 40 are the measurement pixels 40b, and the next adjacent three pixels 40 are the normal pixels 40a, and the disposition of the three measurement pixels 40b and the three normal pixels 40a is repeated. In relatively shifting the pixels 40 in the row direction X2 by one pixel, the number pattern of the measurement pixels 40b is "0.2, 0.8, 0" in a shift by one pixel (second time), and the number pattern is "0.8, 0, 0.2" in a shift by two pixels (third time). In either case, an average value of the number of the X-ray absorbing layers 36 projected to one measurement pixel 40b is equally ⅓. As compared with the number pattern "0, 0, 1" of an initial position (first time) shown in FIG. 16 (A), an average value of the number of the X-ray absorbing layers 36 projected to one measurement pixel 40 is equally the same ⅓. This corresponds to the condition 3. In other words, if the initial position is shifted by less than one pixel e.g. 0.2 pixels or the like, a measurement result remains unchanged. Furthermore, if the pixels are shifted from the initial position by less than one pixel, a measurement result is the same.

Another example will be described. In the case of fG/fN=½ (G=4Δ), in a state of aligning the left end of the grid 14 and the left end of the pixel 40, the number pattern is a repetition of a cycle "0, 0, 0, 1". Provided that the leftmost adjacent three pixels 40 are measurement pixels 40b, just as in the case of FIG. 16 (A), the number pattern of the measurement pixels 40b in an initial position (first time) is "0, 0, 0". In a shift by one pixel (second time), the number pattern is "0, 0, 1". In a shift by two pixels (third time), the number pattern is "0, 1, 0". In a shift by three pixels (fourth time), the number pattern is "1, 0, 0". In the case of measuring an X-ray dose by the adjacent three measurement pixels 40b, the variation range of outputs of the measurement pixels 40b is the difference between a state where all of the three pixels output "0" of the number pattern and a state where two of the three pixels output "0" and the other one pixel output "1". Therefore, an average value of the number of the X-ray absorbing layers 36 projected to one measurement pixel 40b is 0 or ⅓. This corresponds to the condition 1.

Assuming that the left end of the grid is shifted from this state to the left by 0.2 pixels, for example, the number pattern becomes "0, 0, 0.2, 0.8, 0, 0, 0.2, 0.8, . . . ". The number pattern of the leftmost adjacent three measurement pixels 40b is "0, 0, 0.2" in an initial position (first time). The number pattern is "0, 0.2, 0.8" in a shift by one pixel (second time). The number pattern is "0.2, 0.8, 0" in a shift by two pixels (third time). The number pattern is "0.8, 0, 0" in a shift by three pixels (fourth time). As is apparent from above, the sum of the number of the X-ray absorbing layers 36 projected to three measurement pixels 40b does not exceed 1, so that an average of the number of the X-ray absorbing layers 36 projected to one measurement pixel 40b is between 0 and ⅓. In other words, if the initial position is shifted by an odd number of pixels such as 0.2 pixels or the like, or the pixels are shifted by an odd number of pixels from the initial position, variations in an average value of the number of the X-ray absorbing layers 36 projected to one measurement pixel 40b is 1 at the maximum. The positions of the measurement pixels 40b may be determined in consideration of a maximum value of the variations.

In the result, considering that outputs of arbitrary two pixels vary by one X-ray absorbing layer 36, the other cases having variations of one or less X-ray absorbing layer 36 correspond to a state in which the variations of one X-ray absorbing layer 36 is dispersed and averaged among a plurality of measurement pixels 40b. Therefore, the variation range of outputs of a group of the measurement pixels 40b does not become one or more. With considering a case having the maximum variations, the measurement pixels 40b are disposed or chosen such that the number of the first measurement pixels 40b1 is larger than the number of the second measurement pixels 40b2. This makes it possible to reduce the effect of specific points (points in which an output becomes a maximum value or a minimum value), even in a case where an initial position is shifted by an odd number of pixels or the pixels are shifted from an initial position by an odd number of pixels.

Note that, the grid has a manufacturing error. According to verification by the inventors, it is known that the manufacturing error of the grid is much smaller than 1%. Taking a grid having sixty X-ray absorbing layers per cm as an example, if the manufacturing error is 1%, the number of the X-ray absorbing layers is in the range of 59.4/cm to 60.6/cm. The error is minute less than 1, and hence does not have influence on the effect of reducing variations in an integrated dose according to the present invention.

However, the manufacturing error of the grid allowed by specification is the range of ±10%. In the worst case, taking a grid having sixty X-ray absorbing layers per cm as the specification as an example, the number of the X-ray absorbing layers is in the range of 54/cm to 66/cm. Some manufacturers sell grids as long as the grids satisfy this specification as an acceptable product, and a given number of grids having a manufacturing error of 1% or more are on the market. However, in the case of using such a grid, the measurement pixels 40b should be disposed or chosen based on 60/cm, being a central value, as a matter of course, in consideration of optimization as a whole. The same goes for the case of a manufacturing error of less than 1%. As described above, referring to the central value of the range of variations in the number of the X-ray absorbing layers due to the manufacturing error of the grid brings the large effect of reducing variations in an integrated dose. Also, each grid to be used may be X-ray imaged without disposing any object, and the actual number of the X-ray absorbing layers may be obtained from the captured image to dispose or choose the measurement pixels 40*b* based on the actual number.

Otherwise, in the case of using the grid whose nominal number of the X-ray absorbing layers is 60/cm and having a manufacturing error of a range of 54/cm to 66/cm, and the pixel pitch $\Delta=125$ µm, as shown in FIG. 14, fG/fN is in the range of 4/3 to 2. As is apparent from FIG. 13, as the value of fG/fN approaches from 4/3 to 2, a flat portion having one X-ray absorbing layer is gradually increased in the output pattern, relative to specific points having no X-ray absorbing layer. On the basis of this, if the measurement pixels 40*b* are disposed or chosen based on a minimum value 54/cm of the range of the manufacturing error, a flat portion is gradually increased with increase in the number of the X-ray absorbing layer to 60/cm and 66/cm. As a result, the number of the measurement pixels disposed in the flat portion is increased, so the effect of the specific points is reduced.

Generalizing the above idea, in a case where the relation between a minimum value of a range of a manufacturing error of a grid and a pixel pitch $\Delta$ is in any of $4/3 \leq fG/fN < 2$, $10/3 \leq fG/fN < 4$, and $16/3 \leq fG/fN < 6$, the positions of measurement pixels are determined by optimization based on the minimum value. On the contrary, in a case where the relation between a maximum value of the range of the manufacturing error of the grid and the pixel pitch $\Delta$ is in any of $fG/fN < 1$, $2 < fG/fN \leq 8/3$, $4 < fG/fN \leq 14/3$, and $6 < fG/fN \leq 20/3$, the positions of the measurement pixels are determined by optimization based on the maximum value. This makes the manufacturing error of the grid negligible, if any, and allows producing the effect of the present invention. Note that, in a case where an even number exists between two values of fG/fN calculated by using the minimum value and the maximum value of the range of the manufacturing error of the grid at any arbitrary pixel pitch $\Delta$, it cannot be judged which of the minimum value and the maximum value to use. However, the existence of an even number between the two values of fG/fN means that the relation between the pixel pitch $\Delta$ and a grid pitch G is close to fG/fN=even number, and the variation range of outputs of a group of the measurement pixels 40*b* is small. Thus, it is sufficient that the positions of the measurement pixels 40*b* are determined based on a central value.

The above embodiment describes examples in which the grid and the measurement pixels are relatively shifted in a direction in parallel with the arrangement direction X1 of the X-ray transparent layers and the X-ray absorbing layers. One reason of this is in setting the electronic cassette in the holder of the imaging stand or the imaging table, the electronic cassette being a rectangle in shape is often caught from above and below i.e. two directions for fixing. In such a state, the electronic cassette is not shifted in the Y1 direction, but tends to be shifted in the X1 direction because there is provided a certain amount of play in the X1 direction. On the contrary, in a state where the electronic cassette is fixed in the X1 direction and shiftable in the Y1 direction, no measurement error caused by the positional shift between the electronic cassette and the grid is produced.

As another case, a state in which there is more or less play in both of the X1 direction and the Y1 direction will be considered. In this case, the grid is sometimes inclined more or less relative to the pixels. The inclination of less than 90° relative to the pixels causes that the grid pitch appears to become large. For example, in the case of the grid having the number of the X-ray absorbing layers of 60/cm, the grid pitch G is approximately 167 µm. If this grid is inclined 10°, the grid pitch G comes to be 167/cos 10°=approximately 170 µm (the number of the X-ray absorbing layers of approximately 59/cm). Provided that $\theta$ represents an inclination angle, the grid pitch G appears to be $1/\cos \theta$ times larger than a value without having the inclination. If $\theta=10°$, $1/\cos \theta$=approximately 1.02. Even if there is play in both of the X1 direction and the Y1 direction, it is impossible in actual fact to use the grid in a state of being inclined by 10° relative to the pixels. Even if the grid is inclined 10° relative to the pixels, this is an error of the order of ±2% at the maximum. This is less than the above-described manufacturing error ±10% of the grid in general, and hence has little effect. Thus, the certain amount of inclination of the grid relative to the pixels causes no problem, if the positions of the measurement pixels 40*b* are determined based on the central value, as described in the description of the manufacturing error of the grid. Also, in a case where the inclination angle $\theta$ is in a known range, the maximum value of the grid is calculated, and the positions of the measurement pixels may be determined by optimization based on the minimum value or the maximum value in accordance with the range of fG/fN, just as in the case of the manufacturing error of the grid as described above.

Since the grid 14 is attached to the housing 31 of the electronic cassette 13 or the holder 16*a* of the imaging stand 16, there is a distance of at least the thickness of the housing 31 between the grid 14 and the imaging area 41. Therefore, a projection image of the grid 14 to the imaging area 41 is actually enlarged as compared in the case of contacting the grid 14 and the imaging area 41. In the above embodiment, the expression for calculating the cycle C of the output pattern does not consider the distance between the grid 14 and the imaging area 41. However, since the distance between the grid 14 and the imaging area 41 is much smaller than the distance (SID; source image distance) between the focal point 10*a* and the imaging area 41, an enlargement factor of the projection image of the grid 14 to the imaging area 41 is slight as compared to the case of contacting the grid 14 and the imaging area 41. Thus, there is no problem if the distance between the grid 14 and the imaging area 41 is not considered in the expression calculating the cycle C of the output pattern. As a matter of course, for the sake of better precision, the cycle C of the output pattern may be calculated by an expression with consideration given to the distance between the grid 14 and the imaging area 41. Note that, in the case of obtaining the cycle C by experiment from a fringe pattern of an X-ray image of the grid 14 that is captured without disposing the object H, the distance between the grid 14 and the imaging area 41 is reflected in the fringe pattern of the X-ray image, so there is no need for giving attention to the distance between the grid 14 and the imaging area 41.

Some X-ray imaging systems do not have a communication function between the source control device 11 and the electronic cassette 13. In this case, the emission start signal is not transmitted to the source control device 11 and the electronic cassette 13. In the X-ray imaging system without having the communication function, as shown in FIG. 25, an image detector 65 is provided with an emission start judging section (hereinafter called judging section) 66. This judging section 66 stores an emission start threshold value, and judges the moment of starting the X-ray emission by comparison between a measurement value and the threshold value. Also, the emission time of the X-rays is inputted from the console 15 based on the contents of the examination order. This emission time is transmitted to the electronic cassette 13. Note that, no AEC section 54 is provided for lack of the communication function between the source control device 11 and the electronic cassette 13.

During standby for X-ray imaging, the integrating amplifiers 46 are reset in relatively short cycles, and the measurement of an X-ray dose is repeatedly carried out by using a group of the measurement pixels 40b. A measurement value of each measurement pixel 40b measured each time is sent to the memory 51. Since this embodiment aims at detecting an X-ray emission, the measurement value of previous time is updated with the measurement value of this time in the memory 51. Upon updating the memory 51 with the new measurement values, the judging section 66 reads out the measurement values of the group of the measurement pixels 40b present in the irradiation field or all the measurement pixels present in the irradiation field, and calculates an average value thereof. Note that, it is preferable to choose only the measurement pixels 40b that are present in a directly exposed area on which the X-rays are directly applied without passing through the object in the imaging area, and judge the start of an emission with the use of the chosen measurement pixels 40b. Instead of the measurement pixels 40b, a specific dose measurement sensor group may be disposed in the directly exposed area.

The judging section 66 judges the start of an X-ray emission at the instant when the average value exceeds the emission start threshold value. In a case where the judging section 66 judges the start of the X-ray emission, the controller 52 shifts the operation of the image detector 65 from the reset operation to the accumulation operation, to detect an X-ray image by the normal pixels 40a as described above. The controller 52 measures an elapsed time from the start of the X-ray emission, and ends the accumulation operation after a lapse of the X-ray emission time set in the console 15. After the completion of X-ray imaging, the X-ray image is read out of the electronic cassette 13, as described above.

In imaging using a grid, the grid 14 is disposed in front of the electronic cassette 13. Disposing the measurement pixels 40b based on the above conditions eliminates the effect of a positional shift that occurs between the electronic cassette 13 and the grid 14. Accordingly, the electronic cassette 13 can precisely detect the start of an X-ray emission, and detect an X-ray image by the image detector 65.

According to each of the above embodiments, as shown in FIG. 5, the normal pixels 40a and the measurement pixel 40b are connected to the same signal line 43. Since the measurement pixels 40b become defect pixels, the number of the measurement pixels is much smaller than that of the normal pixels 40a. A slight amount of leak current flows from the normal pixel 40a even in an off state of the TFT. The number of the normal pixels 40a is much larger than that of the measurement pixels, so there is a problem that addition of electric charge based on the leak current of the normal pixels 41a to electric charge of the measurement pixel 40b greatly affects the dose measurement signal as noise. Therefore, it is preferable that a column (a column outputting the voltage signal V1 or V3 of FIG. 5) having no measurement pixel 40b be provided next to a column (for example, a column outputting the voltage signal V2 of FIG. 5) having the measurement pixel 40b, and in sampling the dose measurement signal by the AEC section 54, an output of the column having no measurement pixel 40b is subtracted from an output of the column having the measurement pixel 40b in order to eliminate the effect of the electric charge caused by the leak current and take out only an output based on the electric charge from the measurement pixel 40b. For this reason, it is preferable that at least one normal pixel 40a be disposed between two measurement pixels 40b as shown in FIG. 16 (B), rather than disposing three measurement pixels 40b in a row as shown in FIG. 16 (A).

According to the above embodiments, in the measurement pixel 40b, the source electrode and the drain electrode of the TFT for readout, which is driven by the gate driver 44, is shorted out. Instead of shorting the TFT for readout, every pixel 40 may be provided with another TFT for measurement. While the TFT for readout is turned off in the accumulation operation, the TFT for measurement may be selectively turned on to make the electric charge produced in the pixel 40 flow into the capacitor 46b of the integrating amplifier 46. The pixel 40 whose TFT for measurement is selectively turned on is used as the measurement pixel 40b. Thereby, in the case of selectively using a plurality of types of grids 14, it is possible to change the normal pixel 40a into the measurement pixel 40b in accordance with the type of each grid 14. In this case, position data of each grid 14 is stored in a memory. The controller 52 reads out the position data corresponding to the grid to be used. Then, a specific gate driver is driven to turn on the TFTs for measurement of the measurement pixels 40b designated by the position data in predetermined cycles. Thereby, accumulated electric charge is read out once every predetermined time and the X-ray dose per unit of time is measured.

Also, with taking advantage of the fact that an electric current that is based on electric charge produced in a pixel flows through the bias line for supplying the bias voltage to each pixel, an electric current flowing through the bias line connected to a specific pixel may be sampled to detect the X-ray dose. In this case, the pixel whose electric current flowing through the bias line is sampled is designated as the measurement pixel. In a like manner, a leak current flowing from the pixel may be sampled to detect a dose. Also in this case, the pixel whose leak current is sampled is designated as the measurement pixel.

In the above embodiments, the pixels 40 are disposed at the predetermined pitch $\Delta$ in two dimensions in the imaging area. Parts of the pixels 40 are designated as the measurement pixels 40b, and the others are designated as the normal pixels 40a. The normal pixels 40a and the measurement pixels 40b are of the same size. Note that, the measurement pixel 40b may be larger or smaller than the normal pixel 40a in size. Also, slim dose measurement sensors extending in the X2 or Y2 direction may be disposed between columns or rows of the normal pixels 40a so as to satisfy the above conditions. However, the length of the dose measurement sensor is made shorter than ten pixels 40 aligned in a row, so that the defect correction is effective at making the dose measurement sensor inconspicuous.

The TFT type image detector is described as an example in the above embodiments, but a CMOS (complementary metal oxide semiconductor) type image detector may be used instead. Also, the present invention is not limited to the electronic cassette being a portable type X-ray image detecting device, and may be applied to an integral type X-ray image detecting device attached to the imaging stand or the imaging table. Furthermore, the present invention is applicable to the case of capturing another type of radiation such as γ-rays, instead of the X-rays.

The present invention is not limited to the embodiments described above, and the embodiments can be combined within the scope of configurations described in the embodiments.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device having an image detector formed with an imaging area, and said radiation image detecting device being used together with a grid capable of being disposed in front of said image detector, said radiation image detecting device comprising:

said grid having strip-shaped radiation transparent layers and radiation absorbing layers extending in a first direction to remove scattered rays produced upon radiation passing through an object, a plurality of said radiation transparent layers and said radiation absorbing layers being alternatingly formed at a grid pitch, G, in a second direction orthogonal to said first direction;

said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and provided that said image detector captures a radiographic image of said grid, and said dose measurement sensor that is not situated in a specific position in which an output signal is at a maximum value or a minimum value is designated as a first dose measurement sensor and said dose measurement sensor that is in said specific position is designated as a second dose measurement sensor, the position of said plurality of dose measurement sensors being determined so as to satisfy the following condition 1:

condition 1:

provided that fG/fN≠odd number and said grid and said pixels are relatively shifted to said second direction C times by one pixel, the number of said first dose measurement sensors is larger than the number of said second dose measurement sensors at any time within the range of a cycle C, wherein fG=1/G represents a grid frequency, fN=1/(2Δ) represents a Nyquist frequency of said pixels, and said cycle C is a cycle of a repetition pattern appearing in said second direction in said radiographic image of said grid, and is represented in units of the number of said pixels.

2. The radiation image detecting device according to claim 1, further comprising:

a judging section for judging an emission state of said radiation based on a measurement value of at least a group of dose measurement sensors, provided that said group of dose measurement sensors includes a part of said plurality of dose measurement sensors, disposed in said second direction, of a number corresponding to said cycle C; and a controller for performing control in accordance with a judgment result of said judging section.

3. The radiation image detecting device according to claim 2, wherein said pixels include a normal pixel for detecting said radiographic image and a measurement pixel of the same size as said normal pixel and used as dose measurement sensor, and said normal pixel and said measurement pixel are disposed in said first and second directions in two dimensions in a mixed manner.

4. The radiation image detecting device according to claim 3, wherein said normal pixel and said measurement pixel are connected to a common signal processing circuit, and electric charge of said normal pixel is accumulated and electric charge of said measurement pixel is read out to said signal processing circuit during emission of said radiation.

5. The radiation image detecting device according to claim 3, wherein said group of measurement pixels are further situated so as to satisfy the following condition 2:

condition 2:

provided that said grid and said pixels are relatively shifted by one pixel, the following conditional expression 1 or the following conditional expression 2 is satisfied at said any time:

in the case of $2j < fG/fN < 2j+1$, conditional expression 1:

$$Q \geq \frac{k(M \cdot a - 1) + 50a}{k(1 - M \cdot a)} \quad (1c)$$

in the case of $2j+1 < fG/fN < 2j+2$, conditional expression 2:

$$Q \geq \frac{k - a\{k(M+1) + 50\}}{k\{a(M+1) - 1\}} \quad (2c)$$

wherein,

"Q" represents the number of first measurement pixels corresponding to said first dose measurement sensors, relative to one second measurement pixel corresponding to said second dose measurement sensor, "a" represents a radiation absorptivity of one of said radiation absorbing layers, "M" represents a minimum value of the number of said radiation absorbing layers projected to said measurement pixel, "k" represents a tolerance (±k %) in variations of said measurement value of said group of measurement pixels in every of said times, and "j" represents an integer.

6. The radiation image detecting device according to claim 5, wherein k≤5.

7. The radiation image detecting device according to claim 5, wherein k≤2.5.

8. The radiation image detecting device according to claim 5, wherein a disposition cycle Z of said measurement pixels is determined so as to satisfy the following conditional expression 3:

$$LCM(C,Z) \geq (Q+1) \cdot Z \quad \text{conditional expression 3:}$$

wherein,

Z represents a pixel number of a disposition cycle of said measurement pixels, and LCM(C,Z) represents a least common multiple of said C and said Z.

9. The radiation image detecting device according to claim 8, wherein in the case of selectively using a plurality of grids having different minimum values of said Q, a highest value out of said minimum values of said Q is used in common.

10. The radiation image detecting device according to claim 8, wherein in the case of selectively using a plurality of grids having different conditions of said disposition cycle Z, a least common multiple of a plurality of said disposition cycles Z is used as a disposition cycle Z sharable among said grids.

11. The radiation image detecting device according to claim 5, wherein the position of said group of measurement pixels is irregularly determined.

12. The radiation image detecting device according to claim 3, wherein under said condition 1, values of said pixel pitch Δ and said grid pitch G are determined so as to satisfy one of the following conditional expressions 4 to 7:

$fG/fN \leq 2/3$    conditional expression 4:

$4/3 \leq fG/fN \leq 8/3$    conditional expression 5:

$10/3 \leq fG/fN \leq 14/3$    conditional expression 6:

$16/3 \leq fG/fN \leq 20/3$.    conditional expression 7:

13. The radiation image detecting device according to claim 8, wherein under said condition 1, values of said pixel pitch Δ and said grid pitch G are determined so as to satisfy one of the following conditional expressions 4 to 7:

$fG/fN \leq 2/3$    conditional expression 4:

$4/3 \leq fG/fN \leq 8/3$    conditional expression 5:

$10/3 \leq fG/fN \leq 14/3$    conditional expression 6:

$16/3 \leq fG/fN \leq 20/3$.    conditional expression 7:

14. The radiation image detecting device according to claim 3, wherein provided that fA represents the ratio fN/Z between a disposition cycle Z of said measurement pixels and a Nyquist frequency fN of said measurement pixels, values of said pixel pitch Δ, said grid pitch G, and said disposition cycle Z are determined such that fG/fA=even number or fG/fA≠integer holds true.

15. The radiation image detecting device according to claim 3, wherein in the case of satisfying said condition 1, the position of said group of measurement pixels is determined so as to further satisfy the following condition 3:
condition 3:
the number of first measurement pixels corresponding to said first dose measurement sensors is invariable at said any time, and the number of second measurement pixels corresponding to said second dose measurement sensors is invariable at said any time.

16. The radiation image detecting device according to claim 3, wherein in automatic exposure control, said judging section judges whether or not a total radiation dose being an integrated value of a radiation dose measured by each of said measurement pixels or an average value of said total radiation doses reaches a target dose, and stops emission of said radiation in a case where said total radiation dose or said average value is judged to have reached said target dose.

17. The radiation image detecting device according to claim 3, wherein the decision of the position of said group of measurement pixels stipulated in said second direction is also applied to said first direction.

18. The radiation image detecting device according to claim 3, wherein said image detector is an electronic cassette contained in a portable housing.

19. A radiation imaging system comprising:
(A) a radiation source for applying radiation to an object;
(B) a source control device for controlling operation of said radiation source; and
(C) a radiation image detecting device having an image detector formed with an imaging area, and used together with a grid capable of being disposed in front of said image detector, said radiation image detecting device including:
said grid having strip-shaped radiation transparent layers and radiation absorbing layers extending in a first direction to remove scattered rays produced upon radiation passing through an object, a plurality of said radiation transparent layers and said radiation absorbing layers being alternatingly formed at a grid pitch, G, in a second direction orthogonal to said first direction;
said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and
provided that said image detector captures a radiographic image of said grid, and said dose measurement sensor that is not situated in a specific position in which an output signal is at a maximum value or a minimum value is designated as a first dose measurement sensor and said dose measurement sensor that is in said specific position is designated as a second dose measurement sensor, the position of said plurality of dose measurement sensors being determined so as to satisfy the following condition 1:
condition 1:
provided that fG/fN≠odd number and said grid and said pixels are relatively shifted to said second direction C times by one pixel, the number of said first dose measurement sensors is larger than the number of said second dose measurement sensors at any time within the range of a cycle C, wherein
fG=1/G represents a grid frequency,
fN=1/(2Δ) represents a Nyquist frequency of said pixels, and
said cycle C is a cycle of a repetition pattern appearing in said second direction in said radiographic image of said grid, and is represented in units of the number of said pixels.

20. An operation method of a radiation imaging system including:
(A) a radiation source for applying radiation to an object;
(B) a source control device for controlling operation of said radiation source; and
(C) a radiation image detecting device having an image detector formed with an imaging area, and used together with a grid capable of being disposed in front of said image detector, said radiation image detecting device including:
said grid having strip-shaped radiation transparent layers and radiation absorbing layers extending in a first direction to remove scattered rays produced upon radiation passing through an object, a plurality of said radiation transparent layers and said radiation absorbing layers being alternatingly formed at a grid pitch, G, in a second direction orthogonal to said first direction;
said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and provided that said image detector captures a radiographic image of said grid, and said dose measurement sensor that is not situated in a specific position in which an output signal is at a maximum value or a minimum value is designated as a first dose measurement sensor and said dose measurement sensor that is in said specific position is designated as a second dose measurement sensor, the position of said plurality of dose measurement sensors being determined so as to satisfy the following condition 1:

condition 1:

provided that $fG/fN \neq$ odd number and said grid and said pixels are relatively shifted to said second direction C times by one pixel, the number of said first dose measurement sensors is larger than the number of said second dose measurement sensors at any time within the range of a cycle C, wherein $fG=1/G$ represents a grid frequency, $fN=1/(2\Delta)$ represents a Nyquist frequency of said pixels, and said cycle C is a cycle of a repetition pattern appearing in said second direction in said radiographic image of said grid, and is represented in units of the number of said pixels, said operation method comprising the steps of:

(i) measuring a radiation dose by at least a group of dose measurement sensors out of said plurality of dose measurement sensors;

(ii) judging whether or not a total radiation dose being an integrated value of each radiation dose measured by said group of dose measurement sensors or an average value of said total radiation doses reaches a target dose; and (iii) stopping the operation of said radiation source to stop emission of said radiation, at the instant when said total radiation dose or said average value reaches said target dose.

* * * * *